United States Patent [19]
Nevalainen et al.

[11] Patent Number: 5,830,733
[45] Date of Patent: Nov. 3, 1998

[54] NUCLEIC ACID MOLECULES ENCODING PHYTASE AND PH2.5 ACID PHOSPHATASE

[75] Inventors: Helena K. M. Nevalainen, North Epping, Australia; Marja T. Paloheimo, Helsinki, Finland; Arja S. K. Miettinen-Oinonen, Masala, Finland; Tuula K. Torkkeli, Helsinki, Finland; Michael Cantrell, Moscow, Id.; Christopher S. Piddington; John A. Rambosek, both of Seattle, Wash.; Marja K. Turunen, Helsinki; Richard B. Fagerström, Espoo, both of Finland; Christine S. Houston, Bothell, Wash.

[73] Assignee: Röhm Enzyme Finland Oy, Rajamäki, Finland

[21] Appl. No.: 609,426

[22] Filed: Mar. 1, 1996

Related U.S. Application Data

[60] Division of Ser. No. 923,724, Jul. 31, 1992, which is a continuation-in-part of Ser. No. 496,155, Mar. 19, 1990, Pat. No. 5,273,887, which is a continuation of Ser. No. 44,077, Apr. 29, 1987, abandoned.

[30] Foreign Application Priority Data

Apr. 30, 1986 [GB] United Kingdom .................. 8610600

[51] Int. Cl.$^6$ .............................. C12N 1/15; C12N 15/55; C12N 15/63; C12P 21/02
[52] U.S. Cl. .............................. 435/196; 435/6; 435/91.2; 435/252.3; 435/254.2; 435/254.11; 435/256.7; 435/320.1; 435/325; 435/410; 536/23.2
[58] Field of Search .................................. 435/91.2, 196, 435/254.6, 320.1, 325, 252.3, 254.11, 410, 254.2, 256.7, 6; 536/23.2

[56] References Cited

U.S. PATENT DOCUMENTS

| | | | |
|---|---|---|---|
| 3,297,548 | 1/1967 | Ware et al. | 435/196 |
| 3,966,971 | 6/1976 | Morehouse et al. | 435/272 |
| 4,914,029 | 4/1990 | Caransa et al. | 435/101 |
| 5,217,959 | 6/1993 | Sabin | 514/23 |
| 5,298,405 | 3/1994 | Nevalainen et al. | 435/209 |
| 5,436,156 | 7/1995 | Van Gorcom et al. | 435/252.3 |
| 5,443,979 | 8/1995 | Vanderbeeke et al. | 435/195 |
| 5,554,399 | 9/1996 | Vanderbeeke et al. | 426/49 |
| 5,593,963 | 1/1997 | Van Ooijen et al. | 514/12 |

FOREIGN PATENT DOCUMENTS

| | | |
|---|---|---|
| 0 215 594 A2 | 3/1987 | European Pat. Off. |
| 2 244 234 A2 | 11/1987 | European Pat. Off. |
| 0 287 152 A1 | 10/1988 | European Pat. Off. |
| 0 420 358 A1 | 4/1991 | European Pat. Off. |
| WO 91/05053 | 4/1991 | WIPO . |
| WO 92/01797 | 2/1992 | WIPO . |
| WO 94/03072 | 2/1994 | WIPO . |

OTHER PUBLICATIONS

Harkki et al., Bio Technology 7:596–601, 1989.
Bailey, M.J. and K.M.H. Nevalainen, "Induction, isolation and testing of stable *Trichoderma reesei* mutants with improved production of solubilizing cellulase," *Enzyme Microb. Technol.* 3:153–157 (1981).
Christen, A.A. et al., "Cloning of the Phytase Gene from Germinating Soybeans," *J.Cell. Biochem. Supplement 12C*:190, Abstract L402 (1988).
Ehrlich, K.C. et al., "Identification and cloning of second phytase gene (phyB) from *Aspergillus niger* (*ficuum*)," *Biochem. Biophys. Res. Comm.* 195(1):53–57 (Aug. 1993).
Elliott, S. et al., "Isolation and Characterization of the Structural Gene for Secreted Acid Phosphatase from *Schizosaccharomyces pombe*," *J. Biol. Chem.* 261(6):2936–2941 (1986).
Fujiwara, S. et al., "Hydrolysis of phytate in soybean by phytase from Rhizopus sp. EF–78," *Chem. Abstr.* 106:266, Abstract No. 115629m (1987).
Grareib, M. et al., "Isolation and Characterization of Intracellular Phytase from *Macrophomina phaseolina*," *Zentralbl. Mikrobiol.* 143:397–403 (1988).
Gibson, D.M., "Production of Extracllular Phytase from *Aspergillus ficuum* on Starch Media," *Biotechnol. Letts.* 9(5):305–310 (1987).
Gibson, D.M. and A.B.J. Ullah, "Phytases and Action on Phytic Acid," Chapter 6 in: *Inositol Metabolism in Plants*, Morré, D.J. et al., eds, pp. 77–92, Wiley–Liss, pub., New York (1990).
Hayakawa, T. et al., "Purification and Characterization of Acid Phosphatases with or without Phytase Activity from Rice Bran," *Agric. Biol. Chem.* 53(6):1475–1783 (1989).
Himeno, M. et al., "Isolation and sequencing of cDNA clone encoding acid phosphatase in rat liver lysosomes," *Biochem. Biophys Res. Comm.* 162(3):1044–1053 (1989).
Houston, C.S. et al., "The Cloning and Overexpression of Phytase and pH 2.5 Acid Phosphatase in *Aspergillus niger*: Applications to a Commerical Product," presented at Society for Industrial Microbiology annual, San Diego, CA, Aug. 9–14, 1992.
Innis, M.A. et al., "Expression, Glycosylation, and Secretion of an Aspergillus Glucoamylase by *Saccharomyces cerevisiae*," *Science* 228:21–26 (1985).
MacRae, W.D. et al., "A phosphate–repressible acid phophatase gene from *Aspergillus niger*: its cloning, sequencing and transcriptional analysis," *Gene* 71:339–348 (1988).

(List continued on next page.)

*Primary Examiner*—Eric Grimes
*Attorney, Agent, or Firm*—Sterne, Kessler, Goldstein, & Fox P.L.L.C.

[57] ABSTRACT

The present invention provides a nucleic acid molecule encoding a phytase. The present invention also provides a nucleic acid molecule encoding a pH 2.5 acid phosphatase. Also provided are vectors, host cells, and a method of overexpressing phytate degrading enzymes.

91 Claims, 21 Drawing Sheets

OTHER PUBLICATIONS

"Microbial Phytase to be Used in Food Processing," *European Biotechnology Newsletter* 75:05 (18 Sep. 1989).

Mullaney, E.J. et al., "Positive idenitication of a lambda gt11 clone containing a region of fungal phytase gene by immunoprobe and sequence verification," *Appl. Microbiol. Biotechnol.* 35:611–614 (Aug. 1991).

Nayini, N.R. and P. Markakis, "The Phytase of Yeast," *Lebensm.–Wiss. u. –Technol.* 17:24–26 (1984).

Nevalainen, K.M.H. et al., "The Molecular Biology of Trichoderma and Its Application to the Expression of Both Homologus and Heterologous Genes," Chapter 6 in: *Molecular Industrial Mycology: Systems and Application for Filamentous Fungi*, Leoug, S.A. and R.M. Berka, eds., Marcel Dekker, Inc., pub., New York (Feb. 1991).

Ohtsuka, E. et al., "An Alternative Approach to Deoxyoligonucleotides as Hybridization Probes by Insertion of Deoxyinosine at Ambiguous Cohon Positions," *J. Biol. Chem.* 260(6):2605–2608 (1985).

Penttilä, M. et al., "A versatile transformation system for the cellulolytic filamentous fungus Trichoderma reesei," *Gene* 61:155–164 (1987).

Powar, V.K. and V. Jagannathan, "Purification and Properties of Phytate–Specific Phosphatase from Bacillus subtilis," *J. Bacteriol.* 151(3):1102–1108 (1982).

Rambosek, J. and J. Leach, "Recombinant DNA in Filamentous Fungi: Progress and Prospects," *CRC Critical Reviews in Biotechnology* 6(4):357–393 (1987).

Saloheimo, M. and M.–L. Niku–Paavola, "Heterologous Production of a Ligninolytic Enzyme: Expression of the Phlebia radiata Laccase Gene in Trichoderma reesei," *Bio/Technol.* 9:987–990 (Oct. 1991).

Shieh, T.R. and J.H. Ware, "Survey of Microoganisms for the Production of Extracellular Phytase," *Appl. Microbiol.* 16(9):1348–1351 (1968).

Ullah, A.H.J. and D.M. Gibson, "Extracllular Phytase (E.C. 3.1.3.8) from Aspergillus ficuum NRRL 3135: Purification and Characterization," *Prep. Biochem.* 17(1):63–91 (1987).

Ullah, A.H.J. and B.J. Cummins, "Purification, N–Terminal Amino Acid Sequence and Characterization of pH 2.5 Optimum Acid Phosphatase (E.C. 3.1.3.2.) from Asperillus ficuum," *Prep. Biochem.* 17(4):397–422 (1987).

Ullah, A.H.J. and B.J. Cummins, "Aspergillus ficuum Extracellular pH 6.0 Optimum Acid Phosphatase: Purification, N–Terminal Amino Acid Sequence, and Biochemical Characterization," *Prep. Biochem.* 18(1):37–65 (1988).

Ullah, A.H.J., "Aspergillus ficuum Phytase: Partial Primary Structure, Substrate Selectivity, and Kinetic Characterization," *Prep. Biochem.* 18(4):459–471 (1988).

Ullah, A.H.J., "Production, Rapid Purification and Catalytic Characterization of Extracellular Phytase from Aspergillus ficuum," *Prep. Biochem.* 18(4):443–458 (1988).

Ullah, A.H.J. and B.Q. Phillippy, "Immobilization of Aspergillus ficum Phytase: Product Characterization of the Bioreactor," *Prep. Biochem.* 18(4):483–489 (1988).

Ullah, A.H.J. and H.C. Dischinger, Jr. "Aspergillus ficuum Extracellular Phytase: Peptide mapping and Purification by Reverse Phase Chromatography," *Ann. New York Acad. Sci.* 613:878–882 (1990).

Uusitalo, J.M. et al., "Enzyme production by recombinant Trichoderma reesei strains," *J. Biotechnol.* 17:35–50 (Jan. 1991).

Yamada, K. et al., "Phytase from Aspergillus terreus: Part I. Production, Purification and Some General Properties of the Enzyme," *Agr. Biol. Chem.* 32(10):1275–1282 (1968).

Yamamoto, S. et al., "Chemical and Physicochemical Properties of Phytase from Aspergillus terreus," *Agr. Biol. Chem.* 36(12):2097–2103 (1972).

Youssef, K.A. et al., "Purification and General Properties of Extracllular Phytase from Aspergillus flavipes," *Zentralbl. Mikrobiol.* 142:397–402 (1987).

Dialog File 16, "Strategic Partners Report," *Genetic Technology News* (Oct. 1991).

Dialog File 583, "Collaborative research gains bio–tecnology break through," *International Milling Flour & Feed (IMFF)*, Informat No. 04630360, p. 6 (Oct. 1991).

van Hartingsveldt, W. et al., "Cloning, characterization and overexpression of the phytase–encoding gene (phyA) of Aspergillus niger," *Gene* 127:87–94 (May 1993).

Peptide #816:   Arg His Gly Glu Arg Tyr Pro Ser Pro Ser Ala

Oligo PHY-31    3' -GTG CCG CTC GCI ATG GG- 5'
                     A   A   T T       A
                     T
                     C Peptide #1110:  Gln Leu Pro Gln Phe Lys Oligo PHY-34    5'- CAA CTG CCG CAA TTT AA -3'
                        G   A   A   G   C
                        T   T
                        C   C Oligo PHY-35    5'- CAA TTA CCG CAA TTT AA -3'
                        G   G   A   G   C
                                T
                                C

FIG. 1

```
>Sph1
   1  GCATGCTGGA CCGGCAATCTC CGATCGCCGG GTATAAAAGG TCCTCCAAAC CCCTCTCGGT CGATATGTAC CCCGCTCGTC ATCTCCAATC CTCTGGAGAG

101  CACCTTCTCC AGCTTTGTC AATTGTACCT TCGCAATGCC TGCAACTCT CTCCTCACCC TGGCCTGTGC TCTGGCCACG GGCGCATCCG CTTTCTCCTA
                                                        M   P   R   T   S   L   L   T   L   A   C   A   L   A   T   G   A   S   A   F   S   Y >

201  CGGCGCTGCC ATTCCTCAGT CAACCCAGGA GAAGCAGTTC TCTCAGGAGT CCAAGCACT CTACAGCATC CTCAAGCACT ACGGTGGTAA CGGACCCTAC
       G   A   A   I   P   Q   S   T   Q   E   K   Q   F   S   Q   E   F   R   D   G   Y   S   I   L   K   H   Y   G   G   N   G   P   Y >

301  TCCGAGCGTG TGTCCTACGG TATCGCTCGC GATCCCCCGA CCAGCTGCGA GGTCGATCAG GTCATCATGG TCAAGGGTCA CGGAGAGCGC TACCGTCCC
       S   E   R   V   S   Y   G   I   A   R   D   P   P   T   S   C   E   V   D   Q   V   I   M   V   K   R   H   G   E   R   Y   P   S >

401  CTTCAGCCGG CAAGGACATC GAAGAGGCCC TGGCCAAGGT CTACAGCATC AACACTACTG AATACAAGGG CGACCTGGCC TTCCTGAACG ACTGGACCTA
       P   S   A   G   K   D   I   E   E   A   L   A   K   V   Y   S   I   N   T   T   E   Y   K   G   D   L   A   F   L   N   D   W   T   Y >

501  CTACGTCCCT AATGAGTGCT ACTACAACGC CGAGACCACC AGCGGCCCCT ACGCGGGTTT GCTGGACGCG TACAACCATG GCAACGATTA CAAGGCTCGC
       Y   V   P   N   E   C   Y   Y   N   A   E   T   T   S   G   P   Y   A   G   L   L   D   A   Y   N   H   G   N   D   Y   K   A   R >

601  TACGGCCACC TCTGGAACGG TGAGACGGTC GTGCCCTTCT TTTCTAGTGG CTACGGACGT GTCATCGAGA CGGCCCGCAA GTTCGGTGAG GGTTTCTTTG
       Y   G   H   L   W   N   G   E   T   V   V   P   F   F   S   S   G   Y   G   R   V   I   E   T   A   R   K   F   G   E   G   F   F >

701  GCTACAACTA CTCCACCAAC GCTGCCCTCA ACATCATCTC CGAGTCCGAG GTCATGGGCG CGGACAGCCT CACGCCCACC TGTGACACCG ACAACGACCA
       G   Y   N   Y   S   T   N   A   A   L   N   I   I   S   E   S   E   V   M   G   A   D   S   L   T   P   T   C   D   T   D   N   D   Q >

801  GACCACCTGC GACAACCTGA CTTACCAGCT GCCCCAGTTC AAGGTCGCTG CTGCCCGCCT AAACTCCCAG AACCCCGGCA TGAACCTCAC CGCATCTGAT
       T   T   C   D   N   L   T   Y   Q   L   P   Q   F   K   V   A   A   A   R   L   N   S   Q   N   P   G   M   N   L   T   A   S   D >
```

```
1701  TAGCCCTATT GCCTGCCAGG AGGGTGATGC TATGGACTAG ATGCAGAGGG GTAGGTCCCG GGATACTTTA GTGATGATTG ATATTCAAGT TTGGTGGTGA
        S  P  I    A  C  Q    E  G  D    A  M  D   *>

1801  CGATCACCTT GTTAATAGTC TTGTACAGTC ATACGGTGAA TGTAAATAAT GATAATAGCA ATGATACATG TTGGAATCTC GTTTTGTTCT TTGTGTGCAT

1901  AGGGGCTTTG GGGGTGTATT TTTAGGCGTT AGACTTATTT TCAATTCGTG TATAATGCGG TCAGTAAATG AATCATCAAT TATTCAAATG CAATGCTGTA
                                                                                  >Sph1
                                                                                  ^
2001  TACGTGAAAC TATTGGGTTA AGACGCAGCT ACTAGCTGAC TGCTTGGTTA CTTTCTGTGT ACACCGCATG C
```

FIG.2C

Peptide #792

```
 1   2   3   4   5   6   7   8   9  10  11  12
Tyr Tyr Gly His Gly Ala Gly Asn Pro Leu Gly Pro -
```

Oligonucleotide 1

```
TAT TAT GGT CAT GGT GC
  C   C   C   C   C
          G       G
          A       A
```

```
13  14  15  16  17  18  19  20  21  22  23  24
-  Thr Gln Gly Val Gly Tyr Ala Asn Glu Leu Ile Ala
```

Oligonucleotide 2

```
CAA GGT GTT GGT TAT GC
  G   C   C   C   C
      G   G   G
      A   A   A
```

Peptide #420

```
 1   2   3   4   5   6    7    8   9   10
Leu Tyr Val Glu Met Met Gln (Asn) Gln Ala (Glu)
```

```
12   13   14  15  16
Gln (Thr) Pro Leu Val
```

Oligonucleotide 3

```
TAT GTT GAA ATG ATG CAA AA
  C   C   G           G
      G
      A
```

Oligonucleotide 4

ATG ATG CAA AAT CAA GCT GAA CA

FIG. 3

```
CATCCAGGCA CCCTTTCCCA ACGGGGGAAC TTCCGTTGTC CACGTGCCCT GGTTCAGCCA          60

ATCAAAGCGT CCCACGGCAA TGCTGGATCA ACGATCAACT TGAATGCAAT AAATGAAGAT         120

GCAACTAACA CCATCTGTTG CCTTTCTCTC GAGAAAGCTC CTCCACTTCT CACACTAGAT         180

TTATCCGTTC CTTGTCGACT TCCCGTCCCA TTCGGCCTCG TCCACTGAAG ATCTATCCCA         240

CCATTGCACG TGGGCCACCT TTGTGAGCTT CTAACCTGAA CTGGTAGAGT ATCACACAAC         300

ATGCGAAAGT GGGATGAAGG GGTTATATGA GGACCGTCCG GTCCGGCGCG ATGGCCGTAG         360

CTGCCAATCG CTGCTGTGCA AGAAATTTCT TCTCATAGGC ATC ATG GGC GTC TCT          415
                                                Met Gly Val Ser

GCT GTT CTA CTT CCT TTG TAT CTC CTA GCT  GG  GTATGCTAAG CACCGCTATC       467
Ala Val Leu Leu Pro Leu Tyr Leu Leu Ala  Gl
-15              -10              -5

TAAGTCTGAT AAGGACCCTC TTTGCCGAGG GCCCCTGAAG CTCGGACTGT GTGGGACTAC         527

TGATCGCTGA CAATCTGTGC AG A GTC ACC TCC GGA CTG GCA GTC CCC GCC TCG       580
                       y Val Thr Ser Gly Leu Ala Val Pro Ala Ser
                                     1                   5

AGA AAT CAA TCC ACT TGC GAT ACG GTC GAT CAA GGG TAT CAA TGC TTC          628
Arg Asn Gln Ser Thr Cys Asp Thr Val Asp Gln Gly Tyr Gln Cys Phe
              10                  15                  20

TCC GAG ACT TCG CAT CTT TGG GGT CAA TAC GCG CCG TTC TTC TCT CTG          676
Ser Glu Thr Ser His Leu Trp Gly Gln Tyr Ala Pro Phe Phe Ser Leu
          25                  30                  35

GCA AAC GAA TCG GCC ATC TCC CCT GAT GTG CCC GCC GGT TGC AGA GTC          724
Ala Asn Glu Ser Ala Ile Ser Pro Asp Val Pro Ala Gly Cys Arg Val
      40                  45                  50

ACT TTC GCT CAG GTC CTC TCC CGT CAT GGA GCG CGG TAT CCG ACC GAG          772
Thr Phe Ala Gln Val Leu Ser Arg His Gly Ala Arg Tyr Pro Thr Glu
55                  60                  65                  70

TCC AAG GGC AAG AAA TAC TCC GCT CTC ATT GAG GAG ATC CAG CAG AAC          820
Ser Lys Gly Lys Lys Tyr Ser Ala Leu Ile Glu Glu Ile Gln Gln Asn
                75                  80                  85
```

FIG.5A

| | |
|---|---|
| GTG ACC ACC TTT GAT GGA AAA TAT GCC TTC CTG AAG ACA TAC AAC TAC<br>Val Thr Thr Phe Asp Gly Lys Tyr Ala Phe Leu Lys Thr Tyr Asn Tyr<br>                90                            95                      100 | 868 |
| AGC TTG GGT GCA GAT GAC CTG ACT CCC TTC GGA GAG CAG GAG CTA GTC<br>Ser Leu Gly Ala Asp Asp Leu Thr Pro Phe Gly Glu Gln Glu Leu Val<br>            105                       110                     115 | 916 |
| AAC TCC GGC ATC AAG TTC TAC CAG CGA TAC GAA TCG CTC ACA AGG AAC<br>Asn Ser Gly Ile Lys Phe Tyr Gln Arg Tyr Glu Ser Leu Thr Arg Asn<br>        120                     125                      130 | 964 |
| ATC ATT CCG TTC ATC CGA TCC TCT GGC TCC AGC CGC GTG ATC GCC TCC<br>Ile Ile Pro Phe Ile Arg Ser Ser Gly Ser Ser Arg Val Ile Ala Ser<br>135                  140                     145                 150 | 1012 |
| GGC GAG AAA TTC ATT GAG GGC TTC CAG AGC ACC AAG CTG AAG GAT CCT<br>Gly Glu Lys Phe Ile Glu Gly Phe Gln Ser Thr Lys Leu Lys Asp Pro<br>                 155                     160                     165 | 1060 |
| CGT GCC CAG CCG GGC CAA TCG TCG CCC AAG ATC GAC GTG GTC ATT TCC<br>Arg Ala Gln Pro Gly Gln Ser Ser Pro Lys Ile Asp Val Val Ile Ser<br>            170                     175                     180 | 1108 |
| GAG GCC AGC TCA TCC AAC AAC ACT CTC GAC CCA GGC ACC TGC ACT GTC<br>Glu Ala Ser Ser Ser Asn Asn Thr Leu Asp Pro Gly Thr Cys Thr Val<br>               185                     190                     195 | 1156 |
| TTT GAA GAC AGC GAA TTG GCC GAT ACC GTC GAA GCC AAT TTC ACC GCC<br>Phe Glu Asp Ser Glu Leu Ala Asp Thr Val Glu Ala Asn Phe Thr Ala<br>      200                     205                     210 | 1204 |
| ACG TTC GCC CCC TCC ATT CGT CAA CGT CTG GAG AAC GAC CTG TCT GGC<br>Thr Phe Ala Pro Ser Ile Arg Gln Arg Leu Glu Asn Asp Leu Ser Gly<br>215                  220                     225                 230 | 1252 |
| GTG ACT CTC ACA GAC ACA GAA GTG ACC TAC CTC ATG GAC ATG TGC TCC<br>Val Thr Leu Thr Asp Thr Glu Val Thr Tyr Leu Met Asp Met Cys Ser<br>               235                     240                     245 | 1300 |
| TTC GAC ACC ATC TCC ACC AGC ACC GTC GAC ACC AAG CTG TCC CCC TTC<br>Phe Asp Thr Ile Ser Thr Ser Thr Val Asp Thr Lys Leu Ser Pro Phe<br>                 250                     255                     260 | 1348 |
| TGT GAC CTG TTC ACC CAT GAC GAA TGG ATC CAC TAC GAC TAC CTC CAG<br>Cys Asp Leu Phe Thr His Asp Glu Trp Ile His Tyr Asp Tyr Leu Gln<br>            265                     270                     275 | 1396 |

FIG.5B

```
TC  CTG AAA AAA TAC TAC GGC CAT GGC GCA GGT AAC CCG CTC GGC CCG              1444
Ser Leu Lys Lys Tyr Tyr Gly His Gly Ala Gly Asn Pro Leu Gly Pro
    280             285                 290

ACC CAG GGC GTC GGC TAC GCT AAC GAG CTC ATC GCC CGT CTC ACC CAC              1492
Thr Gln Gly Val Gly Tyr Ala Asn Glu Leu Ile Ala Arg Leu Thr His
295             300                 305                 310

TCG CCT GTC CAC GAT GAC ACC AGC TCC AAC CAC ACC TTG GAC TCG AAC              1540
Ser Pro Val His Asp Asp Thr Ser Ser Asn His Thr Leu Asp Ser Asn
            315                 320                 325

CCA GCT ACC TTC CCG CTC AAC TCT ACT CTC TAC GCG GAC TTT TCC CAC              1588
Pro Ala Thr Phe Pro Leu Asn Ser Thr Leu Tyr Ala Asp Phe Ser His
        330                 335                 340

GAT AAC GGC ATC ATC TCT ATC CTC TTT GCT TTG GGT CTG TAC AAC GGC              1636
Asp Asn Gly Ile Ile Ser Ile Leu Phe Ala Leu Gly Leu Tyr Asn Gly
            345                 350                 355

ACT AAG CCG CTG TCT ACC ACG ACC GTG GAG AAT ATC ACC CAG ACA GAT              1684
Thr Lys Pro Leu Ser Thr Thr Thr Val Glu Asn Ile Thr Gln Thr Asp
    360                 365                 370

GGG TTC TCG TCT GCT TGG ACG GTT CCG TTT GCT TCG CGT CTG TAC GTC              1732
Gly Phe Ser Ser Ala Trp Thr Val Pro Phe Ala Ser Arg Leu Tyr Val
375             380                 385                 390

GAG ATG ATG CAG TGC CAG GCC GAG CAG GAG CCG CTG GTC CGT GTC TTG              1780
Glu Met Met Gln Cys Gln Ala Glu Gln Glu Pro Leu Val Arg Val Leu
                395                 400                 405

GTT AAT GAT CGC GTT GTC CCG CTG CAT GGG TGT CCA ATT GAT GCT TTG              1828
Val Asn Asp Arg Val Val Pro Leu His Gly Cys Pro Ile Asp Ala Leu
            410                 415                 420

GGG AGA TGT ACC CGG GAT AGC TTT GTG AGG GGG TTG AGC TTT GCT AGA              1876
Gly Arg Cys Thr Arg Asp Ser Phe Val Arg Gly Leu Ser Phe Ala Arg
            425                 430                 435

TCT GGG GGT GAT TGG GCG GAG TGT TCT GCT TAGCTGAACT ACCTTGATGG                1926
Ser Gly Gly Asp Trp Ala Glu Cys Ser Ala
            440                 445

ATGGTATGTA TCAATCAGAG TACATATCAT TACTTCATGT ATGTATTTAC GAAGATGTAC            1986
```

FIG.5C

```
ATATCGAAAT ATCGATGATG ACTACTCCGG TAGATATTTG GTCCCCTTCT ATCCTTCGTT    2046

CCACAACCAT CGCACTCGAC GTACAGCATA ATACAACTTC AGCATTAACA AACGAACAAA    2106

TAATATTATA CACTCCTCCC CAATGCAATA ACAACCGCAA TTCATACCTC ATATAGATAC    2166

AATACAATAC ATCCATCCCT ACCCTCAAGT CCACCCATCC CATAATCAAA TCCCTACTTA    2226

CTCCTCCCCC TTCCCAGAAC CCACCCCCGA AGGAGTAATA GTAGTAGTAG AAGAAGCAGA    2286

CGACCTCTCC ACCAACCTCT TCGGCCTCTT ATCCCCATAC GCTATACACA CACGAACACA    2346

CCAAATAGTC AGCATGC
```

FIG.5D pALK171 FUSION

5'-primer (39-mer)

5'- C AA<u>C</u> <u>CGC</u> <u>GG</u>A CTG CGC ATC ATG GGC GTC TCT GCT GTT CT
   SacII 19 nts "tail" of cbh1  20 nts of the phytase signal sequence
   (promoter sequence)

3'-primer (22-mer)

5'- A TTT <u>CTC</u> <u>GAG</u> GCG GGG ACT GCC
    XhoI
   phytase sequence pALK172 FUSION 5'primer (46-mer)

5'- CTC <u>GGC</u> <u>CTT</u> <u>CTT</u> <u>GGC</u> <u>C</u>AC AGC TCG TGCT CTG GCA GTC CCC GCC TCG
     SfiI 28 nts "tail" of cbh1     18 nts of the phytase N-terminal
  (signal sequence)      sequence 3'-primer (24-mer)

5'-TTG GTG <u>TCG</u> <u>AC</u>G GTG CTG GTG GAG
    SalI
   phytase sequence

FIG. 6

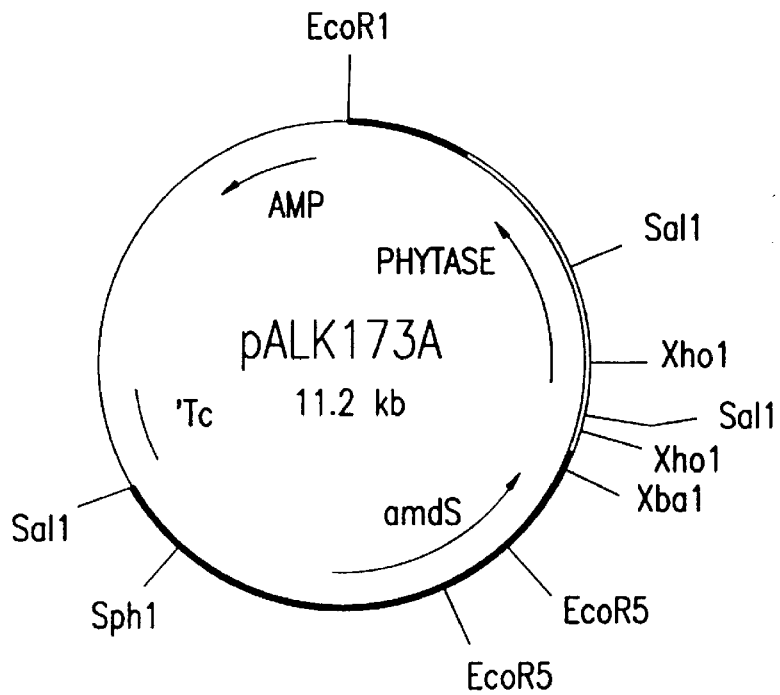
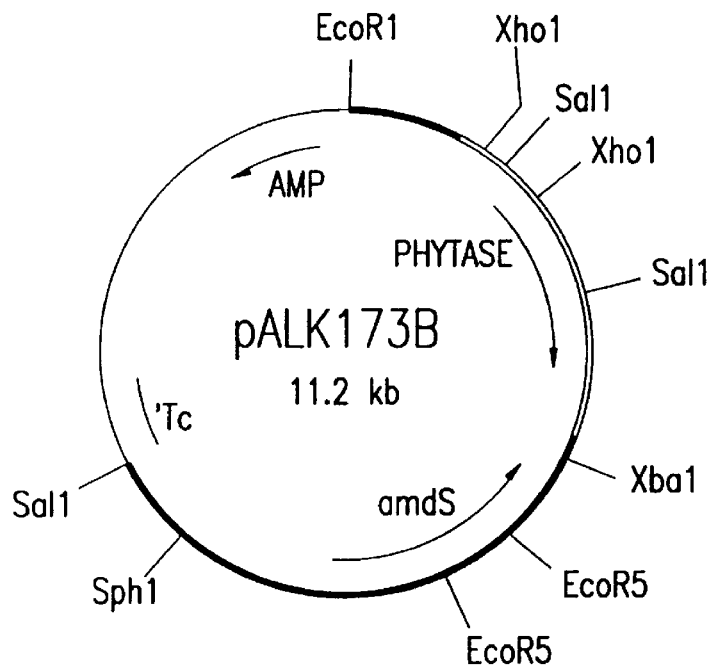
FIG.9 pALK532 FUSION

5'-PRIMER (46-mer)

5'-CTC GGC CTT CTT GGC CAC AGC TCG TGC TTT CTC CTA CGG CGC
TGC C       SfiI 28 nts tail of cbh1         18 nts OF THE ACID PHOSPHATASE
(SIGNAL SEQUENCE)      N-TERMINAL SEQUENCE 3'-PRIMER (30-mer)

5'-GCC ATG GTT GTA CGC GTC CAG CAA ACC GGC
               MluI
  pH 2.5 ACID PHOSPHATASE SEQUENCE pALK533 FUSION

5'-PRIMER (39-mer)

5'-CAA CCG CGG ACT GCG CAT CAT GCC TCG CAC CTC TCT CCT
     SacII 19 nts tail of cbh1         20 nts OF THE ACID PHOSPHATASE
(PROMOTER SEQUENCE)    SIGNAL SEQUENCE 3'-PRIMER (30-mer)

5'-GCC ATG GTT GTA CGC GTC CAG CAA ACC GGC
               MluI
  pH 2.5 ACID PHOSPHATASE SEQUENCE

FIG. 11

NUCLEIC ACID MOLECULES ENCODING PHYTASE AND PH2.5 ACID PHOSPHATASE

CROSS-REFERENCE TO RELATED APPLICATIONS

This application is a division of application Ser. No. 07/923,724, filed Jul. 31, 1992, which is a CIP of Ser. No. 07/496,155, filed Mar. 19, 1990, now U.S. Pat. No. 5,273,887, which is a continuation of Ser. No. 07/044,077, filed Apr. 29, 1987 (abandoned).

BACKGROUND OF THE INVENTION

The mesophilic filamentous fungus Trichoderma reesei is very efficient in secreting cellulase enzymes into the growth medium. In optimized cultivation conditions amounts, up to 40 g/l of extracellular cellulase have been reported (Durand et al., Enzyme Microb. Technol. 10:341–346 (1988); Durand et al., in Biochemistry and Genetics of Cellulose Degradation, Academic Press, 1988, pp. 135–151).

Development of transformation systems for T. reesei (Knowles et al., EP244,234; Penttilä et al., Gene 61:155–164 (1987); Berka et al., EP215,594) has made possible the application of genetic engineering methods to the fungus. By genetic engineering, production profiles of different cellulase enzymes have been modulated e.g., to give strains with improved levels of the endoglucanase I enzyme. The strong cbh1 promoter has been applied to promote endoglucanase expression (Nevalainen et al., "The molecular biology of Trichoderma and its application to the expression of both homologous and heterologous genes," in Molecular Industrial Mycology, Leong and Berka, eds., Marcel Dekker Inc., New York, pp. 129–148 (1991); and Harkki, A. et al., Enzyme Microb. Technol. 13:227–233 (1991)).

In addition to tailoring the production profiles of homologous proteins, the production potential of T. reesei has been harnessed to express various heterologous proteins in the fungus. So far examples are few and include e.g., calf chymosin (Knowles et al., EP244,234; Berka et al., EP215,594; Harkki, A. et al., Bio/Technol. 7:596–603 (1989); Uusitalo, J. M. et al., J. Biotechnol. 17:35–50 (1991)), CBH1-Fab fusion antibodies raised against 2-phenyl-oxazolone (Nyyssönen et al., WO92/01797) and a fungal ligninolytic enzyme (Saloheimo, M. and Niku-Paavola, M.-L. Bio/Technol. 9:987–990 (1991)). For improved expression the desired gene has been inserted into a cbh1 expression cassette and introduced into T. reesei by protoplast transformation (Harkki, A. et al., Bio/Technol. 7:596–603 (1989); Nyyssönen et al., WO92/01797; (Saloheimo, M. and Niku-Paavola, M.-L. Bio/Technol. 9:987–990 (1991)). Even though heterologous filamentous fungal promoters such as Aspergillus amdS, argB and glucoamylase (GA) can function in T. reesei at least to some extent (Penttilä et al., Gene 61:155–164 (1987); Knowles et al., EP244,234) efficient expression requires the use of a homologous promoter. In addition, better yields have been obtained in some cases by producing the desired gene product as a fusion protein (Harkki, A. et al., Bio/Technol. 7:596–603 (1989); Nyyssönen et al., WO92/01797). The yields of heterologous proteins obtained from T. reesei have varied between 10–150 mg/l.

Phytate, a storage form of phosphorus in plant seeds, is part of human and animal diets. Phytate phosphorus is poorly available to monogastrics, because it forms complexes with multivalent metal ions and binds to proteins. Thus degradation of phytate is of interest. Plant phytin degrading enzymes phytase and acid phosphatase for the conversion of phytate to inositol and inorganic phosphorus are produced e.g., by bacteria (Powar, V. K. and Jagannathan, V. J., J. Bacteriol. 15:1102–1108 (1982); Cosgrove, D. J.,Aust. J. Biol. Sci. 23:1207–1220 (1970) and Cosgrove, D. J. et al.,Aust. J. Biol. Sci. 23:339–343 (1970); yeasts (Nayini, N. R. and Markakis, P., Lebensmittel Wissenschaft und Technologie. 17:24–26 (1984)) and filamentous fungi comprising several Aspergillus species such as A. terreus (Yamada et al., Agric. Biol. Chem. 32:1275–1282 (1968), A. ficuum (Gibson, D. M. Biotechnol. Lett. 9:305–310 (1987) and A. niger (Shieh, T. R. and Ware, J. H., Appl. Microbiol. 16:1348–1351 (1968)). For complete degradation of plant phytin, both phytase and pH 2.5 acid phosphatase are needed.

Industrial applications involve remarkable higher production yields than the amounts produced by the natural reported strains. The gene coding for phytase has been recently isolated and characterized from A. ficuum (Van Gorcom et al., EP420,358 or WO91/05053) and the production of phytase has been improved in A. ficuum by multiplying the copy number of the gene in an expression cassette containing a strong homologous Aspergillus promoter e.g., GA (Van Gorcom et al., EP420,358 or WO91/05053). A gene coding for acid phosphatase has been isolated and characterized from A. niger, (MacRae et al., Gene 71:339–348 (1988)).

SUMMARY OF THE INVENTION

Recognizing the need for better production methods of phytase and pH2.5 acid phosphatase, and for compositions containing the same, the inventors have developed highly efficient methods for the recombinant production thereof.

According to the invention, there is first provided a method for overexpressing phytate degrading enzymes in Trichoderma.

There are further provided methods for overexpressing recombinant Aspergillus niger phytase and pH2.5 acid phosphatase enzymes in Trichoderma and secreting such enzymes therefrom.

There are further provided expression vectors containing genetic sequences encoding such enzymes, and Trichoderma host cells transformed with such expression vectors.

There are further provided compositions comprising one or more of the Trichoderma-synthesized, recombinant phytase-degrading enzymes of the invention.

There are further provided methods for the use of such compositions in feed and other such methods comprising food compositions, especially for animals.

BRIEF DESCRIPTION OF THE DRAWINGS

FIG. 1. Sequence of peptide #816 ([SEQ ID No. :57:]), oligo PHY-31 ([SEQ ID No. :64:]), peptide #1110 ([SEQ ID No. :62:]), oligo PHY-34 ([SEQ ID No. :65:]) and oligo PHY-35 ([SEQ ID No. :52:]). pH2.5 acid phosphatase oligonucleotide PHY-31 is a 17mer mixture with 64 fold degeneracy and a single inosine. Peptide #816 is derived from an endoproteinase Lys-C digestion of purified native acid phosphatase. PHY-34 is a 17mer mixture with 128 fold degeneracy. PHY-35 is a 17mer mixture with 64 fold degeneracy. Both PHY-34 and PHY-35 are necessary for complete representation of Peptide #1110. Peptide #1110 is derived from a trypsin digestion of purified native acid phosphatase.

FIGS. 2(A–C). Nucleotide sequence from the 2.1 kb SphI fragment containing the pH 2.5 acid phosphatase gene [SEQ ID No. :1:] with deduced amino acid translation [SEQ ID No. :2:]. The intron donor, lariat and acceptor sequence as determined by cDNA sequencing are overlined. The nucleotide sequence corresponding to peptides #816 ([SEQ ID No. :57:]) and #1110 ([SEQ ID No. :62:]) is underlined. The genomic nucleotide sequence was determined by the M13-dideoxy method (Sanger, F., et al., *Proc. Natl. Acad. Sci. USA* 74:5463–5467 (1977) with the use of the United States Biochemical Sequencase II kit.

FIG. 3. The amino acid sequences of the phytase tryptic peptides #792 [SEQ ID No. :43:] and #420 [SEQ ID No. :23:] and the deduced oligonucleotides [SEQ ID Nos. :3:, :4:, :5: and :6:] used in the production of the phytase probe by nested PCR amplification.

FIGS. 5(A–D). The nucleotide sequence of the phytase gene. [SEQ ID Nos. :7: (DNA) and :8: (amino acid)].

FIG. 6. The PCR primers used for making the cbh1-phytase fusion fragments [SEQ ID Nos. :9: and :10: and :11: and :12:].

FIG. 9. Plasmids pALK173A and pALK173B. The maps of the plasmids containing the phytase gene with its own promoter and the selection marker, amdS gene, are shown. In the plasmid, pALK173A the transcriptional orientation of the phytase and amdS genes is the same; and in the plasmid pALK173B, the transcriptional orientation of these two genes is opposite to each other.

FIG. 11. The PCR primers used for making the cbh1—pH 2.5 acid phosphatase fusion fragments [SEQ ID Nos. :13: and :14: and :15:].

DETAILED DESCRIPTION OF THE INVENTION

I. DEFINITIONS

Figure 4:
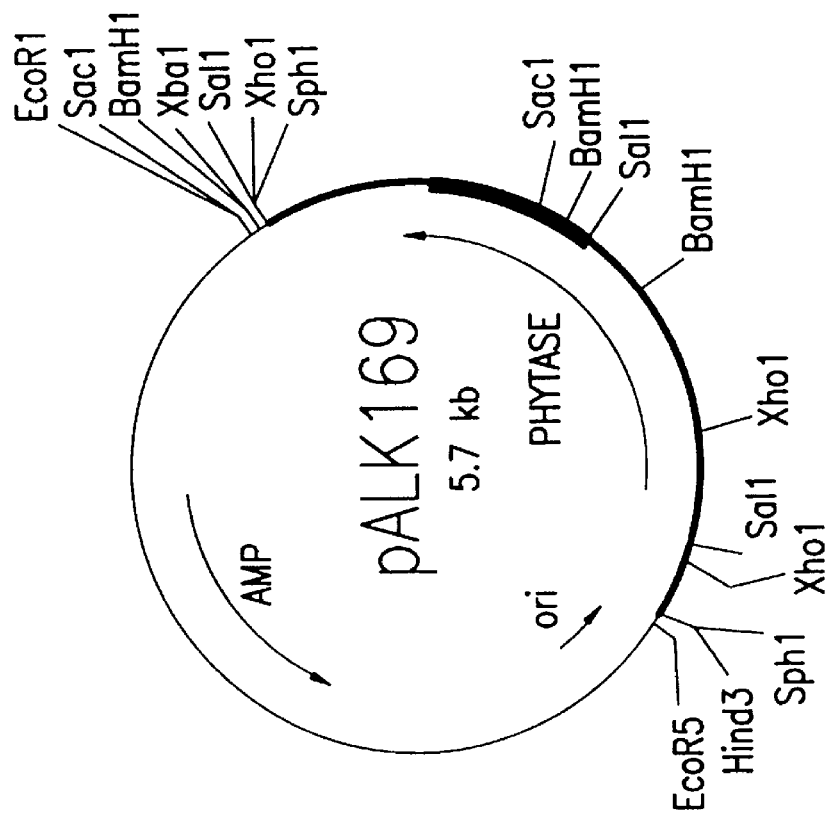
FIG. 4. Plasmid pALK169. The map of pALK169 containing the 2.4 kb SphI insert and showing the restriction map of the insert. The location of the phytase gene is shown by an arrow. The hybridization site for the 350 bp PCR fragment in the phytase sequence is shown by an intensified line.

In the description that follows, a number of terms used in recombinant DNA (rDNA) technology are extensively utilized. In order to provide a clear and consistent understanding of the specification and claims, including the scope to be given such terms, the following definitions are provided.

Gene. A DNA sequence containing a template for an RNA polymerase. The RNA transcribed from a gene may or may not code for a protein. RNA that codes for a protein is termed messenger RNA (mRNA) and, in eukaryotes, is transcribed by RNA polymerase II. A gene containing a RNA polymerase II template (as a result of a RNA polymerase II promoter) wherein an RNA sequence is transcribed which has a sequence complementary to that of a specific mRNA, but is not normally translated may also be constructed. Such a gene construct is herein termed an "antisense RNA gene" and such an RNA transcript is termed an "antisense RNA." Antisense RNAs are not normally translatable due to the presence of translational stop codons in the antisense RNA sequence.

A "complementary DNA" or "cDNA" gene includes recombinant genes synthesized by, for example, reverse transcription of mRNA, thus lacking intervening sequences (introns). Genes clones from genomic DNA may or may not contain introns.

Cloning vehicle. A plasmid or phage DNA or other DNA sequence which is able to carry genetic information, specifically DNA, into a host cell. A cloning vehicle is often characterized by one or a small number of endonuclease recognition sites at which such DNA sequences may be cut in a determinable fashion without loss of an essential biological function of the vehicle, and into which a desired DNA may be spliced in order to bring about its cloning into the host cell. The cloning vehicle may further contain a marker suitable for use in the identification of cells transformed with the cloning vehicle, and origins of replication that allow for the maintenance and replication of the vehicle in one or more prokaryotic or eukaryotic hosts. Markers, for example, are tetracycline resistance or ampicillin resistance. The word "vector" is sometimes used for "cloning vehicle." A "plasmid" is a cloning vehicle, generally circular DNA, that is maintained and replicates autonomously in at least one host cell.

Expression vehicle. A vehicle or vector similar to a cloning vehicle but which supports expression of a gene that has been cloned into it, after transformation into a host. The cloned gene is usually placed under the control of (i.e., operably linked to) certain control sequences such as promoter sequences, that may be provided by the vehicle or by the recombinant construction of the cloned gene. Expression control sequences will vary depending on whether the vector is designed to express the operably linked gene in a prokaryotic or eukaryotic host and may additionally contain transcriptional elements such as enhancer elements (upstream activation sequences) and termination sequences, and/or translational initiation and termination sites.

Host. A host is a cell, prokaryotic or eukaryotic, that is utilized as the recipient and carrier of recombinant material.

Eukaryotic host. A "eukaryotic host" may be any cell from a eukaryotic organism, including, for example, animal, plant, fungi and yeast.

Host of the Invention. The "host of the invention" is a filamentous fungus host that has been engineering to produce recombinant phytase and/or pH 2.5 acid phosphatase according to the methods of the invention.

Functional Derivative. A "functional derivative" of a protein or nucleic acid, is a molecule that has been chemically or biochemically derived from (obtained from) such protein or nucleic acid and which retains a biological activity (either functional or structural) that is a characteristic of the native protein or nucleic acid. The term "functional derivative" is intended to include "fragments," "variants," "analogues," or "chemical derivatives" of a molecule that retain a desired activity of the native molecule.

As used herein, a molecule is said to be a "chemical derivative" of another molecule when it contains additional chemical moieties not normally a part of the molecule. Such moieties may improve the molecule's solubility, absorption, biological half life, etc. The moieties may decrease the toxicity of the molecule, or eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

Fragment. A "fragment" of a molecule such as a protein or nucleic acid is meant to refer to a portion of the native amino acid or nucleotide genetic sequence, and in particular the functional derivatives of the invention.

Variant or Analog. A "variant" or "analog" of a protein or nucleic acid is meant to refer to a molecule substantially similar in structure and biological activity to either the native molecule, such as that encoded by a functional allele.

II. THE HOSTS OF THE INVENTION

*T. reesei* does not produce endogenous phytase. Instead, other enzyme components such as β-glucan degrading activity, important in e.g. feed applications, are produced in high amounts. Thus the use of *T. reesei* as a production host for fungal phytase and pH 2.5 acid phosphatase results in secretion of a totally different enzyme composition when compared to that secreted from Aspergillus. In addition, by using Trichoderma as a source of a composition containing phytase degrading enzymes, some difficult problems in downstream processing that occur with similar Aspergillus compositions (e.g., in filtration) are avoided. This is because the mode of growth of the recombinant *T. reesei* is different than that of Aspergilli, the mycelium being most often fluid and easily separable. Thus, by producing these enzymes in the hosts of the invention, no problems in subsequent filtration of the secreted material is seen, as is the case with the often slimy and thick mycelium of Aspergilli.

Improved amounts of phytase and pH 2.5 acid phosphatase (as compared to synthesis in Aspergillus) can be produced in the *T. reesei* expression system by inserting a DNA sequence obtained from *A. niger*, coding for phytase or pH 2.5 acid phosphatase activity, into a *T. reesei* expression cassette containing the cbh1 promoter and the Aspergillus amdS gene as a transformation marker. Transformation of the construct to *T. reesei* hosts results in stable transformants expressing the phytase or pH 2.5 acid phosphatase in high amounts in a novel background of accompanying enzyme activities.

The mixture produced by *T. reesei* contains high β-glucanase activity and low glucoamylase activity. Moreover, the amount of phytase produced by recombinant *T. reesei* strains in shake flask cultivations is comparable to the level of which the main cellulase, the endogenous cellobiohydrolase I, is expressed. The amount of the pH 2.5 acid phosphatase produced by the recombinant strains in shake flask cultivations is less than 0.5 g/l.

*Aspergillus niger* var. awamori ALKO 243 (ATCC 38854) (IFO4033) phytase and acid phosphatase (optimum pH 2.5) were overexpressed in *Trichoderma reesei* under the control of the Trichoderma cellobiohydrolase 1 (cbh1) promoter. In addition, the phytase gene was expressed from its own promoter.

For both the genes, two constructions utilizing the cbh1 promoter were made: in one construction the phytase or acid phosphatase signal sequence was used and in the other construction the cbh1 signal sequence was used. In all cases, the fusions were made precise by using PCR and the plasmids were constructed so that the expression cassette could be separated from the vector backbone prior to transformations. Thus it was possible to transform strains with only the desired sequences (and not the entire vector used for maintaining the sequences) and thus to obtain strains that did not contain any "foreign" sequences; such strains were suitable for industrial purposes.

Three *Trichoderma reesei* strains, ATCC 56765 (RutC-30), ALKO 233 (VTT-D-79125) and a low aspartyl protease producing strain ALKO 2221 were used as hosts for phytase expression. For acid phosphatase expression, only *T. reesei* ALKO 2221 was transformed. When phytase was expressed under the cbh1 promoter in Trichoderma, the best transformation with no *E. coli* sequences produced in shake flask cultivations about 3,600 fold more phytase than the non-transformed *A. niger* ALKO 243. When the phytase promoter was used, the best yield obtained in shake flask cultivations of *T. reesei* transformants was about 120 fold that obtained with *A. niger* ALKO 243. The best acid phosphatase activities obtained were about 240 fold higher compared to the levels produced by the *A. niger* ALKO 243 strain.

The molecular weights (in SDS-PAGE) of the phytase and pH 2.5 acid phosphatase secreted by Trichoderma were different from those secreted by Aspergillus. The difference seemed to be due to different glycosylation.

The production level of phytase obtained when the Aspergillus gene was expressed in Trichoderma under the control of a Trichoderma promoter was surprisingly high.

The use of *T. reesei* as a production host for fungal phytase and pH 2.5 acid phosphatase results in totally different enzyme preparations as compared to that from Aspergillus. When compared to Aspergillus preparations, the mixtures produced by *T. reesei* contain substantially higher β-glucanase and proportionally lower glucoamylase activities thus making *T. reesei* preparations preferable to be used e.g. in animal feed.

The hosts of the invention are meant to include all Trichoderma. Trichoderma are classified on the basis of morphological evidence of similarity. *T. reesei* was formerly known as *T. viride* Pers. or *T. koningii* Oudem; sometimes it was classified as a distinct species of the *T. longibrachiatum* group. The entire genus Trichoderma, in general, is characterized by rapidly growing colonies bearing tufted or pustulate, repeatedly branched conidiophores with lageniform phialides and hyaline or green conidia borne in slimy heads (Bissett, J., Can. J. Bot. 62:924–931 (1984)).

The fungus called *T. reesei* is clearly defined as a genetic family originating from the strain QM6a, that is, a family of strains possessing a common genetic background originating from a single nucleus of the particular isolate QM6a. Only those strains are called *T. reesei*.

Classification by morphological means is problematic and the first recently published molecular data from DNA-fingerprint analysis and the hybridization pattern of the cellobiohydrolase-2 (cbh2) gene in *T. reesei* and *T. longibrachiatum* clearly indicates a differentiation of these strains (Meyer, W. et al., *Curr. Genet.* 21:27–30 (1992); Morawetz, R. et al., *Curr. Genet.* 21:31–36 (1992)).

However, there is evidence of similarity between different Trichoderma species at the molecular level that is found in the conservation of nucleic acid and amino acid sequences of macromolecular entities shared by the various Trichoderma species. For example, Cheng, C., et al., *Nucl. Acids. Res.* 18:5559 (1990), discloses the nucleotide sequence of *T. viride* cbh1. The gene was isolated using a probe based on the *T. reesei* sequence. The authors note that there is a 95% homology between the amino acid sequences of the *T. viride* and *T. reesei* gene. Goldman, G. H. et al., *Nucl. Acids Res.* 18:6717 (1990), discloses the nucleotide sequence of phosphoglycerate kinases from *T. viride* and notes that the deduced amino acid sequence is 81% homologous with the phosphoglycerate kinase gene from *T. reesei*. Thus, the species classified to *T. viride* and *T. reesei* must genetically be very close to each other.

In addition, there is a high similarity of transformation conditions among the Trichoderma. Although practically all the industrially important species of Trichoderma can be found in the formerly discussed Trichoderma section Longbrachiatum, there are some other species of Trichoderma that are not assigned to this section. Such a species is, for example, *Trichoderma harzianum*, which acts as a biocontrol agent against plant pathogens. A transformation system has also been developed for this Trichoderma species (Herrera-Estrella, A. et al., *Molec. Microbiol.* 4:839–843 (1990), that is essentially the same as that taught in the application. Thus, even though *Trichoderma harzianum* is not assigned to the section Longibrachiatum, the method used by Herrera-Estrella in the preparation of spheroplasts before transformation is the same. The teachings of Herrera-Estrella show that there is not a significant diversity of Trichoderma spp. such that the transformation system of the invention would not be expected to function in all Trichoderma.

Further, there is a common functionality of fungal transcriptional control signals among fungal species. At least three *A. nidulans* promoter sequences, amdS, argB, and gpd, have been shown to give rise to gene expression in *T. reesei*. For amdS and argB, only one or two copies of the gene are sufficient to being about a selectable phenotypes (Penttilä et al., *Gene* 61:155–164 (1987), Gruber, F. et al., *Curr. Genetic* 18:71–76 (1990) also notes that that fungal genes can often be successfully expressed across different species.

Many species of Trichoderma are available from a wide variety of resource centers that contain fungal culture collections. In addition, Trichoderma species are catalogued in various databases. These resources and databases are summerized by O'Donnell, K. et al., in *Biochemistry of Filamentous Fungi: Technology and Products*, D. B. Finkelstein et al., eds., Butterworth-Heinemann, Stoneham, Mass., USA, 1992, pp. 3–39.

III. CONSTRUCTION OF THE HOSTS OF THE INVENTION

The process for genetically engineering the hosts of the invention, according to the invention, is facilitated through the isolation and partial sequencing of pure protein encoding an enzyme of interest or by the cloning of genetic sequences which are capable of encoding such protein with polymerase chain reaction technologies; and through the expression of such genetic sequences. As used herein, the term "genetic sequences" is intended to refer to a nucleic acid molecule (preferably DNA). Genetic sequences which are capable of encoding a protein are derived from a variety of sources. These sources include genomic DNA, cDNA, synthetic DNA, and combinations thereof. The preferred source of genomic DNA is a fungal genomic library. The preferred source of the cDNA is a cDNA library prepared from fungal mRNA grown in conditions known to induce expression of the desired mRNA or protein.

The genomic DNA of the invention may or may not include naturally occurring introns. Moreover, such genomic DNA may be obtained in association with the 5' promoter region of the gene sequences and/or with the 3' transcriptional termination region. Further, such genomic DNA may be obtained in association with the genetic sequences which encode the 5' non-translated region of the mRNA and/or with the genetic sequences which encode the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA may be retained and employed for transcriptional and translational regulation. Genomic DNA can be extracted and purified from any host cell, especially a fungal host cell, which naturally expresses the desired protein by means well known in the art.

For cloning into a vector, such suitable DNA preparations (either genomic DNA or cDNA) are randomly sheared or enzymatically cleaved, respectively, and ligated into appropriate vectors to form a recombinant gene (either genomic or cDNA) library.

A DNA sequence encoding a desired protein or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., (Maniatis, T. et al., *Molecular Cloning (A Laboratory Manual)*, Cold Spring Harbor Laboratory, second edition, 1988) and are well known in the art.

Libraries containing sequences coding for the desired gene may be screened and the desired gene sequence identified by any means which specifically selects for a sequence coding for such gene or protein such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated protein product produced by the host containing the clone.

Oligonucleotide probes specific for a certain protein which can be used to identify clones to this protein can be designed from the knowledge of the amino acid sequence of the protein or from the knowledge of the nucleic acid sequence of the DNA encoding such protein or a related protein. Alternatively, antibodies may be raised against purified forms of the protein and used to identify the presence of unique protein determinants in transformants that express the desired cloned protein. The sequence of amino acid residues in a peptide is designated herein either through the use of their commonly employed three-letter designations or by their single-letter designations. A listing of these three-letter and one-letter designations may be found in textbooks such as *Biochemistry*, Lehninger, A., Worth Publishers, New York, N.Y. (1970). When the amino acid sequence is listed horizontally, unless otherwise stated, the amino terminus is intended to be on the left end and the carboxy terminus is intended to be at the right end. Similarly, unless otherwise stated or apparent from the context, a nucleic acid sequence is presented with the 5' end on the left.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code, one or more different oligonucleotides can be identified from the amino acid sequence, each of which would be capable of encoding the desired protein. The probability that a particular oligonucleotide will, in fact, constitute the actual protein encoding sequence can be estimated by considering abnormal base pairing relationships and the frequency with which a particular codon is actually used (to encode a particular amino acid) in eukaryotic cells. Using "codon usage rules," a single oligonucleotide sequence, or a set of oligonucleotide sequences, that contain a theoretical "most probable" nucleotide sequence capable of encoding the protein sequences is identified.

The suitable oligonucleotide, or set of oligonucleotides, which is capable of encoding a fragment of a certain gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate a clone to such gene by techniques known in the art. Techniques of nucleic acid hybridization and clone identification are disclosed by Maniatis, T., et al., in: *Molecular Cloning, A Laboratory Manual*, Cold Spring Harbor Laboratories, Cold Spring Harbor, N.Y. (1982), and by Hames, B. D., et al., in: *Nucleic Acid Hybridization, A Practical Approach*, IRL Press, Washington, D.C. (1985). Those members of the above-described gene library which are found to be capable of such hybridization are then analyzed to determine the extent and nature of coding sequences which they contain.

To facilitate the detection of a desired DNA coding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}$P, $^{3}$H, $^{14}$C, 35S, $^{125}$I or the like. Any radioactive label may be employed which provides for an adequate signal and has a sufficient half-life. If single stranded, the oligonucleotide may be radioactively labelled using kinase reactions. Alternatively, polynucleotides are also useful as nucleic acid hybridization probes when labeled with a non-radioactive marker such as biotin, an enzyme or a fluorescent group.

Thus, in summary, the elucidation of a partial protein sequence, permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing a gene.

In an alternative way of cloning a gene, a library is prepared using an expression vector, by cloning DNA or, more preferably cDNA prepared from a cell capable of expressing the protein into an expression vector. The library is then screened for members which express the desired protein, for example, by screening the library with antibodies to the protein.

The above discussed methods are, therefore, capable of identifying genetic sequences which are capable of encoding a protein or biologically active or antigenic fragments of this protein. In order to further characterize such genetic sequences, and, in order to produce the recombinant protein, it is desirable to express the proteins which these sequences encode. Such expression identifies those clones which express proteins possessing characteristics of the desired protein. Such characteristics may include the ability to specifically bind antibody, the ability to elicit the production of antibody which are capable of binding to the native, non-recombinant protein, the ability to provide a enzymatic activity to a cell that is a property of the protein, and the ability to provide a non-enzymatic (but specific) function to a recipient cell, among others.

A DNA sequence may be shortened by means known in the art to isolate a desired gene from a chromosomal region that contains more information than necessary for the utilization of this gene in the hosts of the invention. For example, restriction digestion may be utilized to cleave the full-length sequence at a desired location. Alternatively, or in addition, nucleases that cleave from the 3'-end of a DNA molecule may be used to digest a certain sequence to a shortened form, the desired length then being identified and purified by gel electrophoresis and DNA sequencing. Such nucleases include, for example, Exonuclease III and Bal31. Other nucleases are well known in the art.

If the coding sequence and an operably linked promoter are introduced into a recipient eukaryotic cell as a non-replicating DNA (or RNA), non-integrating molecule, the expression of the encoded protein may occur through the transient (nonstable) expression of the introduced sequence.

Preferably the coding sequence is introduced on a DNA (or RNA) molecule, such as a closed covalent circular molecule that is incapable of autonomous replication, or preferable a linear molecule that integrates into the host chromosome. Genetically stable transformants may be constructed with vector systems, or transformation systems, whereby a desired DNA is integrated into the host chromosome. Such integration may occur de novo within the cell or, be assisted by transformation with a vector which functionally inserts itself into the host chromosome, for example, transposons or other DNA elements which promote integration of DNA sequences in chromosomes. A vector is employed which is capable of integrating the desired gene sequences into a fungal host cell chromosome.

The genes coding for phytase or pH 2.5 acid phosphatase under the control of suitable promoters may be combined in one plasmid construction and introduced into the host cells by transformation. The nature of the plasmid vector will depend on the host organism. In the practical realization of the invention the filamentous fungus Trichoderma has been employed as a model. Thus, for Trichoderma and especially for *T. reesei*, vectors incorporating DNA that provides for integration of the sequences encoding the phytase or pH 2.5 acid phosphatase genes into the host's chromosome are preferred. Targeting the integration to the cbh1 (DNA encoding the enzyme cellobiohydrolase I) locus of the host is the preferred method of obtaining the high level expression of the phytase or pH 2.5 acid phosphatase genes of the invention, such targeting may be achieved by providing cbh1 coding or flanking sequences on the recombinant construct, in an amount sufficient to direct integration to this locus at a relevant frequency.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection. A genetic marker especially for the transformation of the hosts of the invention is amdS, encoding acetamidase and thus enabling Trichoderma to grow on acetamide as the only nitrogen source.

To express a desired protein and/or its active derivatives, transcriptional and translational signals recognizable by an appropriate host are necessary. The cloned coding sequences, obtained through the methods described above, and preferably in a double-stranded form, may be operably linked to sequences controlling transcriptional expression in an expression vector, and introduced into a host cell, either prokaryote or eukaryote, to produce recombinant protein or a functional derivative thereof. Depending upon which strand of the coding sequence is operably linked to the sequences controlling transcriptional expression, it is also possible to express antisense RNA or a functional derivative thereof.

Expression of the protein in different hosts may result in different post-translational modifications which may alter the properties of the protein. Preferably, the present invention encompasses the expression of the protein or a functional derivative thereof, in eukaryotic cells, and especially in fungus.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a coding sequence and a promoter region sequence linked to the 5' end of the coding sequence) are said to be operably linked if induction of promoter function results in the transcription of mRNA encoding the desired protein and if the nature of the linkage between the two DNA sequences does not (1) result in the introduction of a frame-shift mutation, (2) interfere with the ability of the expression regulatory sequences to direct the expression of the protein, antisense RNA, or (3) interfere with the ability of the DNA template to be transcribed. Thus, a promoter region would be operably linked to a DNA sequence if the promoter was capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene. Such transcriptional control sequences may also include enhancer sequences or upstream activator sequences, as desired.

Expression of a protein in eukaryotic hosts such as fungus requires the use of regulatory regions functional in such hosts, and preferably fungal regulatory systems. A wide variety of transcriptional and translational regulatory sequences can be employed, depending upon the nature of the host. Preferably, these regulatory signals are associated in their native state with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from filamentous fungal genes which encode a mRNA product capable of translation are preferred, and especially, strong promoters can be employed provided they also function as promoters in the host cell. Preferred strong eukaryotic promoters for use in Trichoderma include the *T. reesei* cbh1 gene promoter or a promoter of another cellulase gene such as that for the cbh2, eg/1 or eg/2 gene may be used. In addition to the use of Trichoderma regulatory elements, the expression of proteins may be placed under the control of regulatory elements from *Aspergillus nidulans* (for example, the argB gene promoter and the amdS gene promoter), *Aspergillus niger* (for example, the phytase promoter or the glucoamylase gene promoter) However, expression under non-Trichoderma regulatory elements such as these may be very low as compared to the use of Trichoderma elements, and especially those of *T. reesei*.

As is widely known, translation of eukaryotic mRNA is initiated at the codon which encodes the first methionine. For this reason, it is preferable to ensure that the linkage between a eukaryotic promoter and a DNA sequence which encodes the desired protein, or a functional derivative thereof, does not contain any intervening codons which are capable of encoding a methionine. The presence of such codons results either in a formation of a fusion protein (if the AUG codon is in the same reading frame as the protein-coding DNA sequence) or a frame-shift mutation (if the AUG codon is not in the same reading frame as the protein-coding sequence).

It may be desired to construct a fusion product that contains a partial coding sequence (usually at the amino terminal end) of a protein and a second coding sequence (partial or complete) of a phytase degrading enzyme of the invention. The sequence that does not encode the phytase degrading enzyme may or may not function as a signal sequence for secretion of the protein from the host cell. For example, the sequence coding for desired protein may be linked to a signal sequence which will allow secretion of the protein from, or the compartmentalization of the protein in, a particular host. Such fusion protein sequences may be designed with or without specific protease sites such that a desired peptide sequence is amenable to subsequent removal. In a preferred embodiment, the native signal sequence of a fungal protein is used, or a functional derivative of that sequence that retains the ability to direct the secretion of the peptide that is operably linked to it. Aspergillus leader/secretion signal elements also function in Trichoderma.

Transcriptional initiation regulatory signals can be selected which allow for repression or activation, so that expression of the operably linked genes can be modulated. For example, regulatory signals may be temperature-sensitive so that by varying the temperature, expression can be repressed or initiated, or are subject to chemical regulation, e.g., metabolite. Translational signals are not necessary when it is desired to express antisense RNA sequences.

If desired, the non-transcribed and/or non-translated regions 3' to the sequence coding for a desired protein can be obtained by the above-described cloning methods. The 3'-non-transcribed region may be retained for its transcriptional termination regulatory sequence elements, or for those elements which direct polyadenylation in eukaryotic cells. Where the native expression control sequences signals do not function satisfactorily in a host cell, then sequences functional in the host cell may be substituted.

The vectors of the invention may further comprise other operably linked regulatory elements such as DNA elements which confer antibiotic resistance, or origins of replication for maintenance of the vector in one or more host cells.

In another embodiment, especially for maintenance of the vectors of the invention in prokaryotic cells, or in yeast *S. cerevisiae* cells, the introduced sequence is incorporated into a plasmid or viral vector capable of autonomous replication in the recipient host. Any of a wide variety of vectors may be employed for this purpose. In Bacillus hosts, integration of the desired DNA may be necessary.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred *S. cerevisiae* yeast plasmids include those containing the 2-micron circle, etc., or their derivatives. Such plasmids are well known in the art (Botstein, D., et al., *Miami Wntr. Symp.* 19:265–274 (1982); Broach, J. R., in: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin.*

*Hematol. Oncol.* 10:39–48 (1980); Maniatis, T., In: *Cell Biology: A Comprehensive Treatise*, Vol. 3, Gene Expression, Academic Press, N.Y., pp. 563–608 (1980)), and are commercially available.

Once the vector or DNA sequence containing the construct(s) is prepared for expression, the DNA construct (s) is introduced into an appropriate host cell by any of a variety of suitable means, including transformation. After the introduction of the vector, recipient cells are grown in a selective medium, which selects for the growth of vector-containing cells. Expression of the cloned gene sequence(s) results in the production of the desired protein, or in the production of a fragment of this protein. This expression can take place in a continuous manner in the transformed cells, or in a controlled manner, for example, by induction of expression.

Fungal transformation is carried out also accordingly to techniques known in the art, for example, using, for example, homologous recombination to stably insert a gene into the fungal host and/or to destroy the ability of the host cell to express a certain protein.

IV. PREPARATION OF ANTIBODIES

In the following description, reference will be made to various methodologies well-known to those skilled in the art of immunology. Standard reference works setting forth the general principles of immunology include the work of Catty, D. (*Antibodies, A Practical Approach*, Vol. 1, IRL Press, Washington, D.C. (1988)); Klein, J. (*Immunology: The Science of Cell-Noncell Discrimination*, John Wiley & Sons, New York (1982)); Kennett, R., et al. in *Monoclonal Antibodies, Hybridoma: A New Dimension in Biological Analyses*, Plenum Press, New York (1980); Campbell, A. ("Monoclonal Antibody Technology," in: *Laboratory Techniques in Biochemistry and Molecular Biology*, Volume 13 (Burdon, R., et al., eds.), Elsevier, Amsterdam (1984)); and Eisen, H. N., in: *Microbiology*, 3rd Ed. (Davis, B. D., et al., Harper & Row, Philadelphia (1980)).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evolved by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

The antibodies of the present invention are prepared by any of a variety of methods. Preferably, purified phytase or pH 2.5 acid phosphatase protein, or a fragment thereof, (treated or not treated with endoF or its equivalent to remove sugar moieties), is administered to an animal in order to induce the production of sera containing polyclonal antibodies that are capable of binding such phytase or pH 2.5 acid phosphatase.

Cells expressing phytase or pH 2.5 acid phosphatase protein, or a fragment thereof, or, a mixture of proteins containing phytase or pH 2.5 acid phosphatase or such fragments, can also be administered to an animal in order to induce the production of sera containing polyclonal antibodies, some of which will be capable of binding phytase or pH 2.5 acid phosphatase protein. If desired, such phytase or pH 2.5 acid phosphatase antibody may be purified from the other polyclonal antibodies by standard protein purification techniques and especially by affinity chromatography with purified phytase or pH 2.5 acid phosphatase or fragments thereof.

A phytase or pH 2.5 acid phosphatase protein fragment may also be chemically synthesized and purified by HPLC to render it substantially free of contaminants. Such a preparation is then introduced into an animal in order to produce polyclonal antisera of high specific activity.

Monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., in: *Monoclonal Antibodies and T-Cell Hybridomas*, Elsevier, N.Y., pp. 563–681 (1981)). In general, such procedures involve immunizing an animal with phytase or pH 2.5 acid phosphatase protein antigen. The splenocytes of such animals are extracted and fused with a suitable myeloma cell line. Any suitable myeloma cell line may be employed in accordance with the present invention; however, it is preferable to employ the parent myeloma cell line ($SP_2O$), available from the American Type Culture Collection, Rockville, Md. After fusion, the resulting hybridoma cells are selectively maintained in HAT medium, and then cloned by limiting dilution as described by Wands, J. R., et al., *Gastroenterology* 80:225–232 (1981), which reference is herein incorporated by reference. The hybridoma cells obtained through such a selection are then assayed to identify clones which secrete antibodies capable of binding the phytase or pH 2.5 acid phosphatase protein antigen.

Through application of the above-described methods, additional cell lines capable of producing antibodies which recognize epitopes of the phytase or pH 2.5 acid phosphatase protein can be obtained.

Antibodies against both highly conserved and poorly conserved regions of the phytase or pH 2.5 acid phosphatase protein are useful for studies on the control of biosynthesis and catabolism of phytase or pH 2.5 acid phosphatase protein, and for studies wherein it is necessary to identify or quantitate the presence and/or of the protein antigen in a composition.

V. PRODUCTION OF PHYTASE AND ACID PHOSPHATASE

The best phytase production levels are obtained when Trichoderma are transformed with linear DNA and sing the cbh1 promoter (about 3800 PNU/ml, see Table 8). About 3480 and 3600 PNU/ml culture medium was obtained with the best *T. reesei* ALKO 2221 and ALKO 233 transformants containing no *E. coli* sequences, respectively. The best *T. reesei* ATCC 56765 transformant with no *E. coli* sequences produced about 1,800 PNU/ml culture medium. Both the phytase and the cbh1 signal sequence seemed to work equally well. In one host, (ALKO 233), the level of phytase was higher when the phytase signal sequence was used.

Phytase is expressed from the Trichoderma hosts of the invention into the supernatant of the culture medium. The amount of phytase in the culture medium is generally higher than any hitherto reported amount of a heterologous protein that was expressed in Trichoderma.

The spectrum of enzymes that accompany phytase in the Trichoderma strains of the invention is greatly different and advantageous over that of similar preparations of Aspergillus culture supernatants. Both endoglucanase and cellobiohydrolase activities are generally substantially higher using the Trichoderma hosts of the invention. The glycosylation pattern of the phytase is also different when it is expressed from Trichoderma, resulting in a phytase protein that migrates as multiple bands on Western analysis.

The best production of pH 2.5 acid phosphatase from the Trichoderma transformants of the invention resulted in 240 APNU/ml culture medium, in shake flask cultivation and in lactose based medium. As with the phytase, both the acid phosphatase and the cbh1 signal sequence worked equally well.

The compositions of the invention that contain phytase may be used directly for the removal of phytic acid, or inositol hexaphosphoric acid, from raw material, especially phytin-containing raw material, and especially plant material. Phytase removes the phosphate groups from phytic acid and destroys its ability to interfere with mineral absorption. When used as an animal feed additive, the phytase compositions of the invention release phosphate bound to phytin in grain and thus dramatically reduce the need for doses of additional phosphate in feed formulations and lessen environmental loads.

The phytase and pH 2.5 acid phosphatase produced according to the invention may be purified by protein purification methods known in the art.

Having now generally described the invention, the same will become better understood by reference to certain specific examples that are included herein for purposes of illustration only and are not intended to be limiting unless otherwise specified.

EXAMPLES

Example 1

Method of Assay of Phytase Activity

Principle Phytase acts on phytate (inositol hexaphosphate) to release inorganic phosphate. The determination of released inorganic phosphate is based on the color formed by the reduction of a phosphomolybdate complex.

Unit of Activity One phytase unit (PU) is the amount of enzyme which liberates, under standard conditions, 1 nmol of inorganic phosphate from sodium phytate in one minute.

Assay conditions

Substrate Sodium phytate pH 5.0 incubation temperature 37° C. ±0.5° C.

incubation time 15 minutes

Equipment

Water bath 37° C.

Water bath 50° C.

Spectrophotometer

Test tube mixer (vortex)

Phosphate Free Glassware

Reagents All solutions are prepared in deionized water, Milli-Q or equivalent.

1. Citrate Buffer (0.2M, pH 5.0). Prepare 0.2M solutions of both sodium citrate ($C_6H_8O_7Na.2H_2O$, 58.8 g/l, Merck 6448) and citric acid ($C_6H_8O_7.H_2O$, 42.0 g/l, Merck 244) in water. Adjust the pH of the citrate solution (1 liter) to 5.0 with 0.2M citric acid (the consumption of citric acid solution should be about 385 ml).

2. Substrate. Dissolve 1.00 g of sodium phytate (Sigma P-3168) in about 70 ml citrate buffer. Adjust the pH to 5.0 with 0.2M citric acid and adjust the volume to 100 ml with citrate buffer. Fresh substrate solution must be prepared daily.

3. 15% (w/v) TCA Solution. Prepare from trichloroacetic acid (Merck 807).

4. 10% (w/v) Ascorbic Acid Solution. Prepare from ascorbic acid (Merck 127). Store under refrigeration. The solution is stable for seven days.

5. 2.5 % (w/v) Ammonium Molybdate Solution. Dissolve 2.5 g $(NH_4)_6Mo_7O_{24}.4H_2O$, Merck 1182) in water and make up to 100 ml.

6. 1M Sulfuric Acid. Add 55.6 ml of concentrated $H_2SO_4$ (Merck 731) to about 800 ml of water, with stirring. Allow to cool and make up to 1000 ml with water.

7. Reagent C. Mix 3 volumes of 1M sulfuric acid with 1 volume of 2.5% ammonium molybdate, then add 1 volume of 10% ascorbic acid and mix well. Fresh reagent C must be prepared daily.

Sample dilution Samples are diluted in citrate buffer. Make duplicate dilutions of each sample. In case of enzyme powder weigh accurately about 250 mg of sample, dissolve in the buffer and fill to 25 ml in a volumetric flask, dilute further if necessary.

Dilution table:

| Estimated activity PU/ml | Recommended dilution | Dilution factor |
|---|---|---|
| 2000 | 1 + 19 | 20 |
| 20000 | 1 + 199 | 200 |
| 40000 | 1 + 399 | 400 |
| 100000 | 1 + 999 | 1000 |
| 500000 | 1 + 4999 | 5000 |

Assay

Hydrolysis Pipette 1.0 ml of sample dilution containing 20–190 PU in two test tubes. Add 2.0 ml of 15% TCA to one of the tubes (blank) and mix. Put the tubes without TCA in a water bath at 37° C. and let them equilibrate for 5 minutes. Using a stopwatch start the hydrolysis by adding sequentially at proper intervals 1.0 ml of substrate (equilibrated for about 10 minutes at 37° C.) to each tube and mix. After exactly 15 minutes incubation stop the reaction by adding 2.0 ml of TCA to each tube. Mix and cool to room temperature. Add 1.0 ml substrate to the blank tubes (kept at room temperature) also and mix. If precipitate occurs it must be separated by centrifugation for 10 minutes at 2000.g.

Released orthophosphate Pipette 0.4 ml of each sample after hydrolysis in test tubes. Add 3.6 ml of water to each tube. Add 4.0 ml of reagent C and mix. Incubate at 50° C. for 20 minutes and cool to room temperature. Measure the absorbance against that of reagent blank (see below) at 820 nm.

Standard Prepare a 9.0 mM phosphate stock solution. Dissolve and dilute 612.4 mg $KH_2PO_4$ (Merck 4873, dried in desiccator with silica) to 500 ml with water in a volumetric flask. Make the following dilutions in water from the stock solution and use these as standards.

| Dilution | Phosphorus concentration nmol/ml | Phytase activity PU/ml* |
|---|---|---|
| 1:100 | 90 | 240 |
| 1:200 | 45 | 120 |
| 1:400 | 22.5 | 60 |

*The corresponding phytase activity (PU/ml) is obtained by dividing the phosphorous concentration (nmol/ml) by the time of hydrolysis (15 minutes) and multiplying by four (total volume after hydrolysis reaction/sample volume) and by 10 (dilution before analysis of inorganic phosphorous).

Pipette 4.0 ml of each dilution to two test tubes. Pipette also 4.0 ml of water in one tube (reagent blank). Add 4.0 ml of reagent C and mix. Incubate at 50° C. for 20 minutes and cool to room temperature. Measure the absorbances at 820 nm against that of reagent blank. Prepare a standard curve by blotting the absorbances against phytase activity (PU/ml). A new standard line must be constructed with each series of assays.

Calculation Subtract the blank absorbance from the sample absorbance (the difference should be 0.100–1.000). Read the phytase activity (PU/ml) from the standard line and multiply by the dilution factor. To calculate the activity (PU/g) of enzyme powders the result (PU/ml) is further multiplied by 25 (ml) and divided by the exact weight of the sample (g).

Preparation of feed and other insoluble samples for phytase analysis

Weigh accurately about 2.5 g of ground sample in two 50 ml beakers. Add 20.0 ml of citrate buffer. Mix using a magnetic stirrer for 30 minutes at room temperature. Transfer about 10 ml of each in centrifuge tubes and separate the solid matter by centrifugation for 10 minutes at 2000.g. Apply 2.5 ml of supernatant on PD-10 gel filtration columns (Sephadex G-25M, Pharmacia 17-0851-01) equilibrated with 25 ml citrate buffer. Discard the eluate. Then apply 3.5 ml citrate buffer on the column and collect the eluate in a graduated cylinder. Fill the volume to 5.0 ml with citrate buffer (dilution factor 2) and assay for phytase activity. The activity PU/g is obtained by multiplying the measured activity (PU/ml) by 40 (dilution factor·volume of extraction buffer) and dividing by the exact weight of sample (g). Reference: Chen et al. *Anal. Chem.* 28:1756–1758 (1956).

Example 2

Assay of Acid Phosphatase Activity

Principle. Acid phosphatase acts on p-nitrophenyl phosphate to release inorganic phosphate. The determination of released inorganic phosphate is based on the color formed by the reduction of phosphomolybdate complex.

Unit of activity. One acid phosphatase unit (HFU) is the amount of enzyme which liberates, under standard conditions, 1 nmol of inorganic phosphate from p-nitrophenyl phosphate in one minute.

Assay conditions

Substrate p-nitrophenyl phosphate pH 2.5

Temperature 37° C. ±0.5° C.

Incubation time 15 min

Equipment

Water bath 37° C.

Water bath 50° C.

Spectrophotometer

Test tube mixer (vortex)

Centrifuge (Hereaus Biofuge 17S, 3090 or equivalent,

Phosphate Free Glassware

Reagents. All solutions are prepared in deionized water, Milli-Q or equivalent.

1. Glycine Buffer (0.2M, pH 2.5)
   Dissolve 15.014 g glycine (Merck 4201) in about 800 ml of water. Adjust the pH to 2.5 with 1M hydrochloric acid (consumption should be about 80 ml) and dilute to 1000 ml with water.

2. Substrate (30 mM)
   Dissolve 1.114 g p-nitrophenyl phosphate (Boehringer, 738 352) in glycine buffer and adjust the volume to 100 ml with the buffer. Fresh substrate solution must be prepared daily.

3. 15% (w/v) TCA Solution
   Prepare from trichloroacetic acid (Merck 807).

4. 10% (w/v) Ascorbic Acid Solution
   Prepare from ascorbic acid (Merck 127). Store under refrigeration. The solution is stable for 7 days.
5. 2.5% (w/v) Ammonium Molybdate Solution
   Dissolve 2.5 g $(NH_4)_6MO_7O_{24}.4H_2O$, Merck 1182) in water and make up to 100 ml.
6. 1M Sulphuric Acid
   Add 55.6 ml of concentrated $H_2SO_4$ (Merck 731) to about 800 ml of water, with stirring. Allow to cool and make up to 1000 ml with water.
7. Reagent C
   Mix 3 volumes of 1M sulphuric acid with 1 volume of 2.5% ammonium molybdate, then add 1 volume of 10% ascorbic acid and mix well. Fresh reagent C must be prepared daily.

Sample dilution. Samples are diluted in glycine buffer. Make duplicate dilutions of each sample. In case of enzyme powder weigh accurately about 250 mg of sample, dissolve in the buffer and fill to 25 ml in a volumetric flask, dilute further if necessary.

Dilution table:

| Estimated activity HFU/ml | Recommended dilution | Dilution factor |
|---|---|---|
| 20000 | 1 + 19 | 20 |
| 200000 | 1 + 199 | 200 |
| 400000 | 1 + 399 | 400 |
| 1000000 | 1 + 999 | 1000 |
| 5000000 | 1 + 4999 | 5000 |

Assay

Hydrolysis: Pipette 1.9 ml of substrate in two test tubes. Add 2.0 ml of 15% TCA to one of the tubes (blank) and mix. Put the tubes without TCA in a water bath at 37° C. and let them equilibrate for 5 min. Using a stopwatch start the hydrolysis by adding sequentially at proper intervals 0.1 ml of enzyme dilution to each tube and mix. After exactly 15 min incubation stop the reaction by adding 2.0 ml of TCA to each tube. Mix and cool to room temperature. Add 0.1 ml of sample to the blank tubes (kept at room temperature) also and mix. If precipitate occurs it must be separated by centrifugation for 10 min at 2000.g.

Released orthophosphate: Pipette 0.4 ml of each sample after hydrolysis in test tubes. Add 3.6 ml of water to each tube. Add 4.0 ml of reagent C and mix. Incubate at 50° C. for 20 min and cool to room temperature. Measure the absorbance against that of reagent blank (see below) at 820 nm.

Standard. Prepare a 9.0 mM phosphate stock solution. Dissolve and dilute 612.4 mg $KH_2PO_4$ (Merck 4873, dried in dessicator with silica) to 500 ml with water in a volumetric flask. Make the following dilutions in water from the stock solution and use these as standards.

| Dilution | Phosphorus concentration nmol/ml | Acid phosphatase activity HFU/ml* |
|---|---|---|
| 1:100 | 90 | 2400 |
| 1:200 | 45 | 1200 |
| 1:400 | 22.5 | 600 |

*The corresponding acid phosphatase activity (HFU/ml) is obtained by dividing the phosphorus concentration (nmol/ml) by the time of hydrolysis (15 min) and multiplying by 40 (total volume after hydrolysis reaction/sample volume) and by 10 (dilution before analysis of inorganic phosphorus).

Pipette 4.0 ml of each dilution to two test tubes. Pipette also 4.0 ml of water in one tube (reagent blank). Add 4.0 ml of reagent C and mix. Incubate at 50° C. for 20 min and cool to room temperature. Measure the absorbances at 820 nm against that of reagent blank. Prepare a standard curve by blotting the absorbances against acid phosphatase activity (HFU/ml). A new standard line must be constructed with each series of assays.

Calculation. Subtract the blank absorbance from the sample absorbance (the difference should be 0.100–1.000). Read the acid phosphatase activity (HFU/ml) from the standard line and multiply by the dilution factor. To calculate the activity (HFU/g) of enzyme powders the result (HFU/ml) is further multiplied by 25 (ml) and divided by the exact weight of the sample (g).

Preparation of feed and other insoluble samples for acid phosphatase analysis. Weigh accurately about 2.5 g of ground sample in two 50 ml beakers. Add 20.0 ml of glycine buffer. Mix using a magnetic stirrer for 30 min at room temperature. Transfer about 10 ml of each in centrifuge tubes and separate the solid matter by centrifugation for 10 min at 2000.g. Apply 2.5 ml of supernatant on PD-10 gel filtration columns (Sephadex G-25M, Pharmacia 17-0851-01) equilibrated with 25 ml glycine buffer. Discard the eluate. Then apply 3.5 ml of glycine buffer on the column and collect the eluate in a graduated cylinder. Fill the volume to 5.0 ml with glycine buffer (dilution factor 2) and assay for acid phosphatase activity. The activity HFU/g is obtained by multiplying the measured activity (HFU/ml) by 40 (dilution factor·volume of extraction buffer) and dividing by the exact weight of sample (g). Reference: Chen, P. S., et al., *Anal. Chem.* 28:1756–1758 (1956).

Example 3

Purification of Phytase and pH 2.5 Acid Phosphatase

For reference to how the skilled artisan would purify phytase and pH 2.5 acid phosphatase, the following are provided.

I. PHYTASE

Enzyme purification. Steps were done at 4° to 8° C. unless otherwise stated. The starting material was the cell-free culture medium concentrate produced by *Aspergillus niger* var. awamori ALKO 243.

Ammonium sulphate precipitation. The culture filtrate concentrate (990 ml) was kept on an ice bath and 0.436 g ammonium sulphate per ml was added (70% saturation). After 30 minutes the precipitate was separated by centrifugation for 15 minutes at 10000.g and discarded.

Hydrophobic interaction chromatography. The supernatant (1070 ml) was applied to an Octyl-Sepharose CL-4B (Pharmacia) column (5 cm×17 cm) equilibrated with a solution containing 0.436 g $(NH_4)_2SO_4$ per ml of 20 mM bis-Tris/HCl (pH 6.2). The column was washed with 500 ml of the equilibration solution and then developed with a linear gradient of 500 ml containing 70→0% amonium sulfate in 20 mM bis-Tris/HCl (pH 6.2). Fractions of 10 ml were collected and analyzed for phytase and acid phosphatase activity. Most of the phytase activity eluted in the beginning of the gradient. The fractions were pooled for the next step. The fractions eluting after phytase activity and containing most of the acid phosphatase activity were pooled for acid phosphatase purification (see below).

Anion exchange chromatography. The pooled phytase fractions (129 ml) were concentrated by ultrafiltration using an Amicon PM 10 membrane. The residual ammonium sulphate was removed by PD 10 (Pharmacia) gel filtration columns equilibrated with 50 mM bis-Tris/HCl (pH 6.2). The sample, in 24.5 ml, was applied to a DEAE-Sepharose (Pharmacia) column (5 cm×7 cm) equilibrated with 50 mM bis-Tris/HCl (pH 6.2). The column was washed with the equilibrium buffer (100 ml) and developed by a linear gradient of 200 ml containing 0→0.5M NaCl in equilibrium buffer.

Gel filtration. The pooled active fractions were concentrated using a Centricon -30 microconcentrator to a total volume of 600 µl. Portions of 100 µl were run at about 23° C. and 0.3 ml/min through a Superose 12 HR 10/30 HPLC column (Pharmacia) equilibrated with 50 mM bis-Tris/HCl (pH 6.2).

Cation exchange. The pooled active fractions were transferred to 50 mM sodium formiate (pH 3.8) using a Centricon -30 microconcentrator. The sample was applied in two portions of 2 ml to a Mono S HR 5/5 FPLC column (Pharmacia) equilibrated with 50 mM sodium formiate (pH 3.8) at about 23° C. The column was washed with the equilibration buffer (10 ml) and the bound protein was eluted at 60 ml/h with a linear gradient of 20 ml containing 0→430 mM NaCl in equilibration buffer.

II. ACID PHOSPHATASE

Gel filtration. The pooled fractions containing most of the acid phosphatase activity from the hydrophobic interaction chromatography step were concentrated by ultrafiltration using an Amicon PM 10 membrane. The concentrated sample (25 ml) was run through a Sephacryl S-200 (Pharmacia) column (2.6 cm×94 cm) equilibrated with 50 mM bis-Tris/HCl (pH 6.2) at 20 ml/h.

Anion exchange chromatography. The pooled fractions (48 ml) were applied to a DEAE-Sepharose (Pharmacia) column (5 cm×7 cm) equilibrated with 50 mM bis-Tris/HCl (pH 6.2). The column was washed with 100 ml of equilibration buffer and developed with a linear gradient of 200 ml containing 0→0.5M NaCl in equilibration buffer.

Anion exchange chromatography. The pooled active fractions were concentrated and transferred to 20 mM bis-Tris/HCl (pH 6.0) by ultrafiltration using an Amicon PM 10 membrane. The sample was run in four portions of 3.5 ml on Mono Q HR 515 HPLC column (Pharmacia) equilibrated with 20 mM bis-Tris/HCl (pH 6.0) at about 23° C. and 60 ml/h. The column was washed with 10 ml of the equilibrium buffer and the bound protein was eluted with a linear gradient of 20 ml containing 0→350 mM NaCl in equilibrium buffer.

Gel filtration. The active fractions were pooled, concentrated and transferred to 20 mM bis-Tris/HCl (pH 6.2) containing 150 mM NaCl with Centricon -30 microconcentrator to total volume of 400 µl. Portions of 100 µl were run at about 23° C. and 18 ml/h through a Superose 12 HR 10/30 HPLC column (Pharmacia) equilibrated with the sample buffer.

Anion exchange chromatography. The pooled active fractions were transferred to 20 mM histidin/HCl (pH 5.8) with a PD 10 gel filtration column. The sample was run in four portions of 1 ml on Mono Q HR 5/5 HPLC column (Pharmacia) equilibrated with the sample buffer at about 23° C. and 60 ml/h. The column was washed with 5 ml of the sample buffer and the bound protein was eluted with a linear gradient of 20 ml containing 0→350 mM NaCl in equilibrium buffer.

TABLE 1

Summary of purification of phytase from *Aspergillus niger*

| Step | Total activity (U) | Total protein (mg) | Specific activity (U/mg) | Yield (%) | Purification (fold) |
| --- | --- | --- | --- | --- | --- |
| Culture filtrate | 4486680 | 2119 | 2117 | 100 | 1 |
| Ammonium sulfate supernatant | 3771750 | 1263 | 2986 | 84.1 | 1.4 |
| Octyl Sepharose | 1765881 | 32.3 | 54671 | 39.4 | 26 |
| DEAE-Sepharose | 1453470 | 8.4 | 173032 | 32.4 | 82 |
| Superose 12 | 1010888 | 5.7 | 177349 | 22.5 | 84 |
| Mono S | 827566 | 3.0 | 275885 | 18.4 | 130 |

TABLE 2

Summary of purification of acid phosphatase from *Aspergillus niger*

| Step | Total activity (U) | Total protein (mg) | Specific activity (U/mg) | Yield (%) | Purification (fold) |
| --- | --- | --- | --- | --- | --- |
| Culture filtrate | 116523000 | 2119 | 54990 | 100 | 1 |
| Ammonium sulphate supernatant | 88275000 | 1263 | 69893 | 75.8 | 1.3 |
| Octyl Sepharose | 68296470 | 583 | 117147 | 58.6 | 2.1 |
| Sephacryl | 52237600 | 97.9 | 533581 | 44.8 | 9.7 |
| DEAE-Sepharose | 46127692 | 54.6 | 844830 | 39.6 | 15.4 |
| Mono Q | 19326753 | 3.28 | 5892303 | 16.6 | 107 |
| Superose | 16876978 | nd | nd | 14.5 | nd |
| Mono Q | 15197050 | 2.2 | 6907750 | 13.0 | 126 | nd = not determined

Example 4

Characterization of Purified Phytase and pH 2.5 Acid Phosphatase Peptide Digestions Native purified phytase (70 µg) in 50 mM Tris-HCl pH 7.9 was digested with 2% (w/w) trypsin (TPCK-treated, Sigma) for 2 hours at 37° C. and then with a further 2% (w/w) trypsin for 21 hours. One lot of native purified phosphatase in 100 mM Tris-HCl pH 8.0 was treated with 2% (w/w) trypsin for 20 hours at 37° C. and then with a further 2% (w/w) trypsin for 6 hours. The peptides were purified as described below.

Another lot of purified native phosphatase was alkylated using 4-vinyl pyridine as follows: To lyophilized phosphatase (75 µg) was added 40 µl 0.5M Tris-HCl pH 7.5 containing 6M guanidium hydrochloride, 2 mM EDTA and 34 mM DTT. After addition of 1 µl 4-vinyl pyridine (Sigma), the reaction mixture was kept at room temperature (22° C.) for 1 hour. The reaction was stopped by addition of 10 µl 1.4M DTT. Alkylated phosphatase was then purified on HPLC with a C-1 reverse-phase column (TSK TMS 250; 0.46×4 cm) using a 20% to 70% ACN/0.06% TFA gradient (80% to 30% 0.1% TFA) in 30 minutes. The fractions absorbing at 218 nm were pooled and evaporated in a Speed-Vac vacuum centrifuge. The dried sample was resuspended in 60 µl 70 mM Tris-HCl pH 9.1 and digested with 2% (w/w) lysylendopeptidase C (Wako Chemicals) for 2 hours at 37° C. After addition of a further 2% (w/w) lysylendopeptidase C, the incubation at 37° C. was prolonged to 26 hours. The peptides were purified as described below.

Peptide purification and amino terminal sequencing

The peptides obtained by digestions were separated by HPLC on a C-18 reverse-phase column (Vydac 218 TP B5; 0.46×25 cm) with a 90 minute gradient from 0 to 60% ACN/0.06% TFA (100 to 40% of 0.1% TFA). Absorbance at 218 nm was used for detection of peptides.

Amino terminal sequencing of the purified peptides, as well as the native proteins, was done by degrading them in a gas-pulsed-liquid-phase sequencer (Kalkkinen and Tilgmann, 1988) *J. Prot. Chem.* 7:242–243). The released PTH-amino acids were analyzed on-line by using narrow-bore reverse-phase HPLC.

Carboxy terminal sequencing of phytase

One lot of purified phytase (53 μg) was digested with carboxypeptidase Y (Sigma, 0.6U) in 50 mM sodium acetate pH 5.6 containing 10% urea and 0.05% SDS at room temperature (22° C.). Samples of the digestion were withdrawn at various time points. These were dried in a Speed-Vac vacuum centrifuge and derivatized with phenylisothio-cyanate (PITC) according to the amino acid analyzing kit Pico-Tag (Waters association). Analysis of the derivatized amino acids was performed by reverse-phase HPLC with the Pico-Tag C-18 column, and quantified by identically derivatized amino acid standards.

Results and Discussion

Sequences could be extracted from the peptides showing "double sequences" (for both phytase and phosphatase, Table 4) since they were quantitatively different and/or the other sequence was already known from peptides sequenced. Native phosphatase seemed to be somewhat resistant to lysylendopeptidase C digestion. After alkylation however, peptides of phosphatase were nicely obtained with lysyl-endopeptidase C.

The amino terminal sequence obtained from phytase (Nphy, #1081, [SEQ ID No. :50:]) was similar, but not identical, to the amino terminal sequence of *A. ficuum* phytase (LAVPASRNQSSGDT) [SEQ ID No.:17:] reported by Ullah, A. H. J. *Prep. Biochem.* 18:459–471 (1988). Peptides resulting from trypsin digestions are shown in Table 3. One peptide (10 phy) [SEQ ID NO.:23:] had identical sequences with the internal peptide of *A. ficuum* phytase (MMQCQAEQEPLVRVLVNDR); SEQ ID No. :67: Ullah, A. H. J. *Prep. Biochem.* 18:459–471 (1988). Carboxyterminal sequencing of phytase gave the sequence XSA-OH.

No results were obtained from amino terminal sequencing of native and alkylated phosphatase (Table 4). One peptide (7Lpho) #817, [SEQ ID No. :53: ] was, however, identical with the amino terminal sequence from *A. ficuum* acid phosphatase (pH optimum 2.5; FSYGAAIPQSTQEKQFSQEFRDG) published by Ullah, A. H. J. and Cummings, B. J., *Prep. Biochem.* 17:397–422 (1987) and another (10 Lpho #941 [SEQ ID No. :54:]) seems to be a continuation of this. Peptide 3Tpho (peptide #1106 in Table 4; SEQ ID No. :61:) could also be a continuation of peptide 11Lpho (peptide #943-2 in Table 4; SEQ ID No. :60:) since it has four overlapping amino acids: FSSG.

Peptide 1Lpho (peptide #816 in Table 4; SEQ ID No. :57:) contains the active site consensus sequence RHGXRXP [SEQ ID No. :18:] of phytases and phosphatases proposed by Ullah, A. H. J. et al., *Biochem. Biophys. Res. Comun.* 178:45–53 (1991). The peptide was highly homologous, but not identical. One peptide of phytase (#675; [SEQ ID No. :37:], LKDPR) again contained part of the KDPRA [SEQ ID No. :19:] homologic sequence between *A. ficuum* phytase and different phosphatases reported by Ullah, A. H. J. et al., *Biochem. Biophys. Res. Comun.* 178:45–53 (1991).

The results indicate that *A. niger* phytase is homologous to *A. ficuum* phytase, but not identical. The same conclusion is reached in the case of acid phosphatase (pH optimum 2.5).

TABLE 3

Amino acid sequence of isolated peptides of phytase
Amino acid sequences of phytase peptides obtained as indicated in the text. In the case of uncertainty of the sequence, amino acids are shown in brackets. X, stands for undetected amino acids. The peptides are numbered (Xphy) according to appearance (retention times) in the HPLC runs.
Phytase peptides (phy) obtained by trypsin digestion.

| [SEQ ID No.: :] | Peptide No. (name) | Amino Acid Sequence[a] [Amino Acid Sequence Deduced from DNA sequence][b] |
|---|---|---|
| [:20:] | 132 (12 phy) | Tyr—Tyr—Gly—His(Leu)—Gly—Ala—Gly—Asn—Pro—Leu—Gly—Pro—Thr—Gln |
| [:21:] | 133 | [Tyr—Tyr—Gly—His_Gly—Ala—Gly—Asn—Pro—Leu—Gly—Pro—Thr—Gln] Thr—Gly—Tyr—Val—Gln(Asn)—Tyr—Val—Gln—Met—(Gln) [not found in DNA] |
| [:22:] | 242 (1 phy) | Ala—Gln—Pro—Gly—Gln—Ala—Ala—Pro—Lys [Ala—Gln—Pro—Gly—Gln—Ser—Ser—Pro—Lys] |
| [:23:] | 420 (10 phy) | Leu—Tyr—Val—Glu—Met—Met—Gln—(Asn)—Gln—Ala—(Glu)—Gln—(Thr)—Pro—Leu—Val |
| [:24:] | | [Leu—Tyr—Val—Glu—Met—Met—Gln—Cys—Gln—Ala—Glu—Gln—Glu—Pro—Leu—Val] |
| [:25:] | 410 (13 phy) | Phe—Ile—Glu—Gly—Phe—Gln—Ser—Asp—Lys |
| [:26:] | | [Phe—Ile—Glu—Gly—Phe—Gln—Ser—Asp—Lys] |
| [:27:] | 416 (7 phy) | Tyr—Ala—Phe—Leu—Lys [Tyr—Ala—Phe—Leu—Lys] |
| [:28:] | 659 (6 phy) | Gly—Leu—Ser—Phe—Ala—Arg [Gly—Leu—Ser—Phe—Ala—Arg] |
| [:29:] | 670 and 796 (2 phy) | Val—Ile—Ala—Ser—Gly—Glu—Lys [Val—Ile—Ala—Ser—Gly—Glu—Lys] |
| [:30:] | 418 (3 phy) | Phe—Tyr—Gln—Arg [Phe—Tyr—Gln—Arg] |
| [:31:] | 785 (not pure) (11 phy) | Phe—Tyr—Gln—Arg [= #418, 3phy, above] and Asp—Ser—Phe—Val—Arg |
| [:32:] | | [Asp—Ser—Phe—Val—Arg] |

TABLE 3-continued

Amino acid sequence of isolated peptides of phytase
Amino acid sequences of phytase peptides obtained as indicated in the text. In
the case of uncertainty of the sequence, amino acids are shown in brackets. X, stands for undetected
amino acids. The peptides are numbered (Xphy) according to appearance (retention times) in the HPLC runs.
Phytase peptides (phy) obtained by trypsin digestion.

| [SEQ ID No.: :] | Peptide No. (name) | Amino Acid Sequence[a] [Amino Acid Sequence Deduced from DNA sequence][b] |
|---|---|---|
| [:33:] | 248 (not pure) | Val—Leu—Val—Asn—Asp [not possible to compare to DNA] |
| [:34:] |  | Tyr Glu Ser Leu Gln |
| [:35:] | 784 (9 phy) | Tyr—Glu—Ser—Leu—Thr—Arg [Tyr—Glu—Ser—Leu—Thr—Arg] |
| [:36:] | 675 (not pure) | Ser—Ala—Ala—Ser—Leu—Asn—Ser (a fragment of the trypsin enzyme) |
| [:37:] |  | Leu—Lys—Asp—Pro—Arg [Leu—Lys—Asp—Pro—Arg] |
| [:38:] | 783 (not pure) | Val—Ile—Ala—Ser—Gly—Glu—Lys [small amount = #670 and 796, above] |
| [:39:] | (4 phy) | Tyr—Pro—Thr—Glu—Ser—Lys [Tyr—Pro—Thr—Glu—Ser—Lys] |
| [:40:] | 244 (not pure) | Tyr Phe Asn X Gly [not possible to compare to DNA] |
|  |  | Asp Pro Ala X |
| [:41:] | 793 | Leu—Glu—Asn/Pro—Asp/Phe—Leu—Asp/Ser—Gly/Leu—Phe/Val—Thr—Leu—) |
| [:42:] |  | [Leu—Glu—Asn—Asp—Leu—Ser—Gly—Val—Thr—Leu—Thr] |
| [:43:] | 792 (double sequence) | Tyr—Tyr—Gly—His—Gly—Ala—Gly—Asn—Pro—Leu—Gly—Pro—Thr—Gln—Gly—Val— Gly/Tyr—Ala—Asn—Glu— |
| [:44:] | (15 phy) | Leu—Ile—Ala (= #132 (half of above), and From this double sequence, the following sequences can be deduced |
| [:45:] |  | Val—Thr—Phe—Ala—Gln—Val—Leu—Ser [Val—Thr—Phe—Ala—Gln—Val—Leu—Ser] and Tyr—Tyr—Gly—His—Gly—Ala—Gly—Asn—Pro—Leu—Gly—Pro—Thr—Gln—Gly— Val—Gly [Tyr—Tyr—Gly—His—Gly—Ala—Gly—Asn—Pro—Leu—Gly—Pro—Thr—Gln—Gly—Val— Gly] Tyr—Ala—Asn—Glu—Leu—Ile—Ala [Tyr—Ala—Asn—Glu—Leu—Ile—Ala] |
| [:46:] | 800 (13 phy) | Phe—Ile—Glu—Gly—Phe—Gln—Ser—Thr [Phe—Ile—Glu—Gly—Phe—Gln—Ser—Thr] |
| [:47:] | 797 (13 phy) | Asp/Asn—Tyr—Leu—Gln—Ser—Leu—Lys [Asp—Tyr—Leu—Gln—Ser—Leu—Lys] |
| [:48:] | 795 | (Odd behavior in peptide sequencing) Asn—Ile—Glu—Pro—Phe—Gln—Val— Asn [not found in DNA sequence.] |
| [:49:] | 799 (8 phy) | Val—Leu—Val—Asn—Asp—Arg {= #248, above} [Val—Leu—Val—Asn—Asp— Arg] |
| [:50:] | 1081 (Nphy) | Leu—Ala—Val—Pro—Ala—Ser—(Arg)—Asp—Gln—Ser—Thr—X—Asp—Thr [Leu—Ala—Val—Pro—Ala—Ser—Arg—Asn—Gln—Ser—Thr—Cys—Asp—Thr] |
| [:51:] | C-terminal (Cphy) | —(Arg)—Ser—Ala—OH [Cys—Ser—Ala—End] |

[a]peptide sequence X = amino acid not determined; slash (/) = either one or the other of the two indicated amino acids may be present, the assay was not definitive, ( ) = the presence of the amino acids in parenthesis is subject to question because of a weak signal of the PTH amino acid;
[b][ ] = [peptide sequence deduced from DNA sequence, and #: peptide number for identification

TABLE 4 pH 2.5 acid phosphatase peptide sequences generated by either trypsin (T) or endoproteinase Lys—Cys digestion of purified enzyme. Corresponding nucleotide positions are also listed

| Peptide Number | Peptide Sequence | Nucleotide Position |
|---|---|---|
| N-terminal #817;74pho [SEQ ID No.:53:] | FSYGAAIPQSTQEK | 193 . . . 234 |
| #941;10/0pho [SEQ ID No.:54:] | QFSQEFRDGY | 235 . . . 264 |
| #938 [SEQ ID No.:55:] | YGGNGPY | 280 . . . 300 |
| #1111 [SEQ ID No.:56:] | VSYGIA | 310 . . . 327 |
| #816;1Lpho [SEQ ID No.:57:] | RHGERYPSPSAGK | 376 . . . 414 |
| #847 [SEQ ID No.:58:] | DIEEALAK | 415 . . . 438 |
| #943-1;11 Lpho | ARYGHLWNGET | 595 . . . 627 |
| [SEQ ID No.:59:] #943-2;11bpho | VVPFFSSG | 628 . . . 651 |
| [SEQ ID No.:60:] #1106;3Tpho | FSSGYGR | 640 . . . 660 |
| [SEQ ID No.:61:] #1110-1 | QLPQFK | 826 . . . 843 |
| [SEQ ID No.:62:] #1108 | VAFGNPY | 1384 . . . 1404 |
| [SEQ ID No.:63:] |  |  |

Example 5

The Cloning and Sequencing of the pH 2.5 Optimum Acid Phosphatase Gene from *Aspergillus niger*

I. SUMMARY

The gene for pH 2.5 optimum acid phosphatase has been cloned and sequenced from *Aspergillus niger*. Translated nucleotide sequence yielded a polypeptide of 479 amino acids for the pH 2.5 acid phosphatase. The gene for this protein was isolated using oligonucleotide probes based on the peptide sequence of the purified protein.

II. EXPERIMENTAL AND DISCUSSION

A. Design of oligonucleotide probes

Isolation of the gene encoding pH 2.5 acid phosphatase (AP) was made through hybridization of degenerate oligonucleotides designed from peptide sequences. Several internal peptide fragments had been isolated previously and sequenced from purified pH 2.5 AP from *A. niger* var. awamori strain ALKO 243 (ATCC 38854) as described earlier in this patent.

A 17mer degenerate oligonucleotide, PHY-31, was designed from acid phosphatase peptide #816(1Lpho in Table 4 [SEQ ID No. :57:]). Through the incorporation of a neutral inosine, one perfect match out of 64 possible combinations exists in PHY-31. The nucleotide sequence of oligonucleotide PHY-31 and corresponding peptide sequence is shown in FIG. 1.

B. Hybridization specificity of the oligonucleotide probes

In order to evaluate the specificity of the degenerate oligonucleotides, they were end labelled with [γ-$^{32}$P]-ATP to a high specific activity using *E. coli* polynucleotide T4 kinase (BRL) and used to probe total genomic DNA from ALKO 243. Genomic DNA was isolated by a neutral lysis method. Briefly, finely ground frozen dried mycelia was lysed with a 4% SDS-TE buffer. Cell debris was removed and supernatant was removed and extracted twice with an equal volumn of Tris-saturated phenol:chloroform (1:1). Genomic DNA was precipitated with NH$_4$OAC and EtOH. Pelleted DNA was purified by ultracentrifugation through CsCl and recovered as described by Maniatis et al. *Molecular Cloning, A Laboratory Manual*, Cold Spring Harbor Laboratory, Cold Spring Harbor, N.Y., USA (1982)). Hybridization to genomic DNA with [γ$^{32}$P] ATP labelled degenerate oligonucleotides (Maniatis et al. *Molecular Cloning, A Laboratory Manual*, Cold Spring Harbor Laboratory, Cold Spring Harbor, N.Y., USA (1982)) was done at 42° C. overnight on filters in oligonucleotide hybridization solution (6× SSPE, 0.5% SDS, 3× Denhardts, 100 µg/ml tRNA). Non-specific binding was removed by washing the filters twice for 30 minutes at room temperature with 2XSSC, 0.1% SDS, and once for 5 minutes at 42° C. in fresh solution. Overnight exposure on Kodak X-Omat AR film with intensifying screens revealed positively hybridizing bands.

*A. niger* ALKO 243 genomic DNA was probed with pH 2.5 oligonucleotide PHY-31. Hybridization was performed as described above. Among the oligonucleotides for pH 2.5 AP, only PHY-31 gave relatively specific hybridization to genomic DNA. Hybridization to one predominant and one minor band indicated sufficient specificity to use for screening the libraries.

C. Isolation and characterization of the pH 2.5 Acid Phosphatase gene

Genomic DNA was partially digested with Sau3A in order to produce fragments 10–23 kb in length. Digested DNA was ligated to BamHI-cut dephosphorylated Lambda Dash II vector arms (Stratagene). The ligated DNA was packaged in vitro using Gigapack Gold packaging extracts (Stratagene). Packaged phage was used to infect *E. coli* strain P2392. The lambda library was screened with oligonucleotide PHY-31 for the pH 2.5 AP gene under the conditions established with genomic hybridizations in section (B). Twelve hybridizing plaques were picked for further characterization. Bacteriophage DNA isolated from each of the candidates was digested with restriction endonucleases and probed with either PHY-31 or a mixture of PHY-34 and PHY-35 which were derived from an independent pH 2.5 AP peptide (FIG. 1). One of the clones, AP99, contained a 2.1 kb SphI fragment previously identified in genomic Southern analysis, that hybridized strongly to both probes. Strong hybridization to two oligonucleotides derived from different peptide sequences suggested that AP99 contained pH 2.5 AP coding sequences. This 2.1 kb SphI fragment was therefore subcloned into M13mp18 and M13mp19 for sequencing. Translation of the nucleotide sequence of this subclone revealed the peptide sequences including the N-terminal peptide (Table 4). Immediately upstream of the N-terminal peptide is a typical fungal secretion signal sequence beginning with a methionine initiation codon at position 136. All of the peptide sequences were present in a single ORF except #1108 (Table 4 [SEQ ID No. :63] which begins at nucleotide position 1384. Termination codons were identified in all three reading frames between nucleotides 1151 and 1384. These results necessitated the inclusion of an intron(s) in the 3' portion of the gene.

Figure 2B:
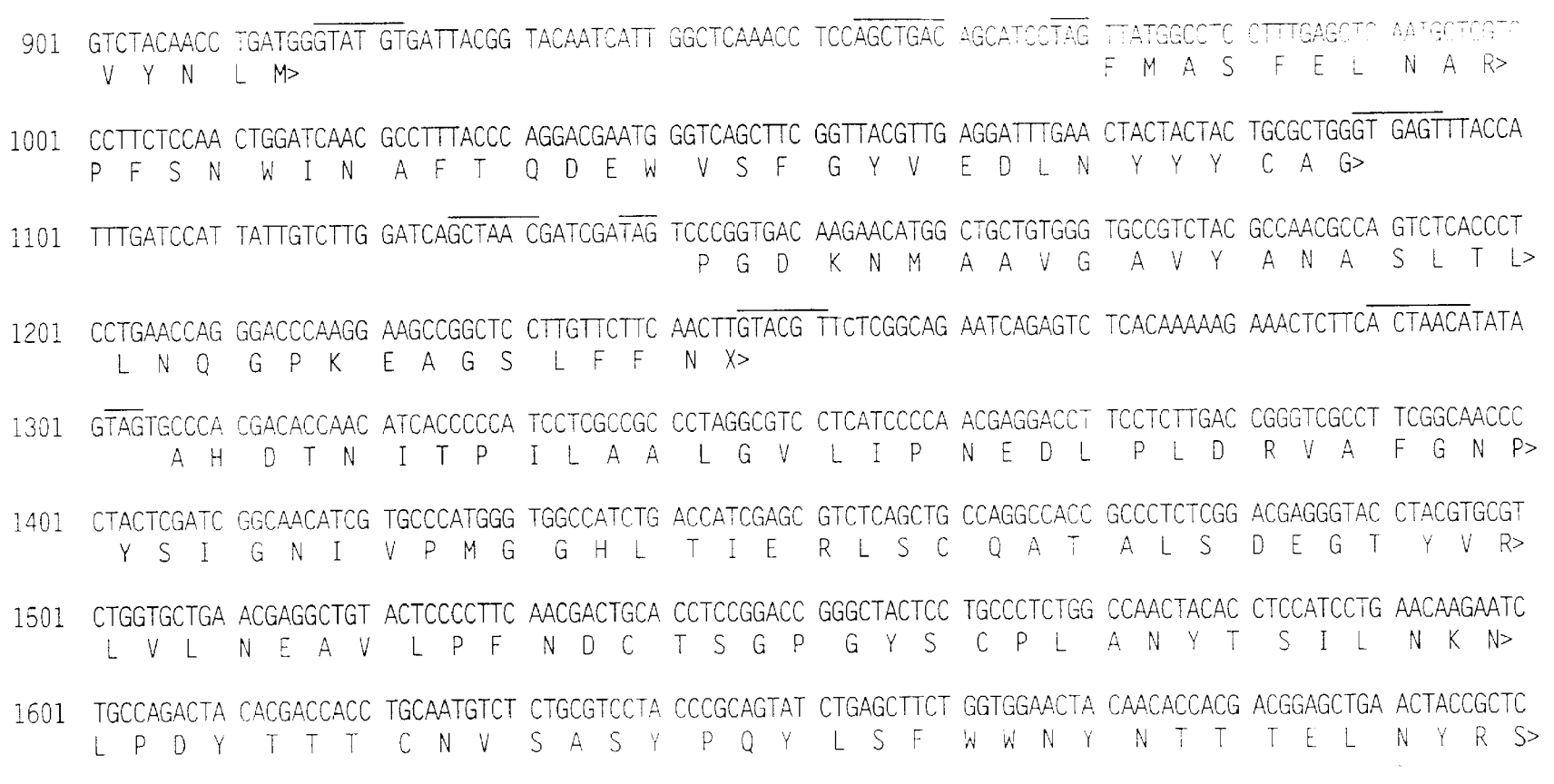

Identification of intron boundaries was made through the isolation and sequencing of pH 2.5 AP cDNA. The 3' region of pH 2.5 AP gene was isolated from the corresponding cDNA by PCR amplification using pH 2.5 AP specific primers. *A. niger* var. awamori ALKO 243 was grown in RNA broth media consisting per liter of 2.0% corn starch (Sigma), 1.0% protease peptone (Difco), 30.0 g glucose, 5.0 g NH$_4$NO$_3$, 0.5 g MgSO$_4$.7H$_2$O, 0.5 g KCl, 0.183 g FeSO$_4$.7H$_2$O. Total RNA was isolated essentially by the LiCl precipitation method of McAda and Douglas (McAda, P. C. et al., *Meth. Enzymol.* 97:337–344 (1983)). Polyadenylated messenger RNA was affinity purified from total RNA by the use of oligonucleotide(dT)-cellulose columns (Pharmacia) as specified by the manufacturer. Oligonucleotide PCR primers UPPHOS (5'GAATTCCGAGTCCGAGGTCATGGGCGCG-3') [SEQ ID No. :67:] and DOWNPHOS (5'-GAATTCCCGGGACCTACCCCTCTGCAT-3') [SEQ ID No. :16:] were synthesized according to genomic sequences with flanking EcoRI restriction sites. UPPHOS and DOWNPHOS are inversely oriented and are separated by 978 bases in the genomic clone. First strand synthesis was performed with the BMB cDNA kit according to the manufacturer's recommendations with 1.0 µg mRNA and DOWNPHOS. PCR amplifiction of the cDNA.mRNA complex with oligonucleotide primers UPPHOS and DOWNPHOS yielded a specific product of approximately 850 bps. PCR amplification of pAP-1 plasmid DNA with the same primers yielded the expected product of 1006 bps. Gel purified cDNA PCR product was cut with EcoRI and subcloned into pUC-18 for double-stranded sequencing using the United States Biochemical Sequenase II kit. The primers amplified an 850 bp fragment from the cDNA and the expected 1006 bp fragment from cloned genomic DNA. Sequencing of the amplified cDNA fragment revealed the presence of three short introns, each exhibiting consensus fungal donor, lariat and acceptor sequences. The coding sequence is derived by splicing the nucleotides 136–916, 971–1088, 1141–1245, and 1305–1740. The resulting translated sequence codes for a protein of 479 aa as shown in FIGS. 2(A–C).

The pH 2.5 AP polypeptide predicted from the nucleotide sequence has a calculated M$_r$ of 52,678. The 2.1 kb SphI fragment in pUC18 (pAP-1) contained 135 bp of upstream pH 2.5 AP sequence.

Example 6
*Aspergillus niger* Phytase Production in *Trichoderma reesei*
II. EXPERIMENTAL PROTOCOLS
1. Bacterial strains, phage and plasmids For subcloning and sequencing, the *E. coil* strains DH5α (Hanahan, D., "Techniques for transformation of *E. coli*," in *DNA Cloning*, vol. 1, Glover, D. M., ed., IRL Press, Oxford, pp. 109–135 (1985); Bethesda Research Laboratories, Gaithersburg, Md., USA) and XL-1-Blue (Bullock, W. O., et al., *BioTechniques* 5:376–378 (1987); Stratagene, La Jolla, Calif., USA) were used. *E. coli* Y1090 (r⁻) (Huynh, D. S., et al., "Constructing and screening cDNA libraries in λgt1 and λgt11, " *DNA Cloning*, vol. 1, Glover, D. M., ed., IRL Press, Oxford, pp. 49–57 (1985); Promega Biotec Protoclone GT System, Madison, Wis., USA) was used as a host in λgt11 phage growing.

*Aspergillus niger* var. awamori ALKO 243 (ATCC 38854) was used as a donor of the phytase gene. *T. reesei* strains ATCC56765 (RutC-30), ALKO 233 (VTT-D-791256, Bailey and Nevalainen, *Enzyme Microb. Technol.* 3:153–157 (1981)) and ALKO 2221 were used as recipients for the phytase gene. ALKO 2221 is a low aspartyl protease mutant derived from the strain ALKO 233 by UV-mutagenesis.

The phage λgt11 (Promega) was used for making the gene library. The phages were grown by the standard methods described by Silhavy et al. (Silhavy, T. J., et al., *Experiments with Gene Fusions*, Cold Spring Harbor Laboratory, Cold Spring Harbor, N.Y., USA (1984)).

As vectors for subcloning, pUC9 (Boehringer, Mannheim, FRG) and pALK307, a derivative of pIBI76 (IBI, New Haven, Conn., USA) were used. To obtain pALK307, an approximately 940 bp NaeI-PvuI fragment (actually 941 bp) has been deleted from pIBI76. This the only change in pIBI76. The plasmid pAMH110 (Nevalainen, H., et al., "The molecular biology of Trichoderma and its application to the expression of both homologous and heterologous genes," in *Molecular Industrial Mycology*, Leong and Berka, eds., Marcel Dekker Inc., New York, pp. 129–148 (1991)) contains the *Trichoderma reesei* cbh1 promoter and terminator areas. The plasmid p3SR2 (Kelly and Hynes, EMBO J. 4:475–479 (1985)) contains the *Aspergillus nidulans* acetamidase gene. p3SR2 has been kindly donated by Dr. M. Hynes (University of Melbourne, Australia).

2. Growth media and culture conditions

*E. coli* cultivations were carried out at 37° C. overnight and cultivations of filamentous fungi at 30° C. for 5 to 7 days for enzyme production and for 2 days when mycelia was grown for DNA isolation.

*E. coli* were grown in L-broth (Maniatis, T., et al., *Molecular Cloning, A Laboratory Manual*, Cold Spring Harbor Laboratory, Cold Spring Harbor, N.Y., USA (1982)) supplemented with ampicillin (50–100 μg/ml) when needed. PD agar slants (Potato Dextrose broth by Difco, Detroit, Mich., USA) were used for growing the Aspergillus and the Trichoderma strains. *Aspergillus niger* ALKO 243 mycelium for DNA extraction was grown in complete Aspergillus medium containing 2% (w/v) malt extract (Difco), 0.1% (w/v) Bacto-peptone (Difco) and 2% (w/v) glucose. The plates and media for *T. reesei* transformations were as in Penttilä et al. (Penttilä, M., et al., *Gene* 61:155–164 (1987)). The transformants were purified on selective acetamide-CsCl medium (Penttilä, M., et al., *Gene* 61:155–164 (1987)) before transferring to PD slants.

For plate screening of high phytase producers, *T. reesei* clones transformed with the cbh1 promoter/phytase fusion were grown for 3 to 5 days on Trichoderma minimal medium plates with no glucose and supplemented with 1% sodium phytate (Sigma, St. Louis, Mo., USA), 1% Solka Floc and 1% proteose peptone (Difco). When the construct containing the phytase promoter was used for transformation, screening of high phytase producers was carried out on plates containing 1% sodium phytate and 1% proteose peptone but no sodium phosphate.

For phytase production *A. niger* ALKO 243 was grown for 5 days in a soy flour medium containing glucose and mineral salts (all from Merck, Darmstadt, FRG); the pH was adjusted to 5.0. For phytase expression from the cbh1 promoter, *T. reesei* transformants were grown for 7 days (250 rpm) in a lactose based cultivation medium. For growing the *T. reesei* transformed with the fragment containing the phytase promoter, Trichoderma minimal medium was supplemented with 50 g/l soy flour and no sodium phosphate was added.

The contents of the soy flower medium are as follows (per liter): 50 g of soy flower, 30 g glucose, 5.0 g $NH_4NO_3$, 0.5 g $MgSO_4.7H_2O$, 0.5 g KCl, 0.183 g $FeSO_4.7H_2O$, at pH 5.0. The lactose based cultivation medium contains: 4% whey, 1.5% complex nitrogen source, 1.5% $KH_2PO_4$, 0.5% $(NH_4)_2SO_4$, at pH 5.5.

3. DNA preparations

Plasmid DNA from *E. coli* (large scale) was isolated by using Qiagen columns (Diagen GmbH, Dusseldorf, FRG) according to the manufacturer's protocol. For rapid screening the method of Holmes and Quigley (*Anal. Biochem.* 114:193–197 (1981)) was used. Chromosomal DNA from Aspergillus was isolated from lyophilized mycelia as described in Clements and Roberts (*Curr. Genet.* 9:293–298 (1986)) and in Raeder and Broda (*Lett. Appl. Microbiol.* 1:17–20 (1985)).

4. Cloning procedures

The standard DNA methods described by Maniatis et al. (*Molecular Cloning, A Laboratory Manual*, Cold Spring Harbor Laboratory, Cold Spring Harbor, N.Y., USA (1982)) were mainly used. The restriction enzymes, T4-DNA-ligase, Klenow fragment of DNA polymerase I, T4 DNA polymerase, polynucleotide kinase and EcoRI methylase used in the DNA manipulations were from Boehringer (Mannheim, FRG) and New England Biolabs (Beverly, Mass., USA). Mung bean nuclease was from BRL (Gaithersburg, Md., USA) and ExoIII from Pharmacia (Uppsala, Sweden). Each enzyme was used according to the supplier's instructions.

For making the gene bank the chromosomal DNA was partially digested with HaeIII. EcoRI methylase treatment, size fractionation and packaging were done as in Paloheimo et al. (Paloheimo, M., et al., *Appl. Microbiol. Biotechnol.* 36:584–591 (1992)). Fragments of a size of 2–8 kb were used for construction of the gene bank.

Subcloning into the plasmid vector was done by using standard DNA methods (Maniatis, T., et al., *Molecular Cloning, A Laboratory Manual*, Cold Spring Harbor Laboratory, Cold Spring Harbor, N.Y., USA (1982)). DNA fragments for cloning or transformations were isolated from low-melting-point agarose gels (FMC Bioproducts, Rockland, Me., USA) by the freeze-thaw-phenol method (Benson, S. A., *Bio/Techniques* 2:66–68 (1984)) or by using the GeneClean® or Mermaid™ Kits (BIO 101 Inc., La Jolla, Calif., USA) according to the supplier's instructions.

Sequencing was carried out directly from the plasmids by the Sanger method (Sanger, F., et al., *Proc. Natl. Acad. Sci. USA* 74:5463–5467 (1977)) by means of SP6, 17, pUC/M13 primers and extension primers and the Promega Sequenase sequencing kit (United States Biochemical Corporation, Cleveland, Ohio, USA). Fusions between the cbh1 promoter and the phytase gene were sequenced by automated sequencer (Applied Biosystems 373A, Foster City, Calif., USA) using Taq DyeDeoxy™ Terminator Cycle Sequencing Kit (Applied Biosystems). The oligonucleotides used were synthesized by an Applied Biosystems 381A Synthesizer except the pUC primers that were purchased from the United States Biochemical Corporation.

DNA probes were labeled by using the non-radioctive DIG-DNA Labelling and Detection Kit by Boehringer according to the supplier's instructions.

Hybridizations were done at 68° C. as in supplier's instructions (Boehringer). Amersham's Hybond N nylon filters were used in the plaque screenings and in the Southern blot hybridizations.

When the plaques were screened with an antiserum, a phytase specific polyclonal antiserum KH1236 was used. KH1236 was made against purified and deglycosylated phytase preparation (M. Turunen, Alko Ltd.) in the National Public Health Institute (Helsinki, Finland). Anti-rabbit-IgG alkaline phosphate conjugate and color development substrates from ProtoBlot™ Immunoblotting system (Promega) were used to detect the immunocomplexes.

5. Transformations

E. coli strains were transformed according to the method of Hanahan ("Techniques for transformation of E. coli," in DNA Cloning, vol. 1, Glover, D. M., ed., IRL Press, Oxford, pp. 109–135 (1985)), and T. reesei strains as in Penttilä et al. (Gene 61:155–164 (1987)). When the ligated fragments were transformed (the D-transformation in Table 7) the ligation mixture was not further purified but was used as such in the transformations. Prior to sporulating on potato dextrose agar (PD) slants T. reesei transformants were transferred on the selective medium and purified through conidia.

6. Enzyme and protein measurements

For the enzyme assays T. reesei mycelium was separated from the culture medium by centrifuging for 15 to 30 min at 5,000 to 10,000 rpm (Sorvall SS-34, Dupont Company, Wilmington, Del., USA). A. niger cultures were centrifuged for 40 min at 10,000 rpm (Sorvall SS-34). The phytase activity was measured from the culture supernatant as the amount of inorganic phosphate released by enzymatic hydrolysis of sodium phytate substrate at 37° C. as described earlier. One phytase normalized unit (PNU) is defined as the amount of phytase activity produced by the A. niger ALKO 243 strain under the cultivation conditions used.

The phytase production on the sodium phytate assay plates was visualized by pouring the reagent C (3:1:1 ratio of 1M $H_2SO_4$, 2.5% ammonium molybdate, 10% ascorbic acid) on the plates and incubating them at 50° C. for 15 minutes. The reduction of the phosphomolybdate complex leads to bluish color.

Amyloglucosidase activity (AGU) was measured by using 1% Zulkowsky starch (Merck) as a substrate and measuring the amount of the released glucose units by boiling with DNS reagent (see below) after 10 min of reaction at 60° C. at pH 4.8. Proteases (HUT) were measured at pH 4.7 as in Food Chemicals Codex (1981) by using 2% haemoglobin (Sigma) as a substrate. Endoglucanase (ECU) and cellobiohydrolase (FPU) activities were measured as in IUPAC's Measurement of Cellulase Activities (IUPAC Commission on Biotechnology, Measurement of Cellulase Activities, Biochemical Engineering Research Centre, Indian Institute of Technology, Delhi, India, pp. 5–7 and 10–11 (1981)). 1% hydroxyethylcellulose (Fluka AG) in 50 mM sodium-citrate buffer (pH4.9) and Whatman no. 1 paper were used as substrates, respectively. DNS used differed from that described at the IUPAC's protocol and was made by first diluting 50.0 g 2-hydroxy-3,5-dinitrobenzoic acid (Merck) into 4 l of deionized water. Then, 80.0 g NaOH was added slowly by using the magnetic stirrer and 1,500 g sodium-potassium tartrate (Merck) was added and diluted by heating the solution (maximum temperature 45° C.). The total volume was adjusted to 5 l, the solution was filtered through Whatman no. 1 and was protected from light.

CBHI protein was measured from the culture supernatant by running a SDS-polyacrylamide gel and detecting the CBHI protein band (T. reesei ALKO 233 and ALKO 2221 strains) or by dot blotting samples using the Schleicher & Schuell's (Dassel, FRG) Minifold™ Micro-Sample Filtration Manifold (T. reesei ATCC56765). CBHI protein was detected by using CBHI specific monoclonal antibody CI-89 (Aho, S., et al., Eur. J. Biochem. 200:643–649 (1991)) and anti-mouse-IgG alkaline phosphate conjugate (Promega). Visualization of the immunocomplexes was done as in the plaque screening.

7. SDS-PAGE and Western blot analysis

Sodium dodecyl sulphate-polyacrylamide gel electrophoresis (SDS-PAGE) and Western blot analysis were done as in Laemmli (Laemmli, U. K., Nature 227:680–685 (1970)) and as in Towbin et al. (Towbin, H., et al., Proc. Natl. Acad. Sci. USA 76:4350–4354 (1979)). Visualization of the phytase protein in Western blots was done by using the polyclonal rabbit antiserum KH1236. Visualization of the immunocomplexes was done as in the plaque screening.

8. Polymerase Chain Reaction (PCR)

The PCR reactions were performed by Techne Thermal Cycler PHC-2 (Techne Ltd., Cambridge, UK) in 100 μl volumes. The reaction mixtures contained 0.2 mM of each dNTP (3'-deoxynucloside-5'-triphosphate, Pharmacia) in 10 mM Tris buffer (pH 8.3), 50 mM KCl, 1.5–2.0 mM $MgCl_2$ and 0.01% (w/v) gelatin. The protocol used was the following: 95° C. (plasmid) or 100° C. (chromosomal DNA)/5 min before adding the Taq DNA polymerase (1–2 units, Cetus Corp., Emeryville, Calif., USA) and 100 μl overlay of paraffin oil, denaturation 95° C./1 min, annealing 60° C./1 min (in the inverse PCR 52° C.), extension 72° C./2 min (in the inverse PCR 2.5 min) for 30 cycles. The final extension time was 9 min to ensure completion of the strand synthesis. When a plasmid or DNA fragment was used as a template, the amount of the template used was 5–10 ng and 20–50 pmol of each primer was added. When chromosomal DNA was used as a template, the corresponding amounts used were 100 ng and 50–100 pmol. The circular template for the inverse PCR was done from the digested chromosomal DNA as in Innis et al (Ochman, H., et al., "Amplification of flanking sequences by inverse PCR," in PCR Protocols, A Guide to Methods and Applications, Innis, M. A., et al., eds., Academic Press, San Diego, pp. 219–227 (1990)). PCR fragments were purified by GeneClean® or Mermaid™ Kit (from an agarose gel if needed) or by Qiagen tips. The ends of the fragments were filled by using the DNA polymerase I Klenow fragment.

II. RESULTS

A. Molecular cloning of the Aspergillus niger phytase

1. Production of the phytase probe by nested PCR amplification

The oligonucleotide primers used in the PCR reactions and the corresponding amino acid sequences of the phytase ALKO 243 peptides #792 (phy 15) and #420 (phy 10) (Table 3, as described earlier) are shown in FIG. 3 (nucleotides 1409–1480 and 1727–1762 in the phytase sequence, see FIGS. 5(A–D). Two primary PCR reactions were done. In reaction A, sense oligonucleotide 1 (#792) and antisense oligonucleotide 4 (#420) were used; in reaction B, sense oligonucleotide 3 (#420) and antisense oligonucleotide 2 (#792) were used. Primary PCR reaction A gave a single band of about 400 bps while PCR amplification from the reaction B gave no product. Thus it was concluded that the region coding for the peptide #792 was located on the 5'-side in the phytase sequence compared to that coding for the peptide #420. The primary PCR fragment (A) was used as a template for the second PCR with internal primers from the peptide sequences: sense oligonucleotide 2 and antisense oligonucleotide 3. PCR amplification from the second PCR reaction gave a specific product of about 350 bps. The PCR fragment was cloned to SmaI digested pUC9 and sequenced. The amino acid sequence deduced from the DNA sequence contained also the known amino acids from the peptide #792 and #420 that were not coded by the primer sequences. The approximately 350 bp PCR fragment was used to probe the DNA bank.

2. Screening of the DNA bank

The gene bank contained approximately $1.9 \times 10^6$ pfu (plaque forming units)/ml, of which approximately 99.5% had an insert. From about 80,000 plaques that were screened, two positive clones Hae2–6 and Hae1–5 were found. The clones were isolated, purified and the inserts (5.6 and 5.2 kb) were subcloned to EcoRI cut pALK307. The clones also reacted with the phytase antiserum KH1236. The inserts were restriction mapped and the PCR fragment was found to hybridize to the about 1 kb BamHI-SphI restriction fragment of the clones (see FIG. 4 for the hybridization area in the phytase sequence). The sequence of the clone Hae2–6 that contained more of the 5'-sequence coded for 15 internal tryptic peptide sequences but the N-terminal amino acid sequence was not found. The N-terminal and the promoter area containing phage clones were screened from the gene bank by using a 5'-probe made by inverse PCR (Ochman, H., et al., "Amplification of flanking sequences by inverse PCR," in *PCR Protocols, A Guide to Methods and Applications*, Innis, M. A., et al., eds., Academic Press, San Diego, pp. 219–227 (1990)).

3. Amplification of the 5'-end and the promoter sequence of the phytase gene by inverse PCR Restriction enzyme digestions of the genomic DNA and Southern hybridizations with the 350 bp PCR probe showed that digestions of the genomic DNA with SalI produced fragments of suitable size (1–3 kb) for circularization and amplification with PCR. The primers used for inverse PCR were from bases 1243–1257 (antisense primer) and 1304–1321 (sense primer) areas of the phytase sequence (see FIGS. 5(A–D)). Inverse PCR with SalI digested ALKO 243 DNA created a PCR band of about 1.2 kb. The 350 bp PCR fragment hybridized to the inverse PCR fragment and by sequencing the subcloned fragment it was confirmed that it contained the upstream parts of the phytase gene and also the N-terminal peptide sequence was included.

4. Isolation of the complete phytase gene

The 1.2 kb PCR fragment obtained from the inverse PCR was used as a probe to screen 80,000 plaques from which seven positive plaques could be identified. The complete phytase gene was isolated on an about 6 kb insert of a phage clone.

The about 2.4 kb SphI fragment containing the phytase gene and the promoter area was subcloned into pALK307 (cut with SphI) to give pALK169 (FIG. 4). The restriction map of the phytase containing SphI fragment and the location of the phytase gene in the fragment are shown in the plasmid map.

The phytase sequence is shown in FIGS. 5(A–D). The sequence coding for the phytase protein corresponds to the phytase sequence of *Aspergillus ficuum* published in the Gist brocades (Delft, Netherlands) PCT patent application (EP420,358 or WO91105053) with 12 differences in the deduced amino acids. Each difference in the deduced amino acid was due to one nucleotide's change and might be due to differences between the strains. Also, in the sequence coding for the structural gene, 33 nucleotide differences were found that did not lead to differences in the deduced amino acid sequence. In the signal sequence, there were differences in two nucleotides (the other lead to a difference in the deduced amino acid) and in the proposed intron area 8 differences could be found. The overall match per length (nucleotide sequences from the first ATG to the STOP codon TAG) between the two sequences was 96.3%. The differences found between the two phytase sequences, Gistbrocades' and Alko's, are shown in the Table 5.

TABLE 5

Nucleotide and amino acid differences between Gist's and Alko's phytase sequences.

| area | nt no | as no | Gist's nt(s) | Alko's nt(s) | Gist's aa | Alko's aa |
|---|---|---|---|---|---|---|
| signal | 39 | (−7) | CTG | CTA | Leu | Leu |
| sequence | 40 | (−6) | TCT | GCT | Ser | Ala |
| proposed | 59 | (−) | A | G | (−) | (−) |
| intron | 61 | (−) | A | T | (−) | (−) |
| | 65 | (−) | A | T | (−) | (−) |
| | 72 | (−) | A | G | (−) | (−) |
| | 85 | (−) | C | T | (−) | (−) |
| | 86 | (−) | C | T | (−) | (−) |
| | 88 | (−) | T | G | (−) | (−) |
| | 136 | (−) | T | A | (−) | (−) |
| structural | 191 | 11 | AGT | ACT | Ser | Thr |
| gene | 210 | 17 | CAG | CAA | Gln | Gln |
| | 258 | 33 | GCA | GCG | Ala | Ala |
| | 287 | 43 | GTC | GCC | Val | Ala |
| | 300 | 47 | GAG | GAT | Glu | Asp |
| | 312 | 51 | GGA | GGT | Gly | Gly |
| | 369 | 70 | GAC | GAG | Asp | Glu |
| | 419 | 87 | GCG | GTG | Ala | Val |
| | 369 | 91 | GAC | GAT | Asp | Asp |
| | 501 | 114 | GAA | GAG | Glu | Glu |
| | 549 | 127 | CGG | CGA | Arg | Arg |
| | 565 | 136 | GTT | ATT | Val | Ile |
| | 570 | 137 | CCA | CCG | Pro | Pro |
| | 613 | 152 | AAG | GAG | Lys | Glu |
| | 624 | 155 | ATC | ATT | Ile | Ile |
| | 669 | 170 | CCC | CCG | Pro | Pro |
| | 756 | 199 | TTC | TTT | Phe | Phe |
| | 809 | 217 | GTC | GCC | Val | Ala |
| | 846 | 229 | TCC | TCT | Ser | Ser |
| | 849 | 230 | GGT | GGC | Gly | Gly |
| | 976 | 273 | AAC | CAC | Asn | His |
| | 997 | 280 | TTG | CTG | Leu | Leu |
| structural | 1005 | 282 | AAG | AAA | Lys | Lys |
| gene | 1008 | 283 | TAT | TAC | Tyr | Tyr |
| | 1020 | 287 | GGT | GGC | Gly | Gly |
| | 1083 | 308 | CTG | CTC | Leu | Leu |
| | 1113 | 318 | AGT | AGC | Ser | Ser |
| | 1125 | 322 | ACT | ACC | Thr | Thr |
| | 1136 | 326 | AGC | AAC | Ser | Asn |
| | 1140 | 327 | CCG | CCA | Pro | Pro |
| | 1149 | 330 | TTT | TTC | Phe | Phe |
| | 1182 | 341 | TCG | TCC | Ser | Ser |
| | 1185 | 342 | CAT | CAC | His | His |
| | 1188 | 343 | GAC | GAT | Asp | Asp |
| | 1203 | 348 | TCC | TCT | Ser | Ser |
| | 1206 | 349 | ATT | ATC | Ile | Ile |
| | 1218 | 353 | TTA | TTG | Leu | Leu |
| | 1245 | 362 | CTA | CTG | Leu | Leu |
| | 1284 | 375 | GGA | GGG | Gly | Gly |
| | 1321 | 388 | TTG | CTG | Leu | Leu |
| | 1344 | 395 | TGT | TGC | Cys | Cys |
| | 1350 | 397 | GCG | GCC | Ala | Ala |
| | 1413 | 418 | CCG | CCA | Pro | Pro |

TABLE 5-continued

Nucleotide and amino acid differences between Gist's and Alko's phytase sequences.

| area | nt no | as no | Gist's nt(s) | Alko's nt(s) | Gist's aa | Alko's aa |
|------|-------|-------|--------------|--------------|-----------|-----------|
|      | 1414  | 419   | GTT          | ATT      | Val       | Ile   |
|      | 1499  | 447   | TTT          | TCT      | Phe       | Ser   |

Nucleotide and amino acid differences between Gist's and Alko's phytase sequences. The nucleotide numbers are counted from the first-Met (ATG) in the signal sequence and amino acid numbers from the N-terminal Leu (see FIG. 5 (A-D). The amino acids, if different between the two sequences, are written by bold letters.

B. Construction of the plasmids for overexpression of phytase in *Trichoderma reesei*

1. The PCR fragments for the precise cbh1-phytase fusions

The fusions between the cbh1 promoter and the phytase signal sequence, and between the cbh1 signal sequence and the phytase gene were done by PCR. The phytase signal sequence or the phytase protein N-terminal sequence start precisely where the corresponding cbh1 sequences would start (for the cbh1 sequence, see Shoemaker, S., et al., *Bio/Technology* 1:691–696 (1983)). The primers used for the PCR fragments are shown in FIG. 6. To construct pALK171 (phytase signal sequence), we made use of the SacII site in the cbh1 promoter area in the 5'-PCR primer. The XhoI site (14 nucleotides from the N-terminal of the phytase gene) was used in the 3'-primer. The 5'-primer was a 39-mer that contained a "tail" of 19 nucleotides of the cbh1 promoter sequence (preceding the signal sequence) and 20 nucleotides from the phytase signal sequence. The 3-primer was a 22-mer. In the construction of pALK172 (cbh1 signal sequence), we made use of the SfiI site in the cbh1 signal sequence in the 5'-primer and SalI site of the phytase (762 nucleotides from the N-terminal) in the 3'-primer. In this case, the 5'-primer was a 46-mer containing a "tail" of 28 nucleotides and 18 nucleotides of the phytase N-terminal sequence; the 3'-primer was a 24-mer. In all the primers, three to five extra nucleotides were added to the ends of the PCR fragments after the restriction site sequences to ensure a correct cut. pALK169 was used as a template in the PCR reactions.

Fragments of the expected lengths were obtained from the PCR reactions: fragment containing the wanted fusion was 202 bps for pALK171 and 800 bps for pALK172.

2. Construction of plasmids with the cbh1 promoter: pALK171 (phytase signal sequence) and pALK172 (cbh1 signal sequence)

Figure 7A:
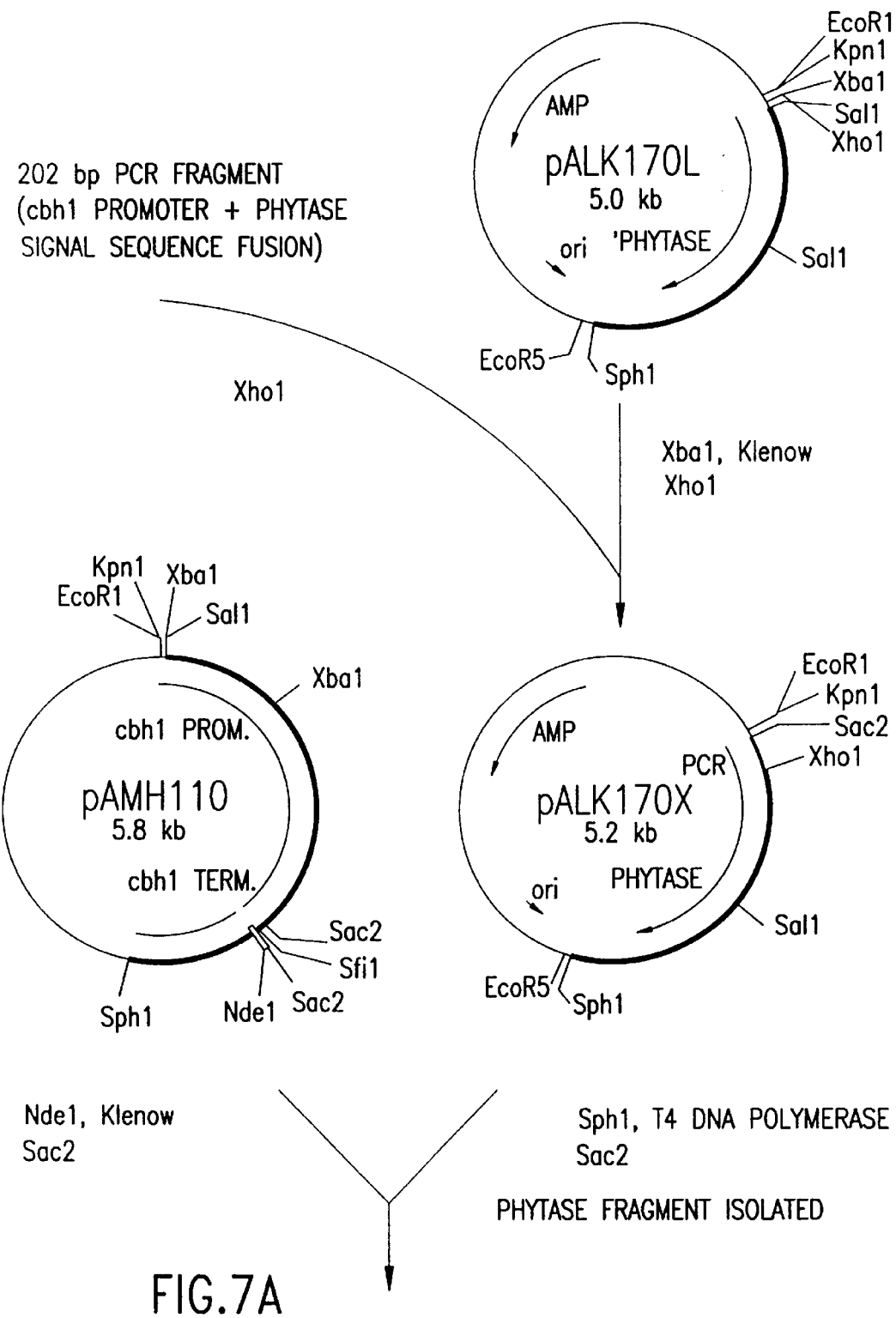
FIGS. 7(A–B). Construction of pALK171. The phytase gene with its own signal sequence was fused to the cbh1 promoter. Only the relevant restriction sites are shown.
Figure 7B:
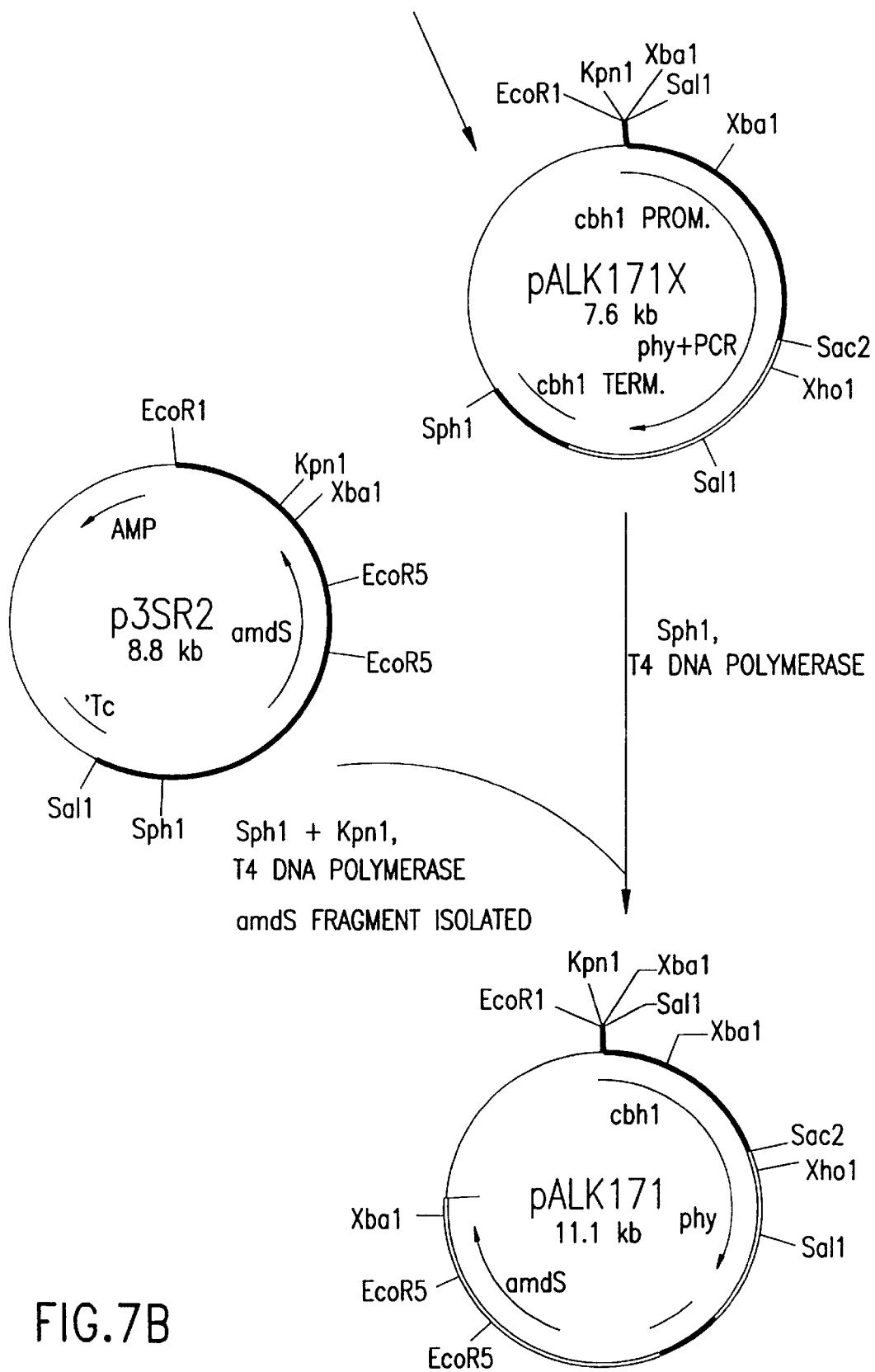
Figure 8A:
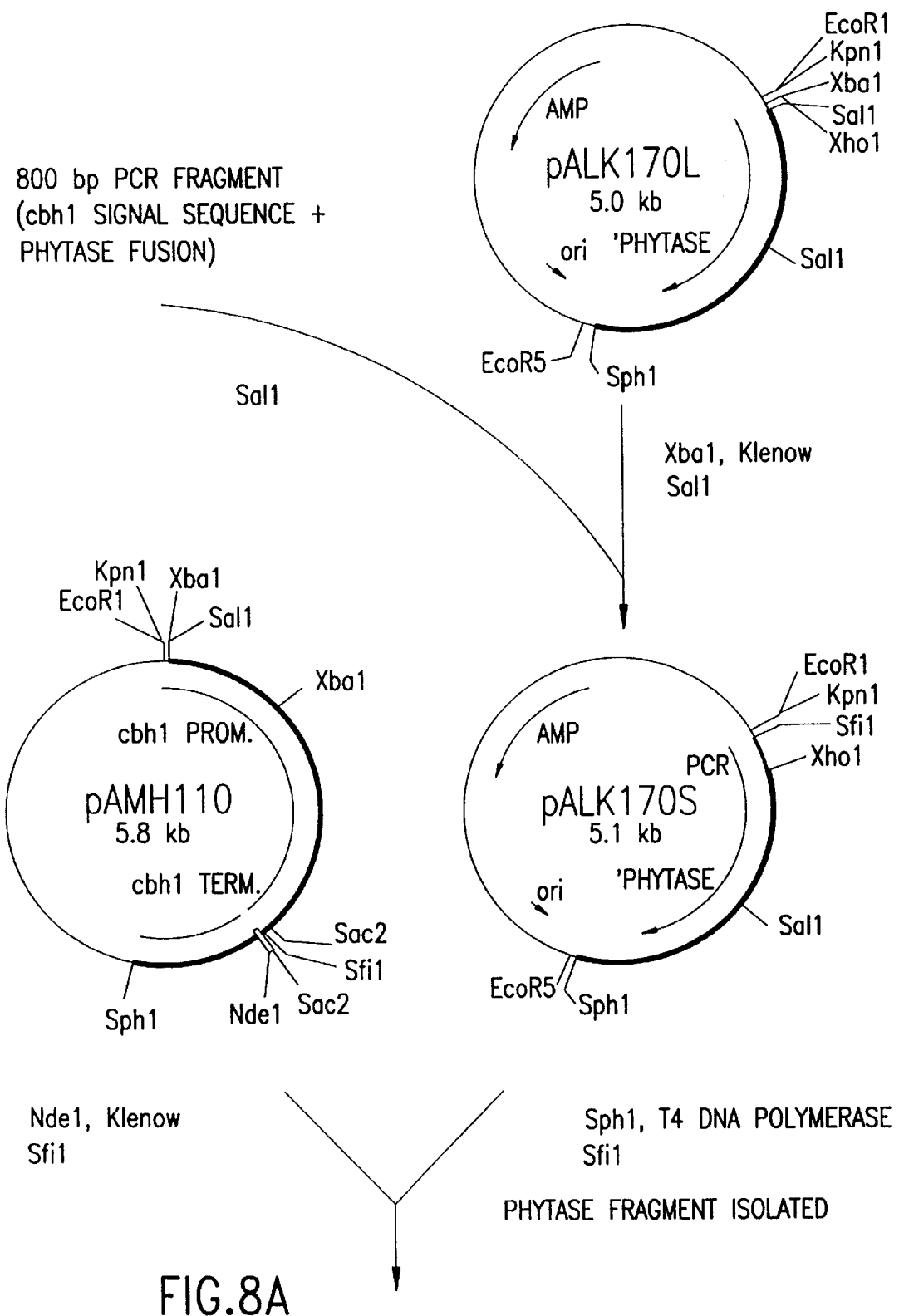
FIGS. 8(A–B). Construction of pALK172. The phytase gene was fused to the cbh1 signal sequence. Only the relevant restriction sites are shown.
Figure 8B:
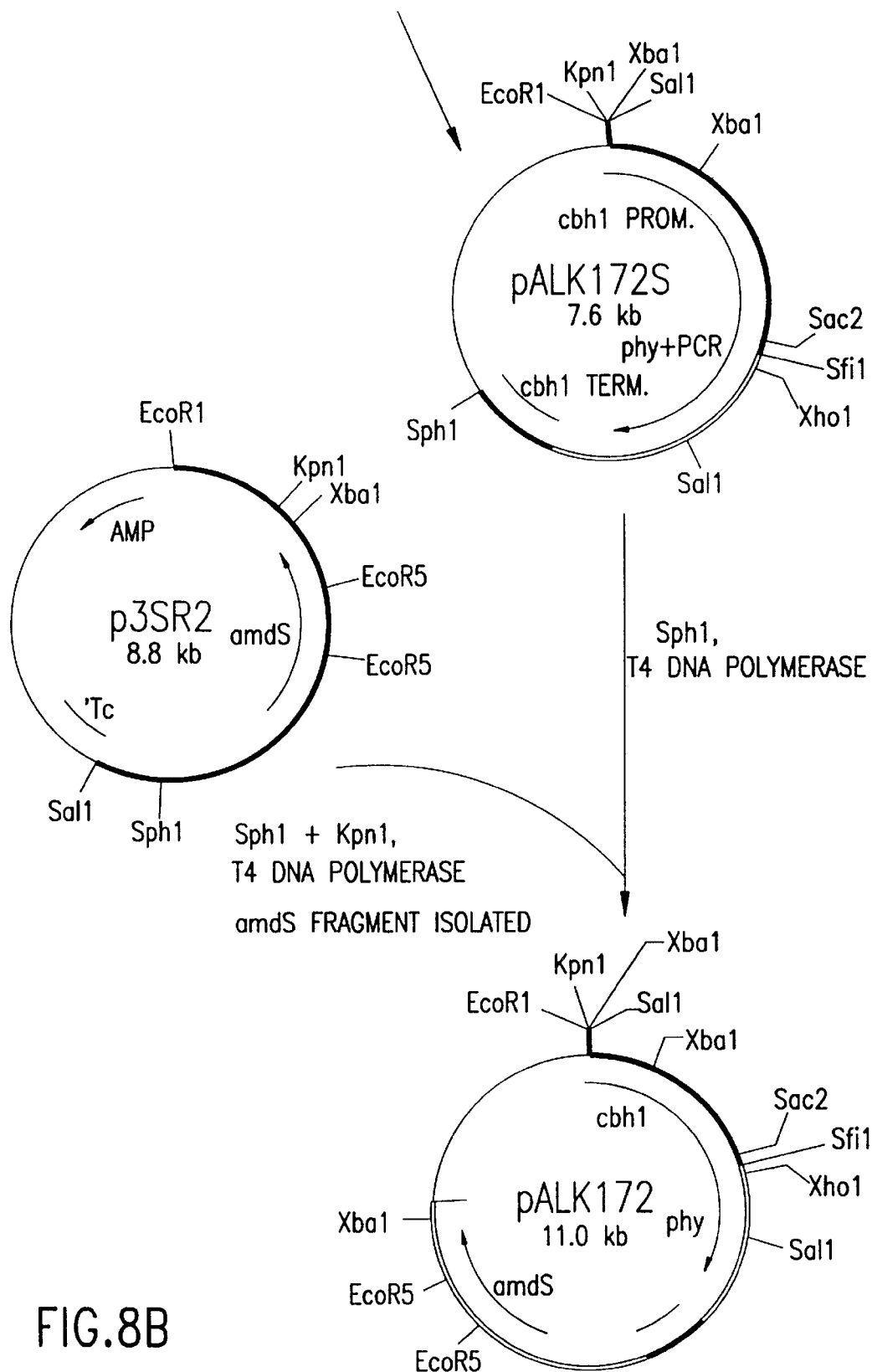

The plasmid pALK170L was made by cutting the phytase gene from pALK169 as an SphI-XhoI fragment and ligating it to SphI-XhoI cut pALK307. The 202 bp PCR fragment containing the cbh1 promoter and phytase signal sequence was cut with XhoI and ligated to pALK170L that had been cut with XbaI, treated with the DNA polymerase I Klenow fragment and cut with XhoI (pALK170X, FIGS. 7(A–B)). The fusion and the PCR fragment areas were sequenced to ensure that no mistakes had occurred in the PCR amplification. Phytase fragment containing the fusion was isolated as an SphI (treated with the T4 DNA polymerase)-SacII fragment and was inserted between the cbh1 promoter and terminator areas of the plasmid pAMH110 previously digested with NdeI (filled in with the DNA polymerase I Klenow fragment) and SacII. The plasmid obtained (pALK171X, FIGS. 7(A–B)) contains the phytase gene precisely fused to the cbh1 promoter. To construct pALK171, the amdS gene (selectable marker) was isolated from p3SR2 as a SphI-KpnI fragment, the ends were treated by the T4 DNA polymerase, and amdS was then ligated to the SphI site of pALK171X (treated with the T4 DNA polymerase). The approximately 7.5 kb linear fragment that contained no bacterial sequences was isolated from pALK171 by cutting with XbaI and was used for the transformations.

pALK172 was constructed essentially the same way as pALK171 (see FIGS. 8(A–B)). The 800 bp PCR fragment was cut with SalI and ligated to XbaI (filled in with the DNA polymerase I Klenow fragment), SalI cut pALK170L. Also in this case, the fusions and the sequence of the PCR fragment were checked by sequencing. Phytase-PCR fragment fusion was isolated from pALK170S as an SphI (treated with the T4 DNA polymerase)-SfiI fragment and ligated to pAMH110 that had been cut with NdeI (filled in with the DNA polymerase I Klenow fragment)-SfiI. To construct pALK172, the fragment containing the amdS gene was ligated to pALK172S in the same way as when constructing pALK171. XbaI was used also in this case to cut out from the vector backbone the linear fragment that was used in the transformations.

3. Construction of the plasmids with the phytase promoter: pALK173A and pALK173B The phytase gene with its own promoter was isolated as an SphI fragment from pALK169 and ligated into the KpnI site of p3SR2 (in both cases the ends of the fragments were filled in by the T4-polymerase) resulting in about 11.2 kb plasmids pALK173A and pALK173B (see FIG. 4 for pALK169 and FIGS. 7 and 8 for p3SR2 map). In pALK173A the two genes, phytase and amdS are in a parallel orientation, in pALK173B, they are in opposite orientations (FIG. 9). EcoRI was used to linearize pALK173A and pALK173B when linearized plasmids were used for transformations.

C. Transformation of *Trichoderma reesei* and screening of the transformants

*T. reesei* ATCC56765, ALKO 233 and ALKO 2221 strains were transformed with circular plasmids and with the XbaI fragments from the plasmids pALK171 and pALK172 (cbh1 promoter). *T. reesei* ALKO 233 and 2221 strains were also transformed with the linearized pALK171 and pALK172 plasmids as well as with circular and linear pALK173A and pALK173B (phytase promoter) plasmids. Transformation frequencies (transformants/μg of DNA) varied from 3 to 60 when the fragments isolated from pALK171 or pALK172 were used. When pALK171 or pALK172 circular plasmids were used in transformations, the frequencies were about 50/μg for *T. reesei* ALKO 233 and ALKO 2221 and about 100/μg for *T. reesei* ATCC56765. Transformation frequencies obtained when linearized plasmids were used were about 100/μg. When pALK173A or pALK173B were used in transformations the frequencies were from 6 to 26 for the linear plasmid and from 6 to 20 for the circular plasmid.

Regeneration frequency of the sphaeroplasts varied from 4.5% to 13.2% for *T. reesei* ALKO 233 and ALKO 2221 strains and was 1–2% for the *T. reesei* ATCC56765 strain.

The amount of the transformants that were screened for the phytase production on plates are shown in Table 6. Those clones that clearly produced a blue colored halo around the colony were counted as positive clones.

TABLE 6

Plate assay positive transformants and total number of tested clones

| Plasmid | ALKO 233 | ALKO 2221 | ATCC56765 |
|---|---|---|---|
| pALK171 | | | |
| fragment | 49% (47/96) | 46% (33/71) | 23% (15/66) |
| circular plasmid | 35% (6/17) | 23% (5/22) | 32% (22/68) |
| linear plasmid | 41% (29/71) | 49% (27/55) | ND |
| pALK172 | | | |
| fragment | 47% (48/103) | 30% (34/113) | 11% (8/72) |
| circular plasmid | 17% (4/23) | 13% (2/15) | 12% (12/104) |
| linear plasmid | 37% (22/59) | 24% (11/45) | ND |
| pALK173A | | | |
| circular plasmid | 75% (9/12) | 70% (14/20) | ND |
| linear plasmid | 67% (10/15) | 64% (14/22) | ND |
| pALK173B | | | |
| circular plasmid | 40% (4/10) | 63% (15/24) | ND |
| linear plasmid | 63% (10/16) | 67% (8/12) | ND |

Table 6. Plate assay positive transformants and total number of tested clones. The number of the plate assay positive transformants and the total number of phytase plate assay tested transformants are shown. Only those transformant strains that grew well both on the selection slant and on the plate assay are included. As positive phytase producers are counted those strains that clearly showed phytase activity on the plate assay.

The transformants that seemed to be the best producers on the plate assay were grown on shake flasks. Inocula were taken either directly from acetamide slants or from PD slants after purification through conidia. Of the *T. reesei* ATCCS6765, ALKO 233 and ALKO 2221, transformed with the fragments from pALK171 and pALK172, from 7 to 16 clones from each set of transformants were purified and the phytase production was tested in shake flask cultivations. When circular plasmids pALK171 or pALK172 had been used in transformations, 13 and 12 purified *T. reesei* ATCC56765, and from four to seven *T. reesei* ALKO 233 and ALKO 2221 transformant strains were grown, respectively. When linearized pALK171 or pALK172 plasmids were used, about 20 transformant strains from each were grown in shake flasks. Of the *T. reesei* ALKO 233 clones transformed with the linear pALK173A/B plasmids, seven PALK173A and two pALK173B (and with the circular plasmids four pALK173A and three pALK173B) transformants indicating phytase activity on plates were purified and tested in shake flask cultivations. For the *T. reesei* ALKO 2221 transformants the corresponding amounts tested in shake flask cultivations were as follows: for the linear plasmids, three pALK173A and five pALK173B and for the circular plasmids six pALK173A and six pALK173B transformants.

D. Phytase production by the Trichoderma transformants

The best phytase production levels from transformants of *T. reesei* ATCC56765, ALKO 233 and ALKO 2221, without *E. coli* sequences, when the cbh1 promoter (pALK171 and pALK172 fragments) was used are shown in Table 7.

TABLE 7

Phytase production and enzyme profiles of the best *T. reesei* phytase producing transformants with no *E. coli* sequences

| Strain | Fragment | Transformant | PNU/ml | CBHI | AGU/ml | HUT/ml | ECU/ml | FPU/ml |
|---|---|---|---|---|---|---|---|---|
| ALKO 233 | none | | < | (+) | 79 | 170 | 690 | 3.2 |
| | pALK171 | E16 | 3,590 | (−) | ND | ND | ND | ND |
| | | A53 | 2,820 | (+) | 91 | 140 | 385 | 2.1 |
| | | D1 | 2,740 | (+) | ND | ND | ND | ND |
| | | A52 | 2,580 | (+) | 88 | 190 | 505 | 3.0 |
| | | A13 | 2,570 | (+) | 82 | 215 | 905 | 1.1 |
| | pALK172 | E101 | 2,000 | (+) | ND | ND | ND | ND |
| | | A12 | 1,900 | (+) | 104 | ND | <1,000 | ND |
| | | D4 | 1,570 | (+) | ND | ND | ND | ND |
| | | E70 | 1,460 | (+) | ND | ND | ND | ND |
| | | E80 | 1,430 | (−) | ND | ND | ND | ND |
| ALKO 2221 | none | | < | (+) | <10 | <15 | 740 | 3.5 |
| | pALK171 | D2 | 3,200 | (+) | 32 | 42 | 460 | 2.4 |
| | | A9 | 2,840 | (+) | <10 | <20 | 480 | 2.6 |
| | | A24 | 2,760 | (+) | <10 | <20 | 340 | 1.5 |
| | | E3 | 2,670 | (−) | ND | ND | ND | ND |
| | | D1 | 2,390 | (+) | <10 | 32 | 410 | 2.5 |
| | pALK172 | B17 | 3,480 | (+) | ND | ND | ND | ND |
| | | E6 | 2,860 | (+) | ND | ND | ND | ND |
| | | D4 | 2,590 | (+) | 27 | 29 | 360 | 1.4 |
| | | E8 | 2,480 | (+) | ND | ND | ND | ND |
| | | A96 | 2,380 | (+) | <16 | 31 | 430 | 2.6 |
| ATCC56765 | none | | < | (+) | 1.1 | 57 | 200 | 0.8 |
| | pALK171 | B1 | 1,620 | (+) | <1.0 | 55 | 145 | <1.0 |
| | | A11 | 1,300 | (+) | <1.0 | 58 | 145 | <1.0 |
| | | A21 | 1,280 | (+) | <1.0 | ND | 120 | ND |
| | | B25 | 1,090 | (+) | <1.0 | ND | 60 | ND |

TABLE 7-continued

Phytase production and enzyme profiles of the best *T. reesei* phytase producing transformants with no *E. coli* sequences

| Strain | Fragment | Transformant | PNU/ml | CBHI | AGU/ml | HUT/ml | ECU/ml | FPU/ml |
|---|---|---|---|---|---|---|---|---|
|  | pALK172 | B19 | 1,780 | (+) | <1.0 | 52 | 120 | <1.0 |
|  |  | B1 | 1,180 | (+) | <1.0 | 53 | 120 | <1.0 |
|  |  | B11 | 1,080 | (+) | <1.0 | ND | 100 | ND |
| *A. niger* ALKO 243 | none |  | 1 | ND | 46 | 31 | 35 | 0.0 |

Phytase production and enzyme profiles of the best *T. reesei* phytase producing transformants with no *E. coli* sequences. Phytase activities as PNU/ml, background activities (AGU, HUT, ECU and FPU/ml) and the production of CBHI protein (+/−) in the supernatant are shown. *T. reesei* ATCC56765, ALKO 233 and ALKO 2221 strains were transformed with the XbaI fragment from the plasmid pALK171 or pALK172 (cbh1 promoter, no *E. coli* sequences). Strains were purified through conidia before cultivations. The values shown are averages from two shake flask cultivations. A "less than" sign (<) means that the value was below the detection level. ND = not determined.

About 3600 PNU/ml was obtained with the best transformant. About the same level of production could be achieved by using both the strains *T. reesei* ALKO 233 and ALKO 2221. The best phytase producing *T. reesei* ATCC56765 transformant produced about 1,800 PNU/ml. Both the phytase and the cbh1 signal sequence seemed to work equally well and the same levels in phytase production could be achieved when using *T. reesei* ALKO 2221 or ATCC56765 as a host strain. In *T. reesei* ALKO 233 the level of phytase activity produced was higher when the phytase signal sequence was used.

Some of the transformants did not produce any detectable CBHI protein which most probably indicates integration of the transforming DNA to the cbh1 locus. The absence of the CBHI protein did not affect the production levels in the screened transformants, i.e., good producers were found both among the transformants producing normal amounts of CBHI as well as among CBHI negative strains.

The best phytase production levels obtained by the use of pALK171 and pALK172 circular and linear plasmid are shown in the Table 8. The best production yields were obtained with the *T. reesei* ALKO 2221 that had been transformed with the linear plasmid pALK171 (phytase signal sequence).

TABLE 8

Phytase production by the *T. reesei* strains transformed with circular or linear plasmid pALK171 or pALK172

| Strain | Plasmid | Plasmid form | Transformant | PNU/ml |
|---|---|---|---|---|
| ALKO 233 | pALK171 | circular | C13 | 650 |
|  |  |  | C23 | 530 |
|  |  |  | C4 | 240 |
|  |  | linear | A22 | 1,610 |
|  |  |  | A21 | 1,270 |
|  |  |  | A17 | 1,180 |
|  | pALK172 | circular | C13 | 1,360 |
|  |  |  | C21 | 540 |
|  |  |  | C1 | 500 |
|  |  | linear | A20 | 1,420 |
|  |  |  | A27 | 1,330 |
|  |  |  | A32 | 980 |
| ALKO 2221 | pALK171 | circular | C2 | 1,630 |
|  |  |  | C8 | 1,290 |
|  |  |  | C32 | 810 |
|  |  | linear | A14 | 3,800 |
|  |  |  | A8 | 3,660 |
|  |  |  | B14 | 3,610 |
|  | pALK172 | circular | C3 | 480 |
|  |  |  | C4 | 190 |
| ATCC56765 | pALK171 | circular | C6 | 170 |
|  |  | linear | B18 | 2,060 |
|  |  |  | A36 | 1,790 |
|  |  |  | B9 | 1,390 |
|  |  | circular | A74 | 2,030 |
|  |  |  | A75 | 1,980 |
|  |  |  | B11 | 1,870 |
|  | pALK172 | circular | B3 | 2,250 |
|  |  |  | B23 | 1,970 |
|  |  |  | B1 | 1,030 |

Table 8. Phytase production by the *T. reesei* strains transformed with circular or linear plasmids pALK171 and pALK172. Phytase activities as PNU/ml in the culture supernatants of the three best phytase producing transformants of each type are shown. *T. reesei* ATCC56765 transformants were purified through conidia before cultivations and the results are averages from two shake flask cultivations. Inocula for cultivations of the *T. reesei* ALKO 233 and ALKO 2221 transformants were taken from the acetamide slants and the results shown are from one shake flask cultivation.

Also the *A. niger* phytase promoter can promote the expression of the gene in Trichoderma. However, the enzyme yields obtained are much lower than with the cbh1 promoter homologous to *T. reesei:* the activities obtained from the culture supernatants of transformants containing the phytase's own promoter were from about 1 to about 14 PNU/ml for the *T. reesei* ALKO 233 transformants and from about 6 to about 120 PNU/ml for the *T. reesei* ALKO 2221 transformants (Table 9).

TABLE 9

Phytase production by the *T. reesei* strains transformed with circular or linear plasmid pALK173A or pALK173B

| Strain | Plasmid | Plasmid form | Transformant | PNU/ml |
|---|---|---|---|---|
| ALKO 233 | pALK173A | circular | C25 | 14.2 |
|  |  |  | C29 | 6.6 |
|  |  |  | C23 | 1.2 |
|  |  | linear | D4 | 8.8 |
|  |  |  | D18 | 5.8 |
|  |  |  | D6 | 3.9 |
|  | pALK173B | circular | C8 | 3.5 |
|  |  |  | C6 | < |
|  |  |  | E10 | < |
|  |  | linear | D13 | 5.5 |
|  |  |  | D31 | < |

TABLE 9-continued

Phytase production by the *T. reesei* strains transformed with circular or linear plasmid pALK173A or pALK173B

| Strain | Plasmid | Plasmid form | Transformant | PNU/ml |
|---|---|---|---|---|
| ALKO 2221 | pALK173A | circular | E3 | 32.5 |
|  |  |  | E5 | 31.7 |
|  |  |  | C22 | 25.0 |
|  |  | linear | D24 | 37.5 |
|  |  |  | D36 | 8.3 |
|  |  |  | D17 | 5.8 |
|  | pALK173B | circular | C13 | 115.8 |
|  |  |  | C28 | 65.0 |
|  |  |  | C27 | 50.8 |
|  |  | linear | D9 | 36.7 |
|  |  |  | D26 | 22.5 |
|  |  |  | D21 | 18.3 |

Table 9. Phytase production by *T. reesei* transformants transformed with circular or linear plasmid pALK173A or pALK173B (phytase promoter). Phytase activities as PNU/ml in the culture supernatants of the transformants are shown. Transformants have been purified through conidia before cultivation. The results shown are from one shake flask cultivation. A "less than" sign (<) means that the value was below the detection level.

E. The enzyme background in the phytase preparations produced by *T. reesei*

Phytase is expressed in the *T. reesei* strains in high amounts and the background of other enzyme activities in the supernatants of *T. reesei* transformants is different from those in the Aspergillus supernatant (Table 7). Both endoglucanase and cellobiohydrolase activities are substantially higher when *T. reesei* is used as a production host compared to *A. niger*. The *T. reesei* strains used also produced proportionally less glucoamylase activity than the *A. niger* ALKO 243 strain.

F. Phytase protein produced by the Trichoderma transformants

Figure 10:
FIG. 10. Western blots of the samples from the culture supernatants of the Trichoderma host strains and transformants producing phytase. Lane 1: 50 ng of purified Aspergillus ALKO 243 phytase; Lane 2: 15 ng of endoF-treated Aspergillus ALKO 243 phytase; Lanes 3 and 10: *T. reesei* ALKO 233; Lanes 4–5 and 11–12: *T. reesei* ALKO 233 transformant 171FR/A4 and A13, respectively; Lanes 6 and 13: *T. reesei* ALKO 2221; Lanes 7–8 and 14–15: *T. reesei* ALKO 2221 transformant 171FR/A5 and A9, respectively; Lane 9: *T. reesei* ALKO 2221 transformant D2; Lane 16: *T. reesei* ATCC56765; Lanes 17, 18, 19: *T. reesei* ATCC56765 transformants 171FR/A21, A11, and A23, respectively. In each case 2 µl of 1:10 dilution of the culture supernatant were run in the gel. 171FR: the host transformed with the XbaI fragment from the plasmid pALK171.

Samples from the growth media of the transformants (pALK171 fragment) and the nontransformed *T. reesei* strains ATCC56765, ALKO 233 and ALKO 2221 were analyzed in Western blots (FIG. 10). Briefly, the following samples were analyzed: Lane 1: 50 ng of purified Aspergillus ALKO 243 phytase; Lane 2: 15 ng of endoF-treated Aspergillus ALKO 243 phytase; Lanes 3 and 10: *T. reesei* ALKO 233; Lanes 4–5 and 11–12: *T. reesei* ALKO 233 transformant 171FR/A4 and A13, respectively; Lanes 6 and 13: *T. reesei* ALKO 2221; Lanes 7–8 and 14–15: *T. reesei* ALKO 2221 transformant 171FR/A5 and A9, respectively; Lane 9: *T. reesei* ALKO 2221 transformant D2; Lane 16: *T. reesei* ATCC56765; Lanes 17, 18, 19: *T. reesei* ATCC56765 transformants 171FR/A21, A11, and A23, respectively. In each case, 2 μl of 1: 10 dilution of the culture supernatant were run on the gel. 171FR is the host transformed with the XbaI fragment from the plasmid pALK171.

The molecular weight of the phytase produced by Trichoderma differed from that produced by Aspergillus and the difference seemed to be due to differences in the glycosylation level. The phytase secreted by *T. reesei* ALKO 233 was visible in the Western blots as three and that secreted by *T. reesei* ALKO 2221 as 6 to 9 major protein bands of sizes of about 45–65 kDal, the lowest of which corresponded in size the deglycosylated Aspergillus phytase (45–48 kDal in SDS-PAGE). The phytase secreted by *T. reesei* ATCC56765 was of a size of 65–80 kDal and consisted of three to five protein bands. The molecular weight of the native Aspergillus phytase run in SDS-PAGE is about 80–85 kDal. The phytase protein produced by the transformants that had been transformed with pALK172 fragment or pALK173A/B showed the same kind of banding pattern.

III. Conclusions

The production level of Aspergillus phytase obtained when *T. reesei* was used as a production host was surprisingly high. By using *T. reesei*, the phytase is produced in a novel background differing from that of Aspergillus and containing enzymes important e.g. in feed applications. The molecular weight of the Aspergillus phytase protein produced in Trichoderma is different from that of Aspergillus. This difference in size seemed to be due to different glycosylation but did not affect the enzyme activity.

EXAMPLE 7

Production of *Aspergillus niger* pH 2.5 Acid Phosphatase in *Trichoderma reesei*

I. EXPERIMENTAL PROTOCOLS

1. Strains and plasmids

Figure 12:
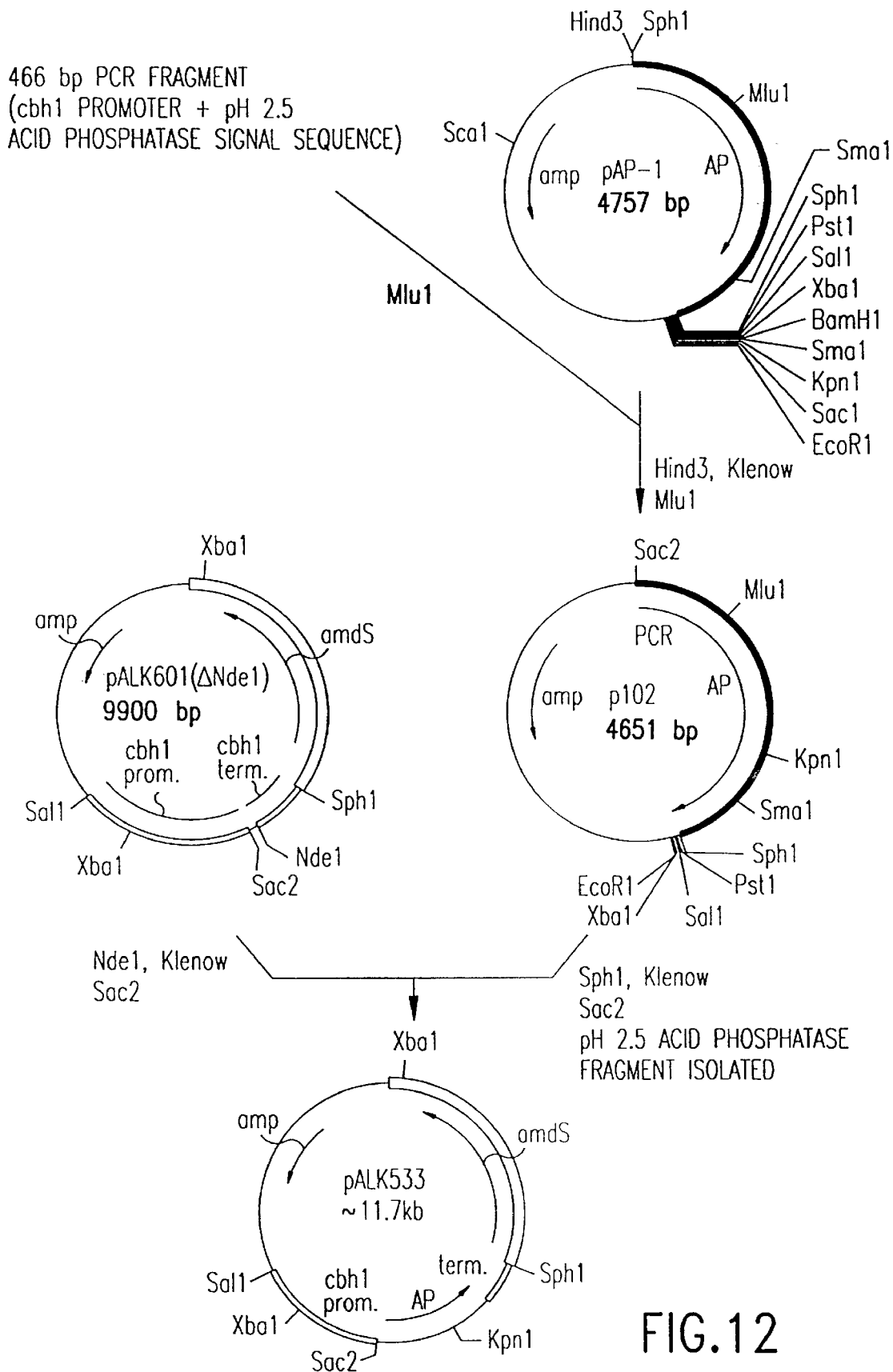
FIG. 12. Construction of the plasmid pALK533. The pH 2.5 acid phosphatase gene with its own signal sequence was fused to the cbh1 promoter.
Figure 13:
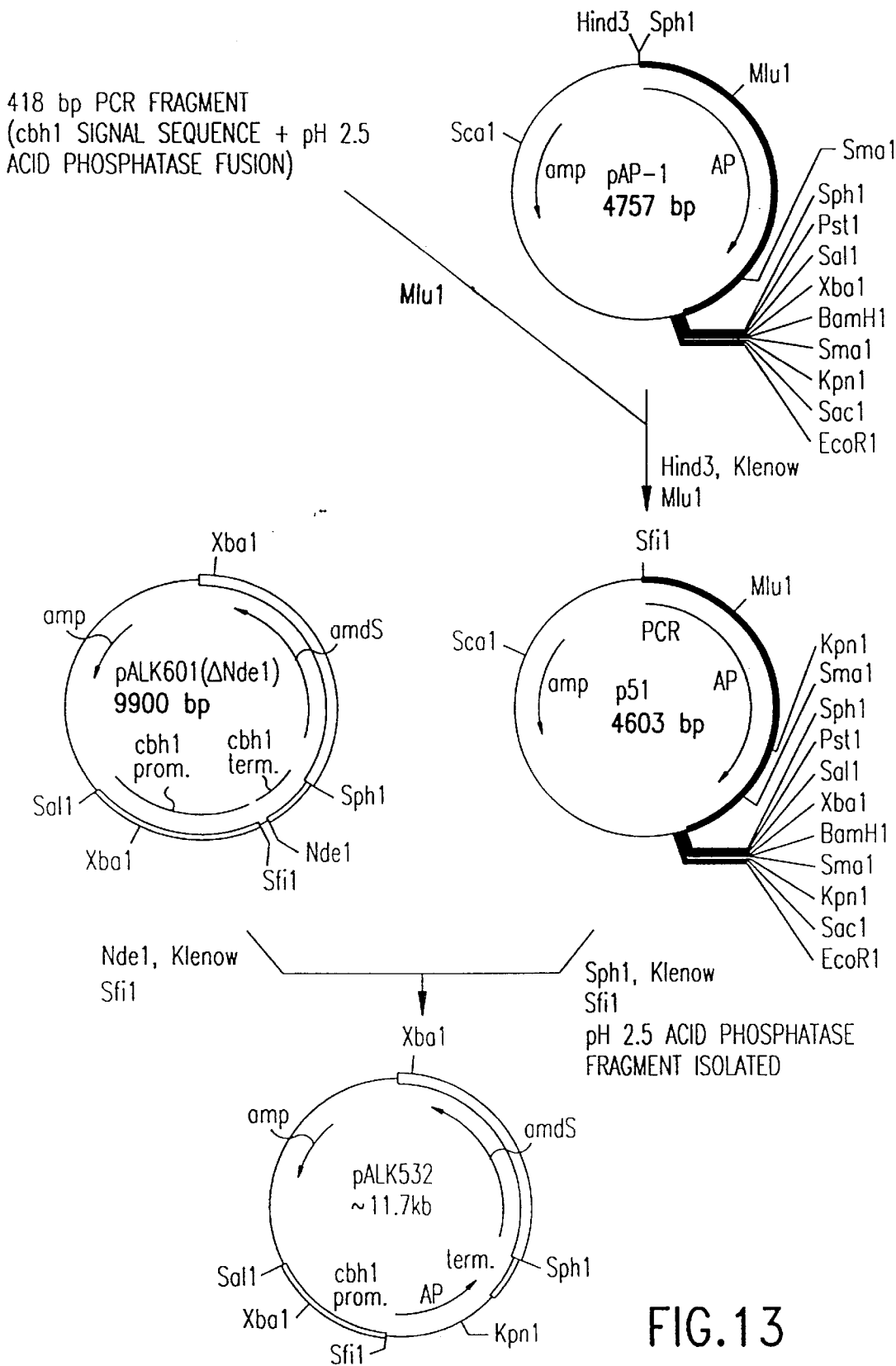
FIG. 13. Construction of the plasmid pALK532. The pH 2.5 acid phosphatase gene was fused to the cbhI signal sequence and promoter.

*E. coli* strains XL1 -Blue (Bullock, W. O. et al., *Biotechniques* 5: 376–379 (1987); Stratagene, La Jolla, Calif., USA) and Sure™ (Greener, A., Strategies 3: 5–6 (1990); Stratagene, La Jolla, Calif., USA) were used as hosts for constructions made of plasmids pALK601 (FIGS. 12 and 13) and pAP-1 (FIGS. 12 and 13). The plasmid pALK601 contains the *T. reesei* cbh1 promoter, and terminator sequences and the *Aspergillus nidulans* acetamidase gene. The plasmid pAP-1 contains pH 2.5 acid phosphatase gene from *Aspergillus niger* var. *awamori* ALKO 243 (ATCC 38854).

*Trichoderma reesei* strain ALKO 2221, a low aspartyl protease mutant derived from the *T. reesei* strain ALKO 233 (VTT-D-79125) by UV-mutagenesis was used as a recipient for the pH 2.5 acid phosphatase gene.

2. Growth media and culture conditions

*E. coli* strains were grown in L-broth (Maniatis, T., et al., *Molecular Cloning, A Laboratory Manual*, Cold Spring Harbor Laboratory, Cold Spring Harbor, N.Y., USA (1982)) supplemented with ampicillin (50 μg/ml) when needed. *E. coli* cultivations were carried out at 37° C. overnight.

PD agar slants (Potato Dextrose broth by Difco, Detroit, Mich., USA) were used for storing the Trichoderma strains. The plates and media for *T. reesei* transformations were essentially as in Penttilä et al. (Penttilä, M., et al., *Gene* 61: 155–164 (1987)). The transformants were purified on selective acetamide-CsCl medium (Penttilä, M. et al., *Gene* 61: 155–164 (1987) before transferring to PD slants. *T. reesei* transformants were grown in lactose based medium (see Example 6, subparagraph 2) at 30° C. (250 rpm) for 7 days for expression of pH 2.5 acid phosphatase under the control of the cbh1 promoter.

3. Manipulation of DNA

Manipulations of DNA were performed as described above for phytase, mainly by standard methods (Maniatis, T., et al., *Molecular Cloning, A Laboratory Manual*, Cold Spring Harbor Laboratory, Cold Spring Harbor, N.Y., USA (1982)). Plasmid DNA from *E. coli* was isolated by using Qiagen columns (Diagen GmbH, Dusseldorf, FRG) according to the supplier's instructions. For rapid screening of the plasmid DNA from *E. coli*, the method of Holmes and Quigley, (Holmes and Quigley, *Anal. Biochem.* 114: 193–197 (1981)) was used. The restriction enzymes, T4 DNA ligase, Klenow fragment of DNA polymerase I and T4 DNA polymerase used in the DNA manipulations were from Boehringer (Mannheim, FRG) and New England Biolabs (Beverly, Mass., USA). Each enzyme was used according to the supplier's recommendation. DNA fragments for cloning or transformations were isolated from low melting point agarose gels (FMC Bioproducts, Rockland, Me., USA) by the freeze thaw phenol method (Benson, S. A. *Bio/ Techniques* 2: 66–68 (1984)) or by using the Mermaid™ Kit (BIO 101 Inc., La Jolla, Calif., USA) according to the supplier's instructions.

Sequencing of the fusions between the cbh1 promoter and pH 2.5 acid phosphatase gene was carried out by means of pUC/M13 primers and extension primers using Taq DyeDeoxy™ Terminator Cycle Sequencing Kit (Applied Biosystems) and the automated sequencer (Applied Biosystems 373A, Foster City, Calif., USA).

The oligonucleotides used were synthesized by an Applied Biosystems (Foster City, Calif., USA) 381A Synthesizer except the M13 primers that were purchased from the Applied Biosystems.

4. Transformations

Transformations were also performed as described above for phytase. Transformation of *E. coli* strains XL1-Blue or Sure was performed by the supplier's method (Stratagene La Jolla, Calif., USA), *T. reesei* strains were transformed essentially according to the method of Penttilä et al. (Penttilä, M., et al., *Gene* 61: 155–164 (1987)). Novozym 234 used in fungal protoplast preparation for transformations was from Novo Industri AS (Copenhagen, Denmark). Prior sporulating on PD slants *T. reesei* transformants were purified through conidia on the selective acetamide medium.

5. Enzyme activity assays

For the enzyme assays the mycelium was separated from the culture medium by centrifuging for 15 min at 3,000 rpm (Sorvall SS-34, Dupont Company, Wilmington, Del., USA). The pH 2.5 acid phosphatase enzyme activity was measured from the culture supernatant using paranitrophenylphosphate (Sigma, St. Louis, USA) as a substrate as described earlier. One pH 2.5 acid phosphatase activity unit releases 1 nmol of inorganic phosphate per minute on the substrate p-nitrophenylphosphate in pH 2.5 at 37° C. One acid phosphatase normalized unit (APNU) is defined as the amount of acid phosphatase activity produced by the *A. niger* ALKO 243 strain under the cultivation conditions used (see Example 6, subparagraph 2).

Amyloglucosidase activity (AGU) was measured by using 1% Zulkowsky starch (Merck) as a substrate and measuring the amount of the released glucose units by boiling with DNS reagent (see below) after 10 min of reaction at 60° C. at pH 4.8. Proteases (HUT) were measured at pH 4.7 as in Food Chemicals Codex (*Food Chemicals Codex*, National Academy Press, Washington, D.C., USA, pp. 496–497 (1981)) by using 2% haemoglobin (Sigma) as a substrate. Endoglucanase (ECU) and cellobiohydrolase (FPU) activities were measured as in IUPAC's Measurement of cellulase activities (IUPAC Commission on Biotechnology, *Measurement of Cellulase Activities*, Biochemical Engineering Research Centre, Indian Institute of Technology, Delhi, India, pp. 5–7 and 10–11 (1981)). 1% hydroxyethylcellulose (Fluka AG) in 50 mM Na-citrate buffer (pH 4) and Whatman no. 1 paper were used as substrates, respectively. DNS used differed from that described at the IUPAC's Measurement of cellulase activities (IUPAC Commission on Biotechnology, *Measurement of Cellulase Activities*, Biochemical Engineering Research Centre, Indian Institute of Technology, Delhi, India, pp. 5–7 and 10–11 (1984)) and was made by first diluting 50.0 g 2-hydroxy-3,5-dinitrobentsoicacid (Merck) into 4 liters of deionized water. Then 80.0 g NaOH was added slowly by using the magnetic stirrer and 1,500 g K-Na-tartrate (Merck) was added and diluted by heating the solution (maximum temperature 45° C.). The total volume was adjusted to 5 liters, the solution was filtered through Whatman no. 1 and was protected from light.

6. SDS-page and Western blot analysis

Sodium dodecyl sulphate polyacrylamide gel electrophoresis (SDS-page) and Western blot analysis were done according to the methods of Laemmli (Laemmli, U.K., *Nature* 227: 680–685 (1970)) and Towbin et al. (Towbin, H., et al., *Proc. Natl. Acad. Sci. USA* 76: 4350–4354 (1979)). Visualization of the pH 2.5 acid phosphatase protein in Western blots was done by using the polyclonal rabbit antiserum KH1269. KH1269 was made against purified deglycosylated pH 2.5 acid phosphatase protein (M. Turunen, Alko Ltd.) and it was supplied by the National Public Health Institute (Helsinki, Finland). Visualization of the CBHI protein from the pH 2.5 acid phosphatase transformants in Western blots was done by using the mouse monoclonal antibody CI-261 (Aho, S. et al., *Eur. J. Biochem* 200: 643–649 (1991)). Anti-rabbit-IgG and anti-mouse-IgG alkaline phosphate conjugate and color development substrates from ProtoBlot™ Immunoblotting system (Promega, Madison, USA) were used to detect the immunocomplexes.

7. PCR

The PCR reactions were performed by a Techne thermal cycler PHC-2 (Techne Ltd., Cambridge, UK) in 100 μl volumes. The reaction mixture contained 0.2 mM of each dNTP (Pharmacia pH 8.3), 20–50 pmol of each primer and 10 ng of plasmid template in 10 mM Tris buffer (pH 8.3), 50 mM KCl, 1.5 mM $MgCl_2$ and 100 μg/ml gelatin. The protocol used was the following: 96° C./10 min before adding the Taq DNA polymerase (2 units, Boehringer Mannheim, FRG) and 100 μl of paraffin oil, denaturation 95° C./1 min, annealing 60° C./1 min, extension 72° C./1 min for 30 cycles. The final extension time was 9 min to ensure completion of the strand synthesis. The PCR fragments were purified by Mermaid™ Kit. The ends of the fragments were filled by using the DNA polymerase I Klenow fragment.

II. RESULTS

A. Vector constructions for overexpression of the pH 2.5 acid phosphatase gene in *Trichoderma reesei* ALKO 2221

1. Construction of plasmid pALK533

The plasmid pALK533 consists of *Aspergillus niger* var. *awamori* ALKO 243 pH2.5 acid phosphatase gene with its own signal sequence inserted into the *Trichoderma reesei* expression casette containing the cbh1 promoter and terminator sequences. pALK533 also contains the *Aspergillus nidulans* amdS gene as a selection marker for transformants.

The precise fusion between the cbh1 promoter and the pH 2.5 acid phosphatase signal sequence was done with PCR. The primers used for the PCR fragments are shown in FIG. 11. The SacII site in the cbh1 promoter area was used in the 5'-primer and the MluI site of the acid phosphatase gene (374 nucleotides down from the N-terminal of the acid phosphatase gene) was used in the 3'-primer. The 5'-primer was a 39-mer containing a tail of 19 nucleotides of the cbh1 promoter sequence preceding the signal sequence joining exactly to the first 20 nucleotides of the acid phosphatase signal sequence. The 3'-primer was a 30-mer of pH 2.5 acid phosphatase gene. pAP-1 (FIG. 12) was used as a template in the PCR reactions. A fragment of the expected length of 466 bps was obtained from the PCR reaction.

The 466 bp PCR fragment containing the pH 2.5 acid phosphatase signal sequence was digested with MluI and ligated to pAP-1 that had been digested with HindIII, treated with DNA polymerase I Klenow fragment and digested with MluI to obtain plasmid p102 (FIG. 12). The fusion and the PCR fragment were sequenced to ensure that no mistakes had occurred in the PCR amplification.

To construct plasmid pALK533 (FIG. 12), a pH 2.5 acid phosphatase gene containing the fusion was isolated from the plasmid p102 as an SphI (filled in with DNA polymerase I Klenow fragment)-SacII fragment and inserted between the cbh1 promoter and terminator of the plasmid pALK601 (ΔNdeI) that had been digested with NdeI (filled in with DNA polymerase I Klenow fragment) and SacII. In pALK601 (ΔNdeI), the NdeI site in the intron area of the amdS gene in pALK601 is inactivated using DNA polymerase I Klenow fragment. The linear fragment used for transformations was digested out from the vector backbone with XbaI.

2. Construction of the plasmid pALK532

The plasmid pALK532 consists of the *Aspergillus niger* var. *awamori* ALKO 243 pH 2.5 acid phosphatase gene inserted into the *Trichoderma reesei* CBHI expression casette containing the cbh1 promoter and signal sequence and terminator sequences. pALK532 also contains the *Aspergillus nidulans* amdS gene as a selection marker for transformants.

B. Transformation of *Trichoderma reesei* and screening of the transformants

*Trichoderma reesei* ALKO 2221 was transformed separately with the linear XbaI fragments from the plasmid pALK532 and pALK533. Transformation frequencies (transformants/μg of DNA) varied from 2 to 30.

Forty-four *T. reesei* ALKO 2221/pALK532 transformants and 103 pALK533 transformants were purified through conidia and were cultivated in shake flasks.

C. pH 2.5 acid phosphatase production by the *Trichoderma* transformants

The best transformants based on the pH 2.5 acid phosphatase production are shown in the Table 10. The best enzyme activity level was 240 APNU/ml in shake flask cultivation in lactose based medium.

TABLE 10

| Strain | Plasmid | APNU/ml | CBHI(+/−) | AGU/ml | HUT/ml | ECU/ml | FPU/ml |
|---|---|---|---|---|---|---|---|
| untransformed ALKO 2221 | none | 0.2 | (+) | 48 | 18 | 600 | 3.8 |
| transformed |  |  |  |  |  |  |  |
| SC-9 | pALK532 | 240 | (+) | 53 | 32 | 380 | 2.4 |
| KA-31 | pALK533 | 240 | (+) | 37 | 19 | 490 | 2.0 |
| KA-17 | pALK533 | 230 | (−) | 44 | 52 | 760 | 1.1 |
| KB-44 | pALK533 | 230 | (+) | 37 | 16 | 490 | ND |
| KB-18 | pALK533 | 220 | ND | ND | ND | ND | ND |
| SB-4 | pALK532 | 210 | (+) | 35 | 14 | 590 | ND |
| KA-28 | pALK533 | 190 | (+) | ND | ND | ND | ND |
| KB-38 | pALK533 | 190 | (+) | ND | ND | ND | ND |
| SC-6 | pALK532 | 190 | (+) | 40 | 21 | 520 | ND |
| SC-32 | pALK532 | 190 | (−) | ND | ND | ND | ND |
| A. niger ALKO 243 | none | 1 | ND | 46 | 31 | 35 | 0.0 |

The best pH 2.5 acid phosphatase producing *T. reesei* ALKO 2221 transformants. pH 2.5 acid phosphatase enzyme activity levels as APNU/ml produced in the 50 ml shake flask cultivations, background activities (AGU, ECU, FPU and HUT/ml) and the production of CBHI protein (+/−, Western blot) are shown.

The precise fusion between the cbh1 signal sequence and the pH 2.5 acid phosphatase gene was done with PCR. The primers used for PCR fragments are shown in FIG. 11. The SfiI site in the cbh1 signal sequence was used in the 5'-primer. The 5'-primer was a 46-mer containing a tail of 28 nucleotides joining exactly to the first 18 nucleotides of the acid phosphatase N-terminal sequence. The 3'-primer was the same 30-mer used in the construction of pALK533. pAP-1 was used as a template in the PCR reaction. A fragment of the expected length of 418 bps was obtained from the PCR reaction.

The 418 bp PCR fragment containing the cbh1 signal sequence was digested with MluI and ligated to pAP-1 that had been digested with HindIII, treated with DNA polymerase I Klenow fragment and digested with MluI to obtain plasmid p51 (FIG. 13). The fusion and the PCR fragment were sequenced to ensure that no mistakes had occurred in the PCR amplification. To construct the plasmid pALK532 (FIG. 13), a pH 2.5 acid phosphatase fragment containing the fusion was isolated from the plasmid p51 as a SphI (filled in with DNA polymerase I Klenow fragment)-SfiI fragment and was inserted between the cbh1 promoter and terminator areas of the plasmid pALK601 (ΔNdeI). pALK601 (ΔNdeI) had been digested with NdeI and filled in with the DNA polymerase I Klenow fragment and digested with SfiI. The approximately 7.8 kb linear fragment that contained no bacterial sequences was isolated from pALK532 by restricting with XbaI and was used for transformations.

Both the acid phosphatase and the cbh1 signal sequence worked equally well and about the same level of pH 2.5 acid phosphatase activity could be achieved. The best pH 2.5 acid phosphatase activity level was produced by Trichoderma transformant SC-9 and was about 250 fold greater than the levels produced by native *Aspergillus niger* var. *awamori* ALKO 243 strain in corresponding conditions.

Two out of the nine best producers did not react with the monoclonal CBHI antibody in Western blot analysis suggesting that the expression casette had integrated to the cbh1 locus in those two transformants (Table 10).

D. The enzyme background in the pH 2.5 acid phosphatase preparations produced by *T. reesei*

The pH 2.5 acid phosphatase is expressed in the *T. reesei* transformants in high amounts and the background of some other enzyme activities in the supernatants of *T. reesei* transformants is different from those in the Aspergillus supernatant (Table 10). Both endoglucanase and cellobiohydrolase activities are significantly higher when *T. reesei* is used as a production host. The *T. reesei* transformants also produced proportionally less glucoamylase activity than the *A. niger* ALKO 243 strain.

Figure 14:
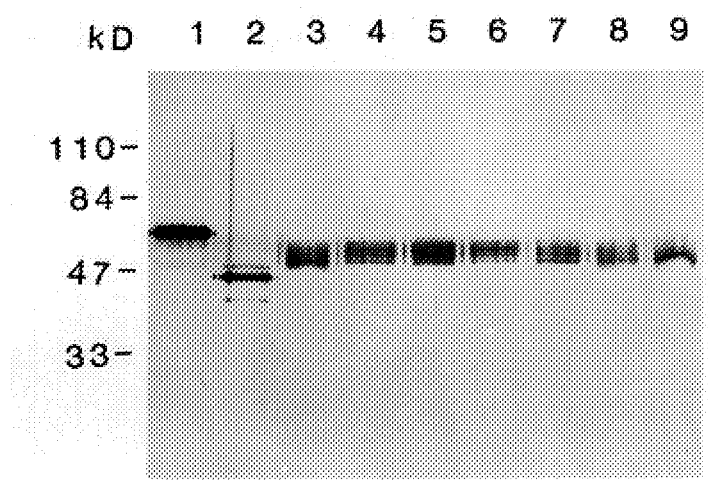
FIG. 14. Western blot of the Trichoderma transformants producing pH 2.5 acid phosphatase. Lane 1: 10 ng of purified Aspergillus ALKO 243 pH 2.5 acid phosphatase; Lane 2: 10 ng of endoF treated Aspergillus ALKO 243 pH 2.5 acid phosphatase; and Lanes 3–9: 60ng of protein from the each of the culture supernatants of *Trichoderma reesei* ALKO 2221 transformants SC-9, KA-31, KA-17, KB-44, KB-18, SB-4 and KA-28, respectively.

E. Identification of the pH 2.5 acid phosphatase produced by the Trichoderma transformants Samples from the growth media of the transformants and the *T. reesei* ALKO 2221 strain were analyzed in Western blot (FIG. 14). The following samples were analyzed: 10 ng of purified Aspergillus ALKO 243 pH 2.5 acid phosphatase; 10 ng of endoF treated Aspergillus ALKO 243 pH 2.5 acid phosphatase; and 60 ng of protein from the each of the culture supernatants of *Trichoderma reesei* ALKO 2221 transformants SC-9, KA-31, KA-17, KB-44, KB-18, SB-4 and KA-28 (FIG. 14).

The pH 2.5 acid phosphatase secreted by *T. reesei* transformants was seen as four protein bands of sizes of about 50–66 kD. This is probably due to the different level of glycolysation of the protein part of the secreted pH 2.5 acid phosphatase. Compared to the size of the pH 2.5 acid phosphatase produced by *Aspergillus niger* var. *awamori* ALKO 243 strain (66 kD) a majority of the pH 2.5 acid phosphatase proteins produced by *T. reesei* are smaller than that produced by Aspergillus.

All references are incorporated herein by reference. Having now fully described the invention, it will be understood by those with skill in the art that the scope may be performed with a wide and equivalent range of concentrations, parameters, and the like, without affecting the spirit or scope of the invention or any embodiment thereof.

What is claimed is:

1. A purified nucleic acid molecule comprising a first genetic sequence encoding a phytase having the amino acid sequence of amino acids 1–467 of SEQ ID NO: 8, or a catalytically active fragment thereof.

2. The purified nucleic acid molecule of claim 1, wherein said amino acid sequence of amino acids 1–467 of SEQ ID NO: 8 is encoded by the coding sequence of bases 404–1906 of SEQ ID NO: 7.

3. The purified nucleic acid molecule of claim 1, said catalytically active fragment of said phytase having the amino acid sequence of amino acids 20–467 of SEQ ID NO: 8.

4. The purified nucleic acid molecule of claim 3, wherein said amino acid sequence of amino acids 20–467 is encoded by bases 563–1906 of SEQ ID NO: 7.

5. The purified nucleic acid molecule of claim 3, further comprising a second genetic sequence encoding a signal sequence, said second genetic sequence being operably linked to said first genetic sequence.

6. The purified nucleic acid molecule of claim 5, wherein said second genetic sequence encodes the phytase signal sequence having the amino acid sequence of amino acids 1–19 of SEQ ID NO: 8.

7. The purified nucleic acid molecule of claim 6, wherein the amino acid sequence of amino acids 1–19 of SEQ ID NO: 8 is encoded by the coding sequence of bases 404–562 of SEQ ID NO: 7.

8. A vector comprising a first genetic sequence encoding a phytase having the amino acid sequence of amino acids 1–467 of SEQ ID NO: 8, or a catalytically active fragment thereof.

9. The vector of claim 8, wherein said amino acid sequence of amino acids 1–467 of SEQ ID NO: 8 is encoded by the coding sequence of bases 404–1906 of SEQ ID NO: 7.

10. The vector of claim 8, said catalytically active fragment of said phytase having the amino acid sequence of amino acids 20–467 of SEQ ID NO: 8.

11. The vector of claim 10, wherein said amino acid sequence of amino acids 20–467 is encoded by bases 563–1906 of SEQ ID NO: 7.

12. The vector of claim 10, further comprising a second genetic sequence encoding a signal sequence, said second genetic sequence being operably linked to said first genetic sequence.

13. The vector of claim 12, wherein said second genetic sequence encodes the phytase signal sequence having the amino acid sequence of amino acids 1–19 of SEQ ID NO: 8.

14. The vector of claim 13, wherein the amino acid sequence of amino acids 1–19 of SEQ ID NO: 8 is encoded by the coding sequence of bases 404–562 of SEQ ID NO: 7.

15. The vector of claim 8, wherein said vector is selected from the group consisting of pALK171, pALK172, pALK173A and pALK173B, and a fragment thereof that encodes said phytase or said catalytically active fragment thereof.

16. A purified nucleic acid molecule comprising a first genetic sequence encoding a pH 2.5 acid phosphatase having the amino acid sequence of amino acids 1–479 of SEQ ID NO: 2, or a catalytically active fragment thereof.

17. The purified nucleic acid molecule of claim 16, wherein said amino acid sequence of amino acids 1–479 of SEQ ID NO: 2 is encoded by bases 136–1737 of SEQ ID NO: 1.

18. The purified nucleic acid molecule of claim 16, said catalytically active fragment of said pH 2.5 acid phosphatase having the amino acid sequence of amino acids 20–479 of SEQ ID NO: 2.

19. The purified nucleic acid molecule of claim 18, wherein said amino acid sequence of amino acids 20–479 is encoded by bases 193–1737 of SEQ ID NO: 1.

20. The purified nucleic acid molecule of claim 18, further comprising a second genetic sequence encoding a signal sequence, said second genetic sequence being operably linked to said first genetic sequence.

21. The purified nucleic acid molecule of claim 20, wherein said second genetic sequence encodes the pH 2.5 acid phosphatase signal sequence having the amino acid sequence of amino acids 1–19 of SEQ ID NO: 2.

22. The purified nucleic acid molecule of claim 21, wherein the amino acid sequence of amino acids 1–19 of SEQ ID NO: 2 is encoded by the coding sequence of bases 136–192 of SEQ ID NO: 1.

23. A vector comprising a first genetic sequence encoding a pH 2.5 acid phosphatase having the amino acid sequence of amino acids 1–479 of SEQ ID NO: 2, or a catalytically active fragment thereof.

24. The vector of claim 23, wherein said amino acid sequence of amino acids 1–479 of SEQ ID NO: 2 is encoded by bases 136–1737 of SEQ ID NO: 1.

25. The vector of claim 23, said catalytically active fragment of said pH 2.5 acid phosphatase having the amino acid sequence of amino acids 20–479 of SEQ ID NO: 2.

26. The vector of claim 25, wherein said amino acid sequence of amino acids 20–479 is encoded by bases 193–1737 of SEQ ID NO: 1.

27. The vector of claim 25, further comprising a second genetic sequence encoding a signal sequence, said second genetic sequence being operably linked to said first genetic sequence.

28. The vector of claim 27, wherein said second genetic sequence encodes the phytase signal sequence having the amino acid sequence of amino acids 1–19 of SEQ ID NO: 2.

29. The vector of claim 28, wherein the amino acid sequence of amino acids 1–19 of SEQ ID NO: 2 is encoded by the coding sequence of bases 136–192 of SEQ ID NO: 1.

30. The vector of claim 26, wherein said vector is selected from the group consisting of pALK532, pALK533, and a fragment thereof that encodes said pH 2.5 acid phosphatase or said catalytically active fragment thereof.

31. A host cell into which has been introduced a nucleic acid molecule comprising a genetic sequence encoding a phytate degrading enzyme selected from the group consisting of a phytase having the amino acid sequence of amino acids 1–467 of SEQ ID NO: 8, a catalytically active fragment of said phytase, a pH 2.5 acid phosphatase having the amino acid sequence of amino acids 1–479 of SEQ ID NO: 2, and a catalytically active fragment of said pH 2.5 acid phosphatase.

32. The host cell of claim 31, wherein said genetic sequence has been introduced by transfection.

33. The host cell of claim 31, wherein said genetic sequence is introduced by transformation.

34. The host cell of claim 31, wherein said genetic sequence encodes a phytase having the amino acid sequence of amino acids 1–467 of SEQ ID NO: 8, or a catalytically active fragment thereof.

35. The host cell of claim 34, wherein said amino acid sequence of amino acids 1–467 of SEQ ID NO: 8 is encoded by the coding sequence of bases 404–1906 of SEQ ID NO: 7.

36. The host cell of claim 34, said catalytically active fragment of said phytase having the amino acid sequence of amino acids 20–467 of SEQ ID NO: 8.

37. The host cell of claim 36, wherein said amino acid sequence of amino acids 20–467 is encoded by bases 563–1906 of SEQ ID NO: 7.

38. The host cell of claim 36, further comprising a second genetic sequence encoding a signal sequence, said second genetic sequence being operably linked to said first genetic sequence.

39. The host cell of claim 38, wherein said second genetic sequence encodes the phytase signal sequence having the amino acid sequence of amino acids 1–19 of SEQ ID NO: 8.

40. The host cell of claim 39, wherein the amino acid sequence of amino acids 1–19 of SEQ ID NO: 8 is encoded by the coding sequence of bases 404–562 of SEQ ID NO: 7.

41. The host cell of claim 31, wherein said genetic sequence encodes a pH 2.5 acid phosphatase having the amino acid sequence of amino acids 1–479 of SEQ ID NO: 2, or a catalytically active fragment thereof.

42. The host cell of claim 41, wherein said amino acid sequence of amino acids 1–479 of SEQ ID NO: 2 is encoded by bases 136–1737 of SEQ ID NO: 1.

43. The host cell of claim 41, said catalytically active fragment of said pH 2.5 acid phosphatase having the amino acid sequence of amino acids 20–479 of SEQ ID NO: 2.

44. The host cell of claim 43, wherein said amino acid sequence of amino acids 20–479 is encoded by bases 193–1737 of SEQ ID NO: 1.

45. The host cell of claim 41, further comprising a second genetic sequence encoding a signal sequence, said second genetic sequence being operably linked to said first genetic sequence.

46. The host cell of claim 45 wherein said second genetic sequence encodes the pH 2.5 acid phosphatase signal sequence having the amino acid sequence of amino acids 1–19 of SEQ ID NO: 2.

47. The host cell of claim 46 wherein the amino acid sequence of amino acids 1–19 of SEQ ID NO: 2 is encoded by the coding sequence of bases 136–192 of SEQ ID NO: 1.

48. The host cell of claim 31, wherein said host cell is a prokaryotic cell.

49. The host cell of claim 31, wherein said host cell is a eukaryotic cell.

50. The host cell of claim 49, wherein said eukaryotic cell is selected from the group consisting of an animal cell, a plant cell, a fungal cell, and a yeast cell.

51. The host cell of claim 50, wherein eukaryotic cell is a fungal cell.

52. The host cell of claim 51, wherein said fungal cell is Trichoderma.

53. The host cell of claim 52, wherein said genetic sequence is integrated into the genome of said Trichoderma.

54. The host cell of claim 53, wherein said genetic sequence is integrated into the cbh1 locus of said Trichoderma.

55. The host cell of claim 52, wherein said host cell is *Trichoderma reesei.*

56. The host cell of claim 52, wherein said first genetic sequence encoding said phytate degrading enzyme is operably linked to a second genetic sequence encoding a signal sequence.

57. The host cell of claim 56, wherein said signal sequence is selected from the group consisting of the signal sequence of Trichoderma CBHI, the signal sequence of Trichoderma CBHII, the signal sequence of Trichoderma EGI, the signal sequence of Trichoderma EGII, amino acids 1–19 of SEQ ID NO: 8, and amino acids 1–19 of SEQ ID NO: 2.

58. A method for overexpressing phytate degrading enzymes in a host cell, wherein the method comprises the steps of:
  (a) preparing a DNA construct, said DNA construct comprising a first genetic sequence selected from the group consisting of a phytase having the amino acid sequence of amino acids 1–467 of SEQ ID NO: 8, a catalytically active fragment of said phytase, a pH 2.5 acid phosphatase having the amino acid sequence of amino acids 1–479 of SEQ ID NO: 2, and a catalytically active fragment of said pH 2.5 acid phosphatase;
  (b) transforming a host cell with said DNA construct; and
  (c) cultivating the transformed host cell under conditions suitable for growth of said host cell and for expression of said phytate degrading enzyme.

59. The method of claim 58, wherein said first genetic sequence encodes a phytase having the amino acid sequence of amino acids 1–467 of SEQ ID NO: 8, or a catalytically active fragment thereof.

60. The method of claim 59, wherein said amino acid sequence of amino acids 1–467 of SEQ ID NO: 8 is encoded by the coding sequence of bases 404–1906 of SEQ ID NO: 7.

61. The method of claim 59, said catalytically active fragment of said phytase having the amino acid sequence of amino acids 20–467 of SEQ ID NO: 8.

62. The method of claim 61, wherein said amino acid sequence of amino acids 20–467 is encoded by bases 563–1906 of SEQ ID NO: 7.

63. The method of claim 61, further comprising a second genetic sequence encoding a signal sequence, said second genetic sequence being operably linked to said first genetic sequence.

64. The method of claim 63, wherein said second genetic sequence encodes the phytase signal sequence having the amino acid sequence of amino acids 1–19 of SEQ ID NO: 8.

65. The method of claim 64, wherein the amino acid sequence of amino acids 1–19 of SEQ ID NO: 8 is encoded by the coding sequence of bases 404–562 of SEQ ID NO: 7.

66. The method of claim 58, wherein said first genetic sequence encodes a pH 2.5 acid phosphatase having the amino acid sequence of amino acids 1–479 of SEQ ID NO: 2, or a catalytically active fragment thereof.

67. The method of claim 66, wherein said amino acid sequence of amino acids 1–479 of SEQ ID NO: 2 is encoded by bases 136–1737 of SEQ ID NO: 1.

68. The method of claim 66, said catalytically active fragment of said pH 2.5 acid phosphatase hang the amino acid sequence of amino acids 20–479 of SEQ ID NO: 2.

69. The method of claim 68, wherein said amino acid sequence of amino acids 20–479 is encoded by bases 193–1737 of SEQ ID NO: 1.

70. The method of claim 66, said DNA construct further comprising a second genetic sequence, said second genetic sequence being operably linked to said first genetic sequence.

71. The method of claim 70, wherein said second genetic sequence encodes the pH 2.5 acid phosphatase signal sequence having the amino acid sequence of amino acids 1–19 of SEQ ID NO: 2.

72. The method of claim 71, wherein the amino acid sequence of amino acids 1–19 of SEQ ID NO: 2 is encoded by the coding sequence of bases 136–192 of SEQ ID NO: 1.

73. The method of claim 58, wherein sad host cell is a prokaryotic cell.

74. The method of claim 58, wherein said host cell is a eukaryotic cell.

75. The method of claim 74, wherein said eukaryotic cell is selected from the group consisting of an animal cell, a plant cell, a fungal cell, and a yeast cell.

76. The method of claim 75, wherein eukaryotic cell is a fungal cell.

77. The method of claim 76, wherein said fungal cell is Trichoderma.

78. The method of claim 77, wherein said DNA construct is provided to said Trichoderma in a linear form.

79. The method of claim 78, wherein said linear form lacks bacterial sequences.

80. The method of claim 77, wherein said DNA construct is provided to said Trichoderma in a circular plasmid form.

81. The method of claim 77, wherein said host cell is *Trichoderma reesei*.

82. The method of claim 77, wherein said first genetic sequence encoding said phytate degrading enzyme is operably linked to a second genetic sequence encoding a signal sequence.

83. The method of claim 82, wherein said signal sequence is selected from the group consisting of the signal sequence of Trichoderma CBHI, the signal sequence of Trichoderma CBHII, the signal sequence of Trichoderma EGI, the signal sequence of Trichoderma EGII, amino acids 1–19 of SEQ ID NO: 8, and amino acids 1–19 of SEQ ID NO: 2.

84. The method of claim 77, wherein said DNA construct is provided by a vector selected from the group consisting of pALK171, pALK172, pALK173A, pALK173B, and a fragment thereof that encodes the phytase having the amino acid sequence of amino acids 1–467 of SEQ ID NO: 8, or a catalytically active fragment thereof.

85. The method of claim 77, wherein said DNA construct is provided by a vector selected from the group consisting of pALK532, pALK533, and a fragment thereof that encodes the pH 2.5 acid phosphatase having the amino acid sequence of amino acids 1–479 of SEQ ID NO: 2, or a catalytically active fragment thereof.

86. A method of cloning a fusion of the *Trichoderma reesei* cbh1 promoter to the *Aspergillus niger* var. *awamori* phytase signal sequence, wherein said method comprises polymerase chain amplification of a fusion of the cbh1 promoter with phytase signal sequence using a 5' primer having SEQ ID NO: 9 and a 3' primer having SEQ ID NO: 10.

87. A method of cloning a fusion of DNA encoding the *Trichoderma reesei* CBHI signal sequence to the *Aspergillus niger* var. *awamori* mature phytase coding sequence, wherein said method comprises polymerase chain amplification of a sequence encoding a fusion of the DNA encoding said CBHI signal sequence and said mature phytase coding sequence with a 5' primer having SEQ ID NO: 11 and a 3' primer having SEQ ID NO: 12.

88. A method of cloning a fusion of the *Trichoderma reesei* cbh1 promoter to the *Aspergillus niger* var. *awamori* pH 2.5 acid phosphatase signal sequence, wherein said method comprises polymerase chain amplification of a sequence encoding a fusion of said cbh1 promoter and said signal sequence with a 5' primer having SEQ ID NO: 15 and a 3' primer having SEQ ID NO: 14.

89. A method of cloning a fusion of DNA encoding the *Trichoderma reesei* CBHI signal sequence to the *Aspergillus niger* var. *awamori* coding sequence of the mature pH 2.5 acid phosphatase, wherein said method comprises polymerase chain amplification of a sequence encoding a fusion of the DNA encoding said CBHI signal sequence and said mature pH 2.5 acid phosphatase coding sequence with a 5' primer having SEQ ID NO: 13 and a 3' primer having SEQ ID NO: 14.

90. A method of detecting a nucleic acid molecule encoding a phytase, said method comprising
 (a) hybridizing DNA suspected of encoding said phytase to DNA having the sequence of SEQ ID NO: 7; and
 (b) detecting the formation of the resulting double-stranded nucleic acid molecule.

91. A method of detecting a nucleic acid molecule encoding a pH 2.5 acid phosphatase, said method comprising
 (a) hybridizing DNA suspected of encoding said phytase to DNA having the sequence of SEQ ID NO: 1; and
 (b) detecting the formation of the resulting double-stranded nucleic acid molecule.

* * * * *

SEQUENCE LISTING ( 1 ) GENERAL INFORMATION:

( i i i ) NUMBER OF SEQUENCES: 69

( 2 ) INFORMATION FOR SEQ ID NO:1:

( i ) SEQUENCE CHARACTERISTICS:
      ( A ) LENGTH: 2071 base pairs
      ( B ) TYPE: nucleic acid
      ( C ) STRANDEDNESS: single
      ( D ) TOPOLOGY: both ( i x ) FEATURE:
      ( A ) NAME/KEY: CDS
      ( B ) LOCATION: join(136..915, 970..1089, 1142..1245, 1305..1737)

( x i ) SEQUENCE DESCRIPTION: SEQ ID NO:1:

```
GCATGCTGGA  CCGCAATCTC  CGATCGCCGG  GTATAAAAGG  TCCTCCAAAC  CCCTCTCGGT         60

CGATATGTAC  CCCGCTCGTC  ATCTCCAATC  CTCTCGAGAG  CACCTTCTCC  AGCTTTTGTC        120

AATTGTACCT  TCGCA ATG CCT CGC ACC TCT CTC CTC ACC CTG GCC TGT GCT            171
                  Met Pro Arg Thr Ser Leu Leu Thr Leu Ala Cys Ala
                   1               5                       10

CTG GCC ACG GGC GCA TCC GCT TTC TCC TAC GGC GCT GCC ATT CCT CAG             219
Leu Ala Thr Gly Ala Ser Ala Phe Ser Tyr Gly Ala Ala Ile Pro Gln
         15              20                      25

TCA ACC CAG GAG AAG CAG TTC TCT CAG GAG TTC CGC GAT GGC TAC AGC             267
Ser Thr Gln Glu Lys Gln Phe Ser Gln Glu Phe Arg Asp Gly Tyr Ser
     30                  35                      40

ATC CTC AAG CAC TAC GGT GGT AAC GGA CCC TAC TCC GAG CGT GTG TCC             315
Ile Leu Lys His Tyr Gly Gly Asn Gly Pro Tyr Ser Glu Arg Val Ser
 45                  50                      55                  60

TAC GGT ATC GCT CGC GAT CCC CCG ACC AGC TGC GAG GTC GAT CAG GTC             363
Tyr Gly Ile Ala Arg Asp Pro Pro Thr Ser Cys Glu Val Asp Gln Val
                 65                      70                  75

ATC ATG GTC AAG CGT CAC GGA GAG CGC TAC CCG TCC CCT TCA GCC GGC             411
Ile Met Val Lys Arg His Gly Glu Arg Tyr Pro Ser Pro Ser Ala Gly
                 80                      85                  90

AAG GAC ATC GAA GAG GCC CTG GCC AAG GTC TAC AGC ATC AAC ACT ACT             459
Lys Asp Ile Glu Glu Ala Leu Ala Lys Val Tyr Ser Ile Asn Thr Thr
             95                     100                 105

GAA TAC AAG GGC GAC CTG GCC TTC CTG AAC GAC TGG ACC TAC TAC GTC             507
Glu Tyr Lys Gly Asp Leu Ala Phe Leu Asn Asp Trp Thr Tyr Tyr Val
         110                     115                 120

CCT AAT GAG TGC TAC TAC AAC GCC GAG ACC ACC AGC GGC CCC TAC GCC             555
Pro Asn Glu Cys Tyr Tyr Asn Ala Glu Thr Thr Ser Gly Pro Tyr Ala
125                     130                     135                 140

GGT TTG CTG GAC GCG TAC AAC CAT GGC AAC GAT TAC AAG GCT CGC TAC             603
Gly Leu Leu Asp Ala Tyr Asn His Gly Asn Asp Tyr Lys Ala Arg Tyr
                 145                     150                     155

GGC CAC CTC TGG AAC GGT GAG ACG GTC GTG CCC TTC TTT TCT AGT GGC             651
```

```
              Gly His Leu Trp Asn Gly Glu Thr Val Val Pro Phe Phe Ser Ser Gly
                      160                 165                 170

TAC GGA CGT GTC ATC GAG ACG GCC CGC AAG TTC GGT GAG GGT TTC TTT              699
Tyr Gly Arg Val Ile Glu Thr Ala Arg Lys Phe Gly Glu Gly Phe Phe
        175                 180                 185

GGC TAC AAC TAC TCC ACC AAC GCT GCC CTC AAC ATC ATC TCC GAG TCC              747
Gly Tyr Asn Tyr Ser Thr Asn Ala Ala Leu Asn Ile Ile Ser Glu Ser
        190                 195                 200

GAG GTC ATG GGC GCG GAC AGC CTC ACG CCC ACC TGT GAC ACC GAC AAC              795
Glu Val Met Gly Ala Asp Ser Leu Thr Pro Thr Cys Asp Thr Asp Asn
205                 210                 215                 220

GAC CAG ACC ACC TGC GAC AAC CTG ACT TAC CAG CTG CCC CAG TTC AAG              843
Asp Gln Thr Thr Cys Asp Asn Leu Thr Tyr Gln Leu Pro Gln Phe Lys
                225                 230                 235

GTC GCT GCT GCC CGC CTA AAC TCC CAG AAC CCC GGC ATG AAC CTC ACC              891
Val Ala Ala Ala Arg Leu Asn Ser Gln Asn Pro Gly Met Asn Leu Thr
                240                 245                 250

GCA TCT GAT GTC TAC AAC CTG ATG GGTATGTGAT TACGGTACAA TCATTGGCTC             945
Ala Ser Asp Val Tyr Asn Leu Met
                255                 260

AAACCTCCAG CTGACAGCAT CCTA GTT ATG GCC TCC TTT GAG CTC AAT GCT               996
                          Val Met Ala Ser Phe Glu Leu Asn Ala
                                         265

CGT CCC TTC TCC AAC TGG ATC AAC GCC TTT ACC CAG GAC GAA TGG GTC             1044
Arg Pro Phe Ser Asn Trp Ile Asn Ala Phe Thr Gln Asp Glu Trp Val
270                 275                 280                 285

AGC TTC GGT TAC GTT GAG GAT TTG AAC TAC TAC TAC TGC GCT GGG                 1089
Ser Phe Gly Tyr Val Glu Asp Leu Asn Tyr Tyr Tyr Cys Ala Gly
                290                 295                 300

TGAGTTTACC ATTTGATCCA TTATTGTCTT GGATCAGCTA ACGATCGATA GT CCC               1144
                                                           Pro

GGT GAC AAG AAC ATG GCT GCT GTG GGT GCC GTC TAC GCC AAC GCC AGT             1192
Gly Asp Lys Asn Met Ala Ala Val Gly Ala Val Tyr Ala Asn Ala Ser
            305                 310                 315

CTC ACC CTC CTG AAC CAG GGA CCC AAG GAA GCC GGC TCC TTG TTC TTC             1240
Leu Thr Leu Leu Asn Gln Gly Pro Lys Glu Ala Gly Ser Leu Phe Phe
            320                 325                 330

AAC TT GTACGTTCTCG GCAGAATCAG AGTCTCACAA AAAGAAACTC TTCACTAACA              1296
Asn Phe
    335

TATAGTAG T GCC CAC GAC ACC AAC ATC ACC CCC ATC CTC GCC GCC CTA              1344
          Ala His Asp Thr Asn Ile Thr Pro Ile Leu Ala Ala Leu
                      340                 345

GGC GTC CTC ATC CCC AAC GAG GAC CTT CCT CTT GAC CGG GTC GCC TTC             1392
Gly Val Leu Ile Pro Asn Glu Asp Leu Pro Leu Asp Arg Val Ala Phe
350                 355                 360

GGC AAC CCC TAC TCG ATC GGC AAC ATC GTG CCC ATG GGT GGC CAT CTG             1440
Gly Asn Pro Tyr Ser Ile Gly Asn Ile Val Pro Met Gly Gly His Leu
365                 370                 375                 380

ACC ATC GAG CGT CTC AGC TGC CAG GCC ACC GCC CTC TCG GAC GAG GGT             1488
Thr Ile Glu Arg Leu Ser Cys Gln Ala Thr Ala Leu Ser Asp Glu Gly
            385                 390                 395

ACC TAC GTG CGT CTG GTG CTG AAC GAG GCT GTA CTC CCC TTC AAC GAC             1536
Thr Tyr Val Arg Leu Val Leu Asn Glu Ala Val Leu Pro Phe Asn Asp
                400                 405                 410

TGC ACC TCC GGA CCG GGC TAC TCC TGC CCT CTG GCC AAC TAC ACC TCC             1584
Cys Thr Ser Gly Pro Gly Tyr Ser Cys Pro Leu Ala Asn Tyr Thr Ser
            415                 420                 425

ATC CTG AAC AAG AAT CTG CCA GAC TAC ACG ACC ACC TGC AAT GTC TCT             1632
Ile Leu Asn Lys Asn Leu Pro Asp Tyr Thr Thr Thr Cys Asn Val Ser
```

```
                430                           435                           440
GCG  TCC  TAC  CCG  CAG  TAT  CTG  AGC  TTC  TGG  TGG  AAC  TAC  AAC  ACC  ACG                    1680
Ala  Ser  Tyr  Pro  Gln  Tyr  Leu  Ser  Phe  Trp  Trp  Asn  Tyr  Asn  Thr  Thr
445                      450                           455                      460

ACG  GAG  CTG  AAC  TAC  CGC  TCT  AGC  CCT  ATT  GCC  TGC  CAG  GAG  GGT  GAT                    1728
Thr  Glu  Leu  Asn  Tyr  Arg  Ser  Ser  Pro  Ile  Ala  Cys  Gln  Glu  Gly  Asp
                         465                           470                      475

GCT  ATG  GAC  TAGATGCAGA  GGGGTAGGTC  CCGGGATACT  TTAGTGATGA                                      1777
Ala  Met  Asp

TTGATATTCA  AGTTGGTGG  TGACGATCAC  CTTGTTAATA  GTCTTGTACA  GTCATACGGT                              1837

GAATGTAAAT  AATGATAATA  GCAATGATAC  ATGTTGGAAT  CTCGTTTTGT  TCTTTGTGTG                             1897

CATAGGCGCT  TTGGGGGTGT  ATTTTTAGGC  GTTAGACTTA  TTTTCAATTC  GTGTATAATG                             1957

CGGTCAGTAA  ATGAATCATC  AATTATTCAA  ATGCAATGCT  GTATACGTGA  AACTATTGGG                             2017

TTAAGACGCA  GCTACTAGCT  GACTGCTTGG  TTACTTTCTG  TGTACACCGC  ATGC                                   2071
```

( 2 ) INFORMATION FOR SEQ ID NO:2:

( i ) SEQUENCE CHARACTERISTICS:
        ( A ) LENGTH: 479 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Arg  Thr  Ser  Leu  Leu  Thr  Leu  Ala  Cys  Ala  Leu  Ala  Thr  Gly
 1                    5                        10                       15

Ala  Ser  Ala  Phe  Ser  Tyr  Gly  Ala  Ala  Ile  Pro  Gln  Ser  Thr  Gln  Glu
               20                       25                       30

Lys  Gln  Phe  Ser  Gln  Glu  Phe  Arg  Asp  Gly  Tyr  Ser  Ile  Leu  Lys  His
               35                       40                       45

Tyr  Gly  Gly  Asn  Gly  Pro  Tyr  Ser  Glu  Arg  Val  Ser  Tyr  Gly  Ile  Ala
          50                       55                       60

Arg  Asp  Pro  Pro  Thr  Ser  Cys  Glu  Val  Asp  Gln  Val  Ile  Met  Val  Lys
 65                       70                       75                       80

Arg  His  Gly  Glu  Arg  Tyr  Pro  Ser  Pro  Ser  Ala  Gly  Lys  Asp  Ile  Glu
                    85                       90                       95

Glu  Ala  Leu  Ala  Lys  Val  Tyr  Ser  Ile  Asn  Thr  Thr  Glu  Tyr  Lys  Gly
               100                      105                      110

Asp  Leu  Ala  Phe  Leu  Asn  Asp  Trp  Thr  Tyr  Tyr  Val  Pro  Asn  Glu  Cys
               115                      120                      125

Tyr  Tyr  Asn  Ala  Glu  Thr  Thr  Ser  Gly  Pro  Tyr  Ala  Gly  Leu  Leu  Asp
          130                      135                      140

Ala  Tyr  Asn  His  Gly  Asn  Asp  Tyr  Lys  Ala  Arg  Tyr  Gly  His  Leu  Trp
145                      150                      155                      160

Asn  Gly  Glu  Thr  Val  Val  Pro  Phe  Phe  Ser  Ser  Gly  Tyr  Gly  Arg  Val
                    165                      170                      175

Ile  Glu  Thr  Ala  Arg  Lys  Phe  Gly  Glu  Gly  Phe  Phe  Gly  Tyr  Asn  Tyr
               180                      185                      190

Ser  Thr  Asn  Ala  Ala  Leu  Asn  Ile  Ile  Ser  Glu  Ser  Glu  Val  Met  Gly
          195                      200                      205

Ala  Asp  Ser  Leu  Thr  Pro  Thr  Cys  Asp  Thr  Asp  Asn  Asp  Gln  Thr  Thr
          210                      215                      220

Cys  Asp  Asn  Leu  Thr  Tyr  Gln  Leu  Pro  Gln  Phe  Lys  Val  Ala  Ala  Ala
225                      230                      235                      240
```

| Arg | Leu | Asn | Ser | Gln 245 | Asn | Pro | Gly | Met 250 | Asn | Leu | Thr | Ala | Ser 255 | Asp | Val |
|---|---|---|---|---|---|---|---|---|---|---|---|---|---|---|---|
| Tyr | Asn | Leu | Met 260 | Val | Met | Ala | Ser | Phe 265 | Glu | Leu | Asn | Ala | Arg 270 | Pro | Phe |
| Ser | Asn | Trp 275 | Ile | Asn | Ala | Phe | Thr 280 | Gln | Asp | Glu | Trp | Val 285 | Ser | Phe | Gly |
| Tyr | Val 290 | Glu | Asp | Leu | Asn | Tyr 295 | Tyr | Cys | Ala | Gly 300 | Pro | Gly | Asp | Lys |
| Asn 305 | Met | Ala | Ala | Val | Gly 310 | Ala | Val | Tyr | Ala | Asn 315 | Ala | Ser | Leu | Thr | Leu 320 |
| Leu | Asn | Gln | Gly | Pro 325 | Lys | Glu | Ala | Gly | Ser 330 | Leu | Phe | Phe | Asn | Phe 335 | Ala |
| His | Asp | Thr | Asn 340 | Ile | Thr | Pro | Ile | Leu 345 | Ala | Ala | Leu | Gly | Val 350 | Leu | Ile |
| Pro | Asn | Glu 355 | Asp | Leu | Pro | Leu | Asp 360 | Arg | Val | Ala | Phe | Gly 365 | Asn | Pro | Tyr |
| Ser | Ile 370 | Gly | Asn | Ile | Val | Pro 375 | Met | Gly | Gly | His | Leu 380 | Thr | Ile | Glu | Arg |
| Leu 385 | Ser | Cys | Gln | Ala | Thr 390 | Ala | Leu | Ser | Asp | Glu 395 | Gly | Thr | Tyr | Val | Arg 400 |
| Leu | Val | Leu | Asn | Glu 405 | Ala | Val | Leu | Pro | Phe 410 | Asn | Asp | Cys | Thr | Ser 415 | Gly |
| Pro | Gly | Tyr | Ser 420 | Cys | Pro | Leu | Ala | Asn 425 | Tyr | Thr | Ser | Ile | Leu 430 | Asn | Lys |
| Asn | Leu | Pro 435 | Asp | Tyr | Thr | Thr | Thr 440 | Cys | Asn | Val | Ser | Ala 445 | Ser | Tyr | Pro |
| Gln | Tyr 450 | Leu | Ser | Phe | Trp | Trp 455 | Asn | Tyr | Asn | Thr | Thr 460 | Thr | Glu | Leu | Asn |
| Tyr 465 | Arg | Ser | Ser | Pro | Ile 470 | Ala | Cys | Gln | Glu | Gly 475 | Asp | Ala | Met | Asp | |

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: both ( x i ) SEQUENCE DESCRIPTION: SEQ ID NO:3:

TAYTAYGGNC AYGGNGC                                       17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: both ( x i ) SEQUENCE DESCRIPTION: SEQ ID NO:4:

CARGGNGTNG GNTAYGC                                       17

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: both ( x i ) SEQUENCE DESCRIPTION: SEQ ID NO:5:

TAYGTNGARA TGATGCARAA                                                                                    20

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: both ( x i ) SEQUENCE DESCRIPTION: SEQ ID NO:6:

ATGATGCAAA ATCAAGCTGA ACA                                                                                23

( 2 ) INFORMATION FOR SEQ ID NO:7:

( i ) SEQUENCE CHARACTERISTICS:
        ( A ) LENGTH: 2363 base pairs
        ( B ) TYPE: nucleic acid
        ( C ) STRANDEDNESS: single
        ( D ) TOPOLOGY: both ( i x ) FEATURE:
        ( A ) NAME/KEY: CDS
        ( B ) LOCATION: join(404..447, 550..1906)

( x i ) SEQUENCE DESCRIPTION: SEQ ID NO:7:

```
CATCCAGGCA  CCCTTTCCCA  ACGGGGGAAC  TTCCGTTGTC  CACGTGCCCT  GGTTCAGCCA       60

ATCAAAGCGT  CCCACGGCAA  TGCTGGATCA  ACGATCAACT  TGAATGCAAT  AAATGAAGAT      120

GCAACTAACA  CCATCTGTTG  CCTTTCTCTC  GAGAAAGCTC  CTCCACTTCT  CACACTAGAT      180

TTATCCGTTC  CTTGTCGACT  TCCCGTCCCA  TTCGGCCTCG  TCCACTGAAG  ATCTATCCCA      240

CCATTGCACG  TGGGCCACCT  TTGTGAGCTT  CTAACCTGAA  CTGGTAGAGT  ATCACACAAC      300

ATGCGAAAGT  GGGATGAAGG  GGTTATATGA  GGACCGTCCG  GTCCGGCGCG  ATGGCCGTAG      360

CTGCCAATCG  CTGCTGTGCA  AGAAATTTCT  TCTCATAGGC  ATC ATG GGC GTC TCT         415
                                                 Met Gly Val Ser
                                                  1

GCT GTT CTA CTT CCT TTG TAT CTC CTA GCT   GG  GTATGCTAAG                    457
Ala Val Leu Leu Pro Leu Tyr Leu Leu Ala   Gly
 5                    10                   15

CACCGCTATC  TAAGTCTGAT  AAGGACCCTC  TTTGCCGAGG  GCCCCTGAAG  CTCGGACTGT      517

GTGGGACTAC  TGATCGCTGA  CAATCTGTGC AG A GTC ACC TCC GGA CTG GCA             568
                                     Val Thr Ser Gly Leu Ala
                                                          20

GTC CCC GCC TCG AGA AAT CAA TCC ACT TGC GAT ACG GTC GAT CAA GGG            616
Val Pro Ala Ser Arg Asn Gln Ser Thr Cys Asp Thr Val Asp Gln Gly
              25                  30                  35

TAT CAA TGC TTC TCC GAG ACT TCG CAT CTT TGG GGT CAA TAC GCG CCG            664
Tyr Gln Cys Phe Ser Glu Thr Ser His Leu Trp Gly Gln Tyr Ala Pro
         40                  45                  50

TTC TTC TCT CTG GCA AAC GAA TCG GCC ATC TCC CCT GAT GTG CCC GCC            712
Phe Phe Ser Leu Ala Asn Glu Ser Ala Ile Ser Pro Asp Val Pro Ala
     55                  60                  65

GGT TGC AGA GTC ACT TTC GCT CAG GTC CTC TCC CGT CAT GGA GCG CGG            760
Gly Cys Arg Val Thr Phe Ala Gln Val Leu Ser Arg His Gly Ala Arg
 70                  75                  80                  85

TAT CCG ACC GAG TCC AAG GGC AAG AAA TAC TCC GCT CTC ATT GAG GAG            808
Tyr Pro Thr Glu Ser Lys Gly Lys Lys Tyr Ser Ala Leu Ile Glu Glu
         90                  95                 100

ATC CAG CAG AAC GTG ACC ACC TTT GAT GGA AAA TAT GCC TTC CTG AAG            856
Ile Gln Gln Asn Val Thr Thr Phe Asp Gly Lys Tyr Ala Phe Leu Lys
```

|     |     |     | 105 |     |     |     |     | 110 |     |     |     |     | 115 |     |     |      |
|-----|-----|-----|-----|-----|-----|-----|-----|-----|-----|-----|-----|-----|-----|-----|-----|------|
| ACA | TAC | AAC | TAC | AGC | TTG | GGT | GCA | GAT | GAC | CTG | ACT | CCC | TTC | GGA | GAG | 904  |
| Thr | Tyr | Asn | Tyr | Ser | Leu | Gly | Ala | Asp | Asp | Leu | Thr | Pro | Phe | Gly | Glu |      |
|     |     | 120 |     |     |     |     | 125 |     |     |     |     | 130 |     |     |     |      |
| CAG | GAG | CTA | GTC | AAC | TCC | GGC | ATC | AAG | TTC | TAC | CAG | CGA | TAC | GAA | TCG | 952  |
| Gln | Glu | Leu | Val | Asn | Ser | Gly | Ile | Lys | Phe | Tyr | Gln | Arg | Tyr | Glu | Ser |      |
|     | 135 |     |     |     |     | 140 |     |     |     |     | 145 |     |     |     |     |      |
| CTC | ACA | AGG | AAC | ATC | ATT | CCG | TTC | ATC | CGA | TCC | TCT | GGC | TCC | AGC | CGC | 1000 |
| Leu | Thr | Arg | Asn | Ile | Ile | Pro | Phe | Ile | Arg | Ser | Ser | Gly | Ser | Ser | Arg |      |
| 150 |     |     |     |     | 155 |     |     |     |     | 160 |     |     |     |     | 165 |      |
| GTG | ATC | GCC | TCC | GGC | GAG | AAA | TTC | ATT | GAG | GGC | TTC | CAG | AGC | ACC | AAG | 1048 |
| Val | Ile | Ala | Ser | Gly | Glu | Lys | Phe | Ile | Glu | Gly | Phe | Gln | Ser | Thr | Lys |      |
|     |     |     |     | 170 |     |     |     |     | 175 |     |     |     |     | 180 |     |      |
| CTG | AAG | GAT | CCT | CGT | GCC | CAG | CCG | GGC | CAA | TCG | TCG | CCC | AAG | ATC | GAC | 1096 |
| Leu | Lys | Asp | Pro | Arg | Ala | Gln | Pro | Gly | Gln | Ser | Ser | Pro | Lys | Ile | Asp |      |
|     |     |     | 185 |     |     |     |     | 190 |     |     |     |     | 195 |     |     |      |
| GTG | GTC | ATT | TCC | GAG | GCC | AGC | TCA | TCC | AAC | AAC | ACT | CTC | GAC | CCA | GGC | 1144 |
| Val | Val | Ile | Ser | Glu | Ala | Ser | Ser | Ser | Asn | Asn | Thr | Leu | Asp | Pro | Gly |      |
|     |     | 200 |     |     |     |     | 205 |     |     |     |     | 210 |     |     |     |      |
| ACC | TGC | ACT | GTC | TTT | GAA | GAC | AGC | GAA | TTG | GCC | GAT | ACC | GTC | GAA | GCC | 1192 |
| Thr | Cys | Thr | Val | Phe | Glu | Asp | Ser | Glu | Leu | Ala | Asp | Thr | Val | Glu | Ala |      |
|     | 215 |     |     |     |     | 220 |     |     |     |     | 225 |     |     |     |     |      |
| AAT | TTC | ACC | GCC | ACG | TTC | GCC | CCC | TCC | ATT | CGT | CAA | CGT | CTG | GAG | AAC | 1240 |
| Asn | Phe | Thr | Ala | Thr | Phe | Ala | Pro | Ser | Ile | Arg | Gln | Arg | Leu | Glu | Asn |      |
| 230 |     |     |     |     | 235 |     |     |     |     | 240 |     |     |     |     | 245 |      |
| GAC | CTG | TCT | GGC | GTG | ACT | CTC | ACA | GAC | ACA | GAA | GTG | ACC | TAC | CTC | ATG | 1288 |
| Asp | Leu | Ser | Gly | Val | Thr | Leu | Thr | Asp | Thr | Glu | Val | Thr | Tyr | Leu | Met |      |
|     |     |     |     | 250 |     |     |     |     | 255 |     |     |     |     | 260 |     |      |
| GAC | ATG | TGC | TCC | TTC | GAC | ACC | ATC | TCC | ACC | AGC | ACC | GTC | GAC | ACC | AAG | 1336 |
| Asp | Met | Cys | Ser | Phe | Asp | Thr | Ile | Ser | Thr | Ser | Thr | Val | Asp | Thr | Lys |      |
|     |     |     | 265 |     |     |     |     | 270 |     |     |     |     | 275 |     |     |      |
| CTG | TCC | CCC | TTC | TGT | GAC | CTG | TTC | ACC | CAT | GAC | GAA | TGG | ATC | CAC | TAC | 1384 |
| Leu | Ser | Pro | Phe | Cys | Asp | Leu | Phe | Thr | His | Asp | Glu | Trp | Ile | His | Tyr |      |
|     |     | 280 |     |     |     |     | 285 |     |     |     |     | 290 |     |     |     |      |
| GAC | TAC | CTC | CAG | TCC | CTG | AAA | AAA | TAC | TAC | GGC | CAT | GGC | GCA | GGT | AAC | 1432 |
| Asp | Tyr | Leu | Gln | Ser | Leu | Lys | Lys | Tyr | Tyr | Gly | His | Gly | Ala | Gly | Asn |      |
|     | 295 |     |     |     |     | 300 |     |     |     |     | 305 |     |     |     |     |      |
| CCG | CTC | GGC | CCG | ACC | CAG | GGC | GTC | GGC | TAC | GCT | AAC | GAG | CTC | ATC | GCC | 1480 |
| Pro | Leu | Gly | Pro | Thr | Gln | Gly | Val | Gly | Tyr | Ala | Asn | Glu | Leu | Ile | Ala |      |
| 310 |     |     |     |     | 315 |     |     |     |     | 320 |     |     |     |     | 325 |      |
| CGT | CTC | ACC | CAC | TCG | CCT | GTC | CAC | GAT | GAC | ACC | AGC | TCC | AAC | CAC | ACC | 1528 |
| Arg | Leu | Thr | His | Ser | Pro | Val | His | Asp | Asp | Thr | Ser | Ser | Asn | His | Thr |      |
|     |     |     |     | 330 |     |     |     |     | 335 |     |     |     |     | 340 |     |      |
| TTG | GAC | TCG | AAC | CCA | GCT | ACC | TTC | CCG | CTC | AAC | TCT | ACT | CTC | TAC | GCG | 1576 |
| Leu | Asp | Ser | Asn | Pro | Ala | Thr | Phe | Pro | Leu | Asn | Ser | Thr | Leu | Tyr | Ala |      |
|     |     |     | 345 |     |     |     |     | 350 |     |     |     |     | 355 |     |     |      |
| GAC | TTT | TCC | CAC | GAT | AAC | GGC | ATC | ATC | TCT | ATC | CTC | TTT | GCT | TTG | GGT | 1624 |
| Asp | Phe | Ser | His | Asp | Asn | Gly | Ile | Ile | Ser | Ile | Leu | Phe | Ala | Leu | Gly |      |
|     |     | 360 |     |     |     |     | 365 |     |     |     |     | 370 |     |     |     |      |
| CTG | TAC | AAC | GGC | ACT | AAG | CCG | CTG | TCT | ACC | ACG | ACC | GTG | GAG | AAT | ATC | 1672 |
| Leu | Tyr | Asn | Gly | Thr | Lys | Pro | Leu | Ser | Thr | Thr | Thr | Val | Glu | Asn | Ile |      |
|     | 375 |     |     |     |     | 380 |     |     |     |     | 385 |     |     |     |     |      |
| ACC | CAG | ACA | GAT | GGG | TTC | TCG | TCT | GCT | TGG | ACG | GTT | CCG | TTT | GCT | TCG | 1720 |
| Thr | Gln | Thr | Asp | Gly | Phe | Ser | Ser | Ala | Trp | Thr | Val | Pro | Phe | Ala | Ser |      |
| 390 |     |     |     |     | 395 |     |     |     |     | 400 |     |     |     |     | 405 |      |
| CGT | CTG | TAC | GTC | GAG | ATG | ATG | CAG | TGC | CAG | GCC | GAG | CAG | GAG | CCG | CTG | 1768 |
| Arg | Leu | Tyr | Val | Glu | Met | Met | Gln | Cys | Gln | Ala | Glu | Gln | Glu | Pro | Leu |      |
|     |     |     |     | 410 |     |     |     |     | 415 |     |     |     |     | 420 |     |      |
| GTC | CGT | GTC | TTG | GTT | AAT | GAT | CGC | GTT | GTC | CCG | CTG | CAT | GGG | TGT | CCA | 1816 |
| Val | Arg | Val | Leu | Val | Asn | Asp | Arg | Val | Val | Pro | Leu | His | Gly | Cys | Pro |      |

-continued

```
                    425                           430                            435
ATT  GAT  GCT  TTG  GGG  AGA  TGT  ACC  CGG  GAT  AGC  TTT  GTG  AGG  GGG  TTG      1864
Ile  Asp  Ala  Leu  Gly  Arg  Cys  Thr  Arg  Asp  Ser  Phe  Val  Arg  Gly  Leu
          440                      445                     450

AGC  TTT  GCT  AGA  TCT  GGG  GGT  GAT  TGG  GCG  GAG  TGT  TCT  GCT                1906
Ser  Phe  Ala  Arg  Ser  Gly  Gly  Asp  Trp  Ala  Glu  Cys  Ser  Ala
          455                      460                     465

TAGCTGAACT  ACCTTGATGG  ATGGTATGTA  TCAATCAGAG  TACATATCAT  TACTTCATGT              1966

ATGTATTTAC  GAAGATGTAC  ATATCGAAAT  ATCGATGATG  ACTACTCCGG  TAGATATTTG              2026

GTCCCCTTCT  ATCCTTCGTT  CCACAACCAT  CGCACTCGAC  GTACAGCATA  ATACAACTTC              2086

AGCATTAACA  AACGAACAAA  TAATATTATA  CACTCCTCCC  CAATGCAATA  ACAACCGCAA              2146

TTCATACCTC  ATATAGATAC  AATACAATAC  ATCCATCCCT  ACCCTCAAGT  CCACCCATCC              2206

CATAATCAAA  TCCCTACTTA  CTCCTCCCCC  TTCCAGAAC   CCACCCCCGA  AGGAGTAATA              2266

GTAGTAGTAG  AAGAAGCAGA  CGACCTCTCC  ACCAACCTCT  TCGGCCTCTT  ATCCCCATAC              2326

GCTATACACA  CACGAACACA  CCAAATAGTC  AGCATGC                                         2363
```

( 2 ) INFORMATION FOR SEQ ID NO:8:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Gly  Val  Ser  Ala  Val  Leu  Leu  Pro  Leu  Tyr  Leu  Leu  Ala  Gly  Val
 1                    5                    10                       15

Thr  Ser  Gly  Leu  Ala  Val  Pro  Ala  Ser  Arg  Asn  Gln  Ser  Thr  Cys  Asp
               20                    25                       30

Thr  Val  Asp  Gln  Gly  Tyr  Gln  Cys  Phe  Ser  Glu  Thr  Ser  His  Leu  Trp
               35                    40                       45

Gly  Gln  Tyr  Ala  Pro  Phe  Phe  Ser  Leu  Ala  Asn  Glu  Ser  Ala  Ile  Ser
     50                    55                         60

Pro  Asp  Val  Pro  Ala  Gly  Cys  Arg  Val  Thr  Phe  Ala  Gln  Val  Leu  Ser
65                    70                    75                            80

Arg  His  Gly  Ala  Arg  Tyr  Pro  Thr  Glu  Ser  Lys  Gly  Lys  Lys  Tyr  Ser
                    85                    90                       95

Ala  Leu  Ile  Glu  Ile  Gln  Gln  Asn  Val  Thr  Thr  Phe  Asp  Gly  Lys
               100                   105                      110

Tyr  Ala  Phe  Leu  Lys  Thr  Tyr  Asn  Tyr  Ser  Leu  Gly  Ala  Asp  Asp  Leu
          115                        120                      125

Thr  Pro  Phe  Gly  Glu  Gln  Glu  Leu  Val  Asn  Ser  Gly  Ile  Lys  Phe  Tyr
     130                       135                      140

Gln  Arg  Tyr  Glu  Ser  Leu  Thr  Arg  Asn  Ile  Ile  Pro  Phe  Ile  Arg  Ser
145                        150                   155                       160

Ser  Gly  Ser  Ser  Arg  Val  Ile  Ala  Ser  Gly  Glu  Lys  Phe  Ile  Glu  Gly
                    165                   170                      175

Phe  Gln  Ser  Thr  Lys  Leu  Lys  Asp  Pro  Arg  Ala  Gln  Pro  Gly  Gln  Ser
               180                   185                      190

Ser  Pro  Lys  Ile  Asp  Val  Val  Ile  Ser  Glu  Ala  Ser  Ser  Ser  Asn  Asn
          195                        200                      205

Thr  Leu  Asp  Pro  Gly  Thr  Cys  Thr  Val  Phe  Glu  Asp  Ser  Glu  Leu  Ala
     210                       215                      220
```

| Asp | Thr | Val | Glu | Ala | Asn | Phe | Thr | Ala | Thr | Phe | Ala | Pro | Ser | Ile | Arg |
|---|---|---|---|---|---|---|---|---|---|---|---|---|---|---|---|
| 225 | | | | | 230 | | | | | 235 | | | | | 240 |
| Gln | Arg | Leu | Glu | Asn | Asp | Leu | Ser | Gly | Val | Thr | Leu | Thr | Asp | Thr | Glu |
| | | | | 245 | | | | | 250 | | | | | 255 | |
| Val | Thr | Tyr | Leu | Met | Asp | Met | Cys | Ser | Phe | Asp | Thr | Ile | Ser | Thr | Ser |
| | | | 260 | | | | | 265 | | | | | 270 | | |
| Thr | Val | Asp | Thr | Lys | Leu | Ser | Pro | Phe | Cys | Asp | Leu | Phe | Thr | His | Asp |
| | | 275 | | | | | 280 | | | | | 285 | | | |
| Glu | Trp | Ile | His | Tyr | Asp | Tyr | Leu | Gln | Ser | Leu | Lys | Lys | Tyr | Tyr | Gly |
| | 290 | | | | | 295 | | | | | 300 | | | | |
| His | Gly | Ala | Gly | Asn | Pro | Leu | Gly | Pro | Thr | Gln | Gly | Val | Gly | Tyr | Ala |
| 305 | | | | | 310 | | | | | 315 | | | | | 320 |
| Asn | Glu | Leu | Ile | Ala | Arg | Leu | Thr | His | Ser | Pro | Val | His | Asp | Asp | Thr |
| | | | | 325 | | | | | 330 | | | | | 335 | |
| Ser | Ser | Asn | His | Thr | Leu | Asp | Ser | Asn | Pro | Ala | Thr | Phe | Pro | Leu | Asn |
| | | | 340 | | | | | 345 | | | | | 350 | | |
| Ser | Thr | Leu | Tyr | Ala | Asp | Phe | Ser | His | Asp | Asn | Gly | Ile | Ile | Ser | Ile |
| | | 355 | | | | | 360 | | | | | 365 | | | |
| Leu | Phe | Ala | Leu | Gly | Leu | Tyr | Asn | Gly | Thr | Lys | Pro | Leu | Ser | Thr | Thr |
| | 370 | | | | | 375 | | | | | 380 | | | | |
| Thr | Val | Glu | Asn | Ile | Thr | Gln | Thr | Asp | Gly | Phe | Ser | Ser | Ala | Trp | Thr |
| 385 | | | | | 390 | | | | | 395 | | | | | 400 |
| Val | Pro | Phe | Ala | Ser | Arg | Leu | Tyr | Val | Glu | Met | Met | Gln | Cys | Gln | Ala |
| | | | | 405 | | | | | 410 | | | | | 415 | |
| Glu | Gln | Glu | Pro | Leu | Val | Arg | Val | Leu | Val | Asn | Asp | Arg | Val | Val | Pro |
| | | | 420 | | | | | 425 | | | | | 430 | | |
| Leu | His | Gly | Cys | Pro | Ile | Asp | Ala | Leu | Gly | Arg | Cys | Thr | Arg | Asp | Ser |
| | | 435 | | | | | 440 | | | | | 445 | | | |
| Phe | Val | Arg | Gly | Leu | Ser | Phe | Ala | Arg | Ser | Gly | Gly | Asp | Trp | Ala | Glu |
| | 450 | | | | | 455 | | | | | 460 | | | | |
| Cys | Ser | Ala | | | | | | | | | | | | | |
| 465 | | | | | | | | | | | | | | | |

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: both ( x i ) SEQUENCE DESCRIPTION: SEQ ID NO:9:

CAACCGCGGA CTGCGCATCA TGGGCGTCTC TGCTGTTCT        39

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: both ( x i ) SEQUENCE DESCRIPTION: SEQ ID NO:10:

ATTTCTCGAG GCGGGGACTG CC        22

( 2 ) INFORMATION FOR SEQ ID NO:11:

( i ) SEQUENCE CHARACTERISTICS:
        ( A ) LENGTH: 46 base pairs
        ( B ) TYPE: nucleic acid (C) STRANDEDNESS: single
(D) TOPOLOGY: both (x i) SEQUENCE DESCRIPTION: SEQ ID NO:11:

CTCGGCCTTC TTGGCGAGAG CTCGTGCTCT GGCAGTCCCC GCCTCG 46

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: both (x i) SEQUENCE DESCRIPTION: SEQ ID NO:12:

TTGGTGTCGA CGGTGCTGGT GGAG 24

(2) INFORMATION FOR SEQ ID NO:13:

(i) SEQUENCE CHARACTERISTICS:
        (A) LENGTH: 46 base pairs
        (B) TYPE: nucleic acid
        (C) STRANDEDNESS: single
        (D) TOPOLOGY: both (x i) SEQUENCE DESCRIPTION: SEQ ID NO:13:

CTCGGCCTTC TTGGCCACAG CTCGTGCTTT CTCCTACGGC GCTGCC 46

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: both (x i) SEQUENCE DESCRIPTION: SEQ ID NO:14:

GCCATGGTTG TACGCGTCCA GCAAACCGGC 30

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: both (x i) SEQUENCE DESCRIPTION: SEQ ID NO:15:

CAACCGCGGA CTGCGCATCA TGCCTCGCAC CTCTCTCCT 39

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: both (x i) SEQUENCE DESCRIPTION: SEQ ID NO:16:

GAATTCCCGG GACCTACCCC TCTGCAT 27

(2) INFORMATION FOR SEQ ID NO:17:

(i) SEQUENCE CHARACTERISTICS:
        (A) LENGTH: 14 amino acids
        (B) TYPE: amino acid
        (D) TOPOLOGY: both ( x i ) SEQUENCE DESCRIPTION: SEQ ID NO:17:

Leu Ala Val Pro Ala Ser Arg Asn Gln Ser Ser Gly Asp Thr
1               5                   10

( 2 ) INFORMATION FOR SEQ ID NO:18:

( i ) SEQUENCE CHARACTERISTICS:
      ( A ) LENGTH: 7 amino acids
      ( B ) TYPE: amino acid
      ( D ) TOPOLOGY: both ( x i ) SEQUENCE DESCRIPTION: SEQ ID NO:18:

Arg His Gly Xaa Arg Xaa Pro
1               5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( D ) TOPOLOGY: both ( x i ) SEQUENCE DESCRIPTION: SEQ ID NO:19:

Lys Asp Pro Arg Ala
1               5

( 2 ) INFORMATION FOR SEQ ID NO:20:

( i ) SEQUENCE CHARACTERISTICS:
      ( A ) LENGTH: 15 amino acids
      ( B ) TYPE: amino acid
      ( D ) TOPOLOGY: both ( x i ) SEQUENCE DESCRIPTION: SEQ ID NO:20:

Tyr Tyr Gly His Leu Gly Ala Gly Asn Pro Leu Gly Pro Thr Gln
1               5                   10                  15

( 2 ) INFORMATION FOR SEQ ID NO:21:

( i ) SEQUENCE CHARACTERISTICS:
      ( A ) LENGTH: 11 amino acids
      ( B ) TYPE: amino acid
      ( D ) TOPOLOGY: both ( x i ) SEQUENCE DESCRIPTION: SEQ ID NO:21:

Thr Gly Tyr Val Gln Asn Tyr Val Gln Met Gln
1               5                   10

( 2 ) INFORMATION FOR SEQ ID NO:22:

( i ) SEQUENCE CHARACTERISTICS:
      ( A ) LENGTH: 9 amino acids
      ( B ) TYPE: amino acid
      ( D ) TOPOLOGY: both ( i x ) FEATURE:
      ( A ) NAME/KEY: Peptide
      ( B ) LOCATION: 6..7
      ( D ) OTHER INFORMATION: /label= Peptide
           / note= "When deduced from the DNA sequence the
           amino acids at positions 6 and 7 were found to be
           serine."

( x i ) SEQUENCE DESCRIPTION: SEQ ID NO:22:

Ala Gln Pro Gly Gln Ala Ala Pro Lys
1               5

( 2 ) INFORMATION FOR SEQ ID NO:23:

( i ) SEQUENCE CHARACTERISTICS:
  ( A ) LENGTH: 16 amino acids
  ( B ) TYPE: amino acid
  ( D ) TOPOLOGY: both ( x i ) SEQUENCE DESCRIPTION: SEQ ID NO:23:

Leu Tyr Val Glu Met Met Gln Asn Gln Ala Glu Gln Thr Pro Leu Val
1               5                   10                  15

( 2 ) INFORMATION FOR SEQ ID NO:24:

( i ) SEQUENCE CHARACTERISTICS:
  ( A ) LENGTH: 16 amino acids
  ( B ) TYPE: amino acid
  ( D ) TOPOLOGY: both ( x i ) SEQUENCE DESCRIPTION: SEQ ID NO:24:

Leu Tyr Val Glu Met Met Gln Cys Gln Ala Glu Gln Glu Pro Leu Val
1               5                   10                  15

( 2 ) INFORMATION FOR SEQ ID NO:25:

( i ) SEQUENCE CHARACTERISTICS:
  ( A ) LENGTH: 9 amino acids
  ( B ) TYPE: amino acid
  ( D ) TOPOLOGY: both ( x i ) SEQUENCE DESCRIPTION: SEQ ID NO:25:

Phe Ile Glu Gly Phe Gln Ser Asp Lys
1               5

( 2 ) INFORMATION FOR SEQ ID NO:26:

( i ) SEQUENCE CHARACTERISTICS:
  ( A ) LENGTH: 9 amino acids
  ( B ) TYPE: amino acid
  ( D ) TOPOLOGY: both ( x i ) SEQUENCE DESCRIPTION: SEQ ID NO:26:

Phe Ile Glu Gly Phe Gln Ser Asp Lys
1               5

( 2 ) INFORMATION FOR SEQ ID NO:27:

( i ) SEQUENCE CHARACTERISTICS:
  ( A ) LENGTH: 5 amino acids
  ( B ) TYPE: amino acid
  ( D ) TOPOLOGY: both ( x i ) SEQUENCE DESCRIPTION: SEQ ID NO:27:

Tyr Ala Phe Leu Lys
1               5

( 2 ) INFORMATION FOR SEQ ID NO:28:

( i ) SEQUENCE CHARACTERISTICS:
  ( A ) LENGTH: 6 amino acids
  ( B ) TYPE: amino acid
  ( D ) TOPOLOGY: both ( x i ) SEQUENCE DESCRIPTION: SEQ ID NO:28:

Gly Leu Ser Phe Ala Arg
1               5

( 2 ) INFORMATION FOR SEQ ID NO:29:

( i ) SEQUENCE CHARACTERISTICS:

(A) LENGTH: 7 amino acids
          (B) TYPE: amino acid
          (D) TOPOLOGY: both (xi) SEQUENCE DESCRIPTION: SEQ ID NO:29:

Val Ile Ala Ser Gly Glu Lys
    1               5

(2) INFORMATION FOR SEQ ID NO:30:

(i) SEQUENCE CHARACTERISTICS:
          (A) LENGTH: 4 amino acids
          (B) TYPE: amino acid
          (D) TOPOLOGY: both (xi) SEQUENCE DESCRIPTION: SEQ ID NO:30:

Phe Tyr Gln Arg
    1

(2) INFORMATION FOR SEQ ID NO:31:

(i) SEQUENCE CHARACTERISTICS:
          (A) LENGTH: 9 amino acids
          (B) TYPE: amino acid
          (D) TOPOLOGY: both (xi) SEQUENCE DESCRIPTION: SEQ ID NO:31:

Phe Tyr Gln Arg Asp Ser Phe Val Arg
    1               5

(2) INFORMATION FOR SEQ ID NO:32:

(i) SEQUENCE CHARACTERISTICS:
          (A) LENGTH: 5 amino acids
          (B) TYPE: amino acid
          (D) TOPOLOGY: both (xi) SEQUENCE DESCRIPTION: SEQ ID NO:32:

Asp Ser Phe Val Arg
    1               5

(2) INFORMATION FOR SEQ ID NO:33:

(i) SEQUENCE CHARACTERISTICS:
          (A) LENGTH: 5 amino acids
          (B) TYPE: amino acid
          (D) TOPOLOGY: both (xi) SEQUENCE DESCRIPTION: SEQ ID NO:33:

Val Leu Val Asn Asp
    1               5

(2) INFORMATION FOR SEQ ID NO:34:

(i) SEQUENCE CHARACTERISTICS:
          (A) LENGTH: 5 amino acids
          (B) TYPE: amino acid
          (D) TOPOLOGY: both (xi) SEQUENCE DESCRIPTION: SEQ ID NO:34:

Tyr Glu Ser Leu Gln
    1               5

(2) INFORMATION FOR SEQ ID NO:35:

(i) SEQUENCE CHARACTERISTICS:
          (A) LENGTH: 6 amino acids
          (B) TYPE: amino acid (D) TOPOLOGY: both (xi) SEQUENCE DESCRIPTION: SEQ ID NO:35:

Tyr Glu Ser Leu Thr Arg
1               5

(2) INFORMATION FOR SEQ ID NO:36:

(i) SEQUENCE CHARACTERISTICS:
(A) LENGTH: 7 amino acids
(B) TYPE: amino acid
(D) TOPOLOGY: both (xi) SEQUENCE DESCRIPTION: SEQ ID NO:36:

Ser Ala Ala Ser Leu Asn Ser
1               5

(2) INFORMATION FOR SEQ ID NO:37:

(i) SEQUENCE CHARACTERISTICS:
(A) LENGTH: 5 amino acids
(B) TYPE: amino acid
(D) TOPOLOGY: both (xi) SEQUENCE DESCRIPTION: SEQ ID NO:37:

Leu Lys Asp Pro Arg
1               5

(2) INFORMATION FOR SEQ ID NO:38:

(i) SEQUENCE CHARACTERISTICS:
(A) LENGTH: 7 amino acids
(B) TYPE: amino acid
(D) TOPOLOGY: both (xi) SEQUENCE DESCRIPTION: SEQ ID NO:38:

Val Ile Ala Ser Gly Glu Lys
1               5

(2) INFORMATION FOR SEQ ID NO:39:

(i) SEQUENCE CHARACTERISTICS:
(A) LENGTH: 6 amino acids
(B) TYPE: amino acid
(D) TOPOLOGY: both (xi) SEQUENCE DESCRIPTION: SEQ ID NO:39:

Tyr Pro Thr Glu Ser Lys
1               5

(2) INFORMATION FOR SEQ ID NO:40:

(i) SEQUENCE CHARACTERISTICS:
(A) LENGTH: 5 amino acids
(B) TYPE: amino acid
(D) TOPOLOGY: both (xi) SEQUENCE DESCRIPTION: SEQ ID NO:40:

Tyr Phe Asn Xaa Gly
1               5

(2) INFORMATION FOR SEQ ID NO:41:

(i) SEQUENCE CHARACTERISTICS:
(A) LENGTH: 10 amino acids
(B) TYPE: amino acid
(D) TOPOLOGY: both ( i x ) FEATURE:
    ( A ) NAME/KEY: Peptide
    ( B ) LOCATION: 3..8
    ( D ) OTHER INFORMATION: /label= Peptide
        / note= "The following are alternative amino acids at these positions: Proline at 3, Phenylalanine at 4, Serine at 6, Leucine at 7, and Valine at 8."

( x i ) SEQUENCE DESCRIPTION: SEQ ID NO:41:

Leu Glu Asn Asp Leu Asp Gly Phe Thr Leu
1                5                      10

( 2 ) INFORMATION FOR SEQ ID NO:42:

( i ) SEQUENCE CHARACTERISTICS:
        ( A ) LENGTH: 11 amino acids
        ( B ) TYPE: amino acid
        ( D ) TOPOLOGY: both ( x i ) SEQUENCE DESCRIPTION: SEQ ID NO:42:

Leu Glu Asn Asp Leu Ser Gly Val Thr Leu Thr
1                5                      10

( 2 ) INFORMATION FOR SEQ ID NO:43:

( i ) SEQUENCE CHARACTERISTICS:
        ( A ) LENGTH: 20 amino acids
        ( B ) TYPE: amino acid
        ( D ) TOPOLOGY: both ( i x ) FEATURE:
        ( A ) NAME/KEY: Peptide
        ( B ) LOCATION: 17
        ( D ) OTHER INFORMATION: /label= Peptide
            / note= "The amino acid at position 17 may also be Tyrosine."

( x i ) SEQUENCE DESCRIPTION: SEQ ID NO:43:

Tyr Tyr Gly His Gly Ala Gly Asn Pro Leu Gly Pro Thr Gln Gly Val
1                5                      10                    15

Gly Ala Asn Glu
             20

( 2 ) INFORMATION FOR SEQ ID NO:44:

( i ) SEQUENCE CHARACTERISTICS:
        ( A ) LENGTH: 3 amino acids
        ( B ) TYPE: amino acid
        ( D ) TOPOLOGY: both ( x i ) SEQUENCE DESCRIPTION: SEQ ID NO:44:

Leu Ile Ala
1

( 2 ) INFORMATION FOR SEQ ID NO:45:

( i ) SEQUENCE CHARACTERISTICS:
        ( A ) LENGTH: 8 amino acids
        ( B ) TYPE: amino acid
        ( D ) TOPOLOGY: both ( x i ) SEQUENCE DESCRIPTION: SEQ ID NO:45:

Val Thr Phe Ala Gln Val Leu Ser
1                5

( 2 ) INFORMATION FOR SEQ ID NO:46:

( i ) SEQUENCE CHARACTERISTICS:
        ( A ) LENGTH: 8 amino acids (B) TYPE: amino acid
(D) TOPOLOGY: both (xi) SEQUENCE DESCRIPTION: SEQ ID NO:46:

Phe Ile Glu Gly Phe Gln Ser Thr
1               5

(2) INFORMATION FOR SEQ ID NO:47:

(i) SEQUENCE CHARACTERISTICS:
(A) LENGTH: 7 amino acids
(B) TYPE: amino acid
(D) TOPOLOGY: both (ix) FEATURE:
(A) NAME/KEY: Peptide
(B) LOCATION: 1
(D) OTHER INFORMATION: /label= Peptide
/ note= "The amino acid at position 1 may also be Asparagine."

(xi) SEQUENCE DESCRIPTION: SEQ ID NO:47:

Asp Tyr Leu Gln Ser Leu Lys
1               5

(2) INFORMATION FOR SEQ ID NO:48:

(i) SEQUENCE CHARACTERISTICS:
(A) LENGTH: 8 amino acids
(B) TYPE: amino acid
(D) TOPOLOGY: both (xi) SEQUENCE DESCRIPTION: SEQ ID NO:48:

Asn Ile Glu Pro Phe Gln Val Asn
1               5

(2) INFORMATION FOR SEQ ID NO:49:

(i) SEQUENCE CHARACTERISTICS:
(A) LENGTH: 6 amino acids
(B) TYPE: amino acid
(D) TOPOLOGY: both (xi) SEQUENCE DESCRIPTION: SEQ ID NO:49:

Val Leu Val Asn Asp Arg
1               5

(2) INFORMATION FOR SEQ ID NO:50:

(i) SEQUENCE CHARACTERISTICS:
(A) LENGTH: 14 amino acids
(B) TYPE: amino acid
(D) TOPOLOGY: both (xi) SEQUENCE DESCRIPTION: SEQ ID NO:50:

Leu Ala Val Pro Ala Ser Arg Asp Gln Ser Thr Xaa Asp Thr
1               5                   10

(2) INFORMATION FOR SEQ ID NO:51:

(i) SEQUENCE CHARACTERISTICS:
(A) LENGTH: 3 amino acids
(B) TYPE: amino acid
(D) TOPOLOGY: both (ix) FEATURE:
(A) NAME/KEY: Peptide
(B) LOCATION: 1
(D) OTHER INFORMATION: /label= Peptide
/ note= "When deduced from the DNA sequence the -continued amino acid at position 1 was found to be cysteine."

(x i) SEQUENCE DESCRIPTION: SEQ ID NO:51:

Arg Ser Ala
1

(2) INFORMATION FOR SEQ ID NO:52:

(i) SEQUENCE CHARACTERISTICS:
(A) LENGTH: 17 base pairs
(B) TYPE: nucleic acid
(C) STRANDEDNESS: single
(D) TOPOLOGY: both (x i) SEQUENCE DESCRIPTION: SEQ ID NO:52:

CARTTRCCNC ARTTYAA            17

(2) INFORMATION FOR SEQ ID NO:53:

(i) SEQUENCE CHARACTERISTICS:
(A) LENGTH: 14 amino acids
(B) TYPE: amino acid
(D) TOPOLOGY: both (x i) SEQUENCE DESCRIPTION: SEQ ID NO:53:

Phe Ser Tyr Gly Ala Ala Ile Pro Gln Ser Thr Gln Glu Lys
1               5                   10

(2) INFORMATION FOR SEQ ID NO:54:

(i) SEQUENCE CHARACTERISTICS:
(A) LENGTH: 10 amino acids
(B) TYPE: amino acid
(D) TOPOLOGY: both (x i) SEQUENCE DESCRIPTION: SEQ ID NO:54:

Gln Phe Ser Gln Glu Phe Arg Asp Gly Tyr
1               5                   10

(2) INFORMATION FOR SEQ ID NO:55:

(i) SEQUENCE CHARACTERISTICS:
(A) LENGTH: 7 amino acids
(B) TYPE: amino acid
(D) TOPOLOGY: both (x i) SEQUENCE DESCRIPTION: SEQ ID NO:55:

Tyr Gly Gly Asn Gly Pro Tyr
1               5

(2) INFORMATION FOR SEQ ID NO:56:

(i) SEQUENCE CHARACTERISTICS:
(A) LENGTH: 6 amino acids
(B) TYPE: amino acid
(D) TOPOLOGY: both (x i) SEQUENCE DESCRIPTION: SEQ ID NO:56:

Val Ser Tyr Gly Ile Ala
1               5

(2) INFORMATION FOR SEQ ID NO:57:

(i) SEQUENCE CHARACTERISTICS:
(A) LENGTH: 13 amino acids
(B) TYPE: amino acid
(D) TOPOLOGY: both ( x i ) SEQUENCE DESCRIPTION: SEQ ID NO:57:

Arg His Gly Glu Arg Tyr Pro Ser Pro Ser Ala Gly Lys
1               5                       10

( 2 ) INFORMATION FOR SEQ ID NO:58:

( i ) SEQUENCE CHARACTERISTICS:
      ( A ) LENGTH: 8 amino acids
      ( B ) TYPE: amino acid
      ( D ) TOPOLOGY: both ( x i ) SEQUENCE DESCRIPTION: SEQ ID NO:58:

Asp Ile Glu Glu Ala Leu Ala Lys
1               5

( 2 ) INFORMATION FOR SEQ ID NO:59:

( i ) SEQUENCE CHARACTERISTICS:
      ( A ) LENGTH: 11 amino acids
      ( B ) TYPE: amino acid
      ( D ) TOPOLOGY: both ( x i ) SEQUENCE DESCRIPTION: SEQ ID NO:59:

Ala Arg Tyr Gly His Leu Trp Asn Gly Glu Thr
1               5                       10

( 2 ) INFORMATION FOR SEQ ID NO:60:

( i ) SEQUENCE CHARACTERISTICS:
      ( A ) LENGTH: 8 amino acids
      ( B ) TYPE: amino acid
      ( D ) TOPOLOGY: both ( x i ) SEQUENCE DESCRIPTION: SEQ ID NO:60:

Val Val Pro Phe Phe Ser Ser Gly
1               5

( 2 ) INFORMATION FOR SEQ ID NO:61:

( i ) SEQUENCE CHARACTERISTICS:
      ( A ) LENGTH: 7 amino acids
      ( B ) TYPE: amino acid
      ( D ) TOPOLOGY: both ( x i ) SEQUENCE DESCRIPTION: SEQ ID NO:61:

Phe Ser Ser Gly Tyr Gly Arg
1               5

( 2 ) INFORMATION FOR SEQ ID NO:62:

( i ) SEQUENCE CHARACTERISTICS:
      ( A ) LENGTH: 6 amino acids
      ( B ) TYPE: amino acid
      ( D ) TOPOLOGY: both ( x i ) SEQUENCE DESCRIPTION: SEQ ID NO:62:

Gln Leu Pro Gln Phe Lys
1               5

( 2 ) INFORMATION FOR SEQ ID NO:63:

( i ) SEQUENCE CHARACTERISTICS:
      ( A ) LENGTH: 7 amino acids
      ( B ) TYPE: amino acid
      ( D ) TOPOLOGY: both ( x i ) SEQUENCE DESCRIPTION: SEQ ID NO:63:

Val Ala Phe Gly Asn Pro Tyr
1               5

( 2 ) INFORMATION FOR SEQ ID NO:64:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: both ( i x ) FEATURE:
        ( A ) NAME/KEY: modified_base
        ( B ) LOCATION: 12
        ( D ) OTHER INFORMATION: /mod_base=i ( x i ) SEQUENCE DESCRIPTION: SEQ ID NO:64:

GTRCCNCTYK CNATRGG                                17

( 2 ) INFORMATION FOR SEQ ID NO:65:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: both ( x i ) SEQUENCE DESCRIPTION: SEQ ID NO:65:

CARCTNCCNC ARTTYAA                             17

( 2 ) INFORMATION FOR SEQ ID NO:66:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: both ( x i ) SEQUENCE DESCRIPTION: SEQ ID NO:66:

GAATTCCGAG TCCGAGGTCA TGGGCGCG                 28

( 2 ) INFORMATION FOR SEQ ID NO:67:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:67:

Met Met Gln Cys Gln Ala Glu Gln Glu Pro Leu Val Arg Val Leu Val
1               5                   10                  15

Asn Asp Arg ( 2 ) INFORMATION FOR SEQ ID NO:68:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:68:

Tyr Ala Asn Glu Leu Ile Ala (2) INFORMATION FOR SEQ ID NO:69:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:69:

```
Leu Ala Val Pro Ala Ser Arg Asn Gln Ser Thr Cys Asp Thr
 1               5                  10
```